US008685411B2

(12) United States Patent
Dormitzer et al.

(10) Patent No.: US 8,685,411 B2
(45) Date of Patent: Apr. 1, 2014

(54) ROTAVIRUS ANTIGENS

(75) Inventors: Philip R. Dormitzer, Cambridge, MA (US); Stephen C. Harrison, Cambridge, MA (US); Harry B. Greenberg, Palo Alto, CA (US); Joshua Yoder, Newtown, MA (US)

(73) Assignees: Children's Medical Center Corporation, Boston, MA (US); The Board of Trustees of the Leland Stanford Junior University, Stanford, CA (US); The United States of America as represented by the National Institutes of Health (NIH), Washington, DC (US); The United States of America as represented by the Dept. of Health and Human Services (DHHS), Washington, DC (US)

( * ) Notice: Subject to any disclaimer, the term of this patent is extended or adjusted under 35 U.S.C. 154(b) by 702 days.

(21) Appl. No.: 11/649,191

(22) Filed: Jan. 3, 2007

(65) Prior Publication Data
US 2007/0276130 A1    Nov. 29, 2007

Related U.S. Application Data

(63) Continuation-in-part of application No. PCT/US2005/023512, filed on Jul. 1, 2005.

(60) Provisional application No. 60/584,952, filed on Jul. 1, 2004.

(51) Int. Cl.
*A61K 39/15* (2006.01)
*A61K 39/12* (2006.01)
*A61K 38/00* (2006.01)

(52) U.S. Cl.
USPC .................. 424/215.1; 424/186.1; 514/1.1

(58) Field of Classification Search
None
See application file for complete search history.

(56) References Cited

U.S. PATENT DOCUMENTS

| 5,298,244 A * | 3/1994 | Redmond et al. .......... 424/186.1 |
| 7,485,415 B2 * | 2/2009 | Buonagurio et al. ............. 435/5 |
| 2003/0175301 A1 * | 9/2003 | Cohen et al. ............... 424/204.1 |

OTHER PUBLICATIONS

Gil et al. (Viral Immunology, 2000, vol. 13, No. 2, pp. 187-200).*
Denisova et al., Journal of Virology, 1999, 73(4):3147-3153.*
Nilsson et al., Virology, 1995, 208:354-358.*
Giammarioli et al., Virology, 1996, 225(1):97-110.*
Woodberry et al., Journal of Virology, 1999, 73(7):5320-5325.*
Lee et al., Can. J. Vet. Res., 1998; 62:56-62.*
Mackow et al., Proc. Natl. Acad. Sci. USA, 1990, 87:518-522.*
Kovacs-Nolan et al., Biochemical and Biophysical Research Communications, 2001, 282:1183-1188.*
GenBank Accession No. P13842 (first available on Apr. 24, 1993).*
Andrew, et al.; "The Immunogenicity of VP7, a Rotavirus Antigen Resident in the Endoplasmic Reticulum, Is Enhanced by Cell Surface Expression," J Virol 64(10):4776-4783 (Oct. 1990).
Andrew, et al.; "Vaccinia-rotavirus VP7 recombinants protect mice against rotavirus-induced diarrhoea," Vaccine 10(3):185-191 (1992).
Arias, et al.; "Trypsin Activation Pathway of Rotavirus Infectivity," J Virol 70(9): 5832-5839 (Sep. 1996).
Armentano, et al.; "Expression of human factor IX in rabbit hepatocytes by retrovirus-mediated gene transfer: Potential for gene therapy of hemophilia B," Proc. Natl. Acad. Sci. USA 87:6141-6145 (Aug. 1990).
Arnaout, et al.; "Coming to grips with integrin binding to ligands," Curr Opin Cell Biol 14, 641-651 (2002).
Bachmann, et al.; "The Influence of Antigen Organization on B Cell Responsiveness," Science 262:1448-51 (Nov. 26, 1993).
Ben-Bassat, et al.; "Processing of the Initiation Methionine from Proteins: Properties of the *Escherichia coli* Methionine Aminopeptidase and Its Gene Structure," J. of Bacteriology 169(2):751-757 (Feb. 1987).
Benvenisty, et al.; "Direct introduction of genes into rats and expression of the genes," Proc. Natl. Acad. Sci. USA 83:9551-9555 (Dec. 1986).
Bertolotti-Ciarlet, et al., "Immunogenicity and protective efficacy of rotavirus 2/6-virus-like particles produced by a dual baculovirus expression vector and administered intramuscularly, intranasally, or orally to mice," Vaccine 21:3885-3900 (2003).
Brunger, et al., "Crystallography & NMR System: A New Software Suite for Macromolecular Structure Determination," Acta Cryst. D54:905-921 (1998).
Burns, et al., "Analyses of Homologous Rotavirus Infection in the Mouse Model," Virology 207:143-153 (1995).
Burns, et al., "Protective Effect of Rotavirus VP6-Specific IgA Monoclonal Antibodies that Lack Neutralizing Activity," Science 272: 104-107 (Apr. 5, 1996).
Carpio, et al., "Role of the Histidine Triad-like Motif in Nucleotide Hydrolysis by the Rotavirus RNA-packaging Protein NSP2," J Biol Chem 279(11):10624-10633 (Mar. 12, 1994).
Chandran, et al.; "Complete in Vitro Assembly of the Reovirus Outer Capsid Produces Highly Infectious Particles Suitable for Genetic Studies of the Receptor-Binding Protein," J Virol 75(11): 5335-42 (Jun. 2001).
Chappell, et al.; "Crystal structure of reovirus attachment protein σ1 reveals evolutionary relationship to adenovirus fiber," Embo J 21(1) & (2):1-11 (2002).

(Continued)

*Primary Examiner* — Nicole Kinsey White
(74) *Attorney, Agent, or Firm* — Edwards Wildman Palmer LLP; Peter F. Corless

(57) ABSTRACT

The present invention relates to novel recombinant polypeptide antigens that may comprise subunit vaccines against rotavirus infection. Further, the present invention relates to methods for use of said antigens in the diagnosis, treatment and prevention of rotavirus infection.

6 Claims, 16 Drawing Sheets

(56) References Cited

OTHER PUBLICATIONS

Choi, et al.; "Antibody-Independent Protection against Rotavirus Infection of Mice Stimulated by Intranasal Immunization with Chimeric VP4 or VP6 Protein," J Virol 73(9):7574-7581 (Sep. 1999).
Chong, et al.; "LT(R192G), a non-toxic mutant of the heat-labile enterotoxin of *Escherichia coli*, elicits enhanced humoral and cellular immune responses associated with protection against lethal oral challenge with *Salmonella* spp." Vaccine 16(7):732-40 (1998).
Ciarlet, et al.; "Human and most animal rotavirus strains do not require the presence of sialic acid on the cell surface for efficient infectivity," J Gen Virol 80:943-948 (1999).
Ciarlet, et al.; "Subunit Rotavirus Vaccine Administered Parenterally to Rabbits Induces Active Protective Immunity," J of Virol 72(11): 9233-9246 (Nov. 1998).
Cohen, et al.; "Activation of Rotavirus RNA Polymerase by Calcium Chelation," Archives of Virology 60, 177-86 (1979).
Coulson, et al.; "Role of Coproantibody in Clinical Protection of Children during Reinfection with Rotavirus," J Clin Microbiol 30(7):1678-1684 (Jul. 1992).
Crawford, et al.; "Heterotypic Protection and Induction of a Broad Heterotypic Neutralization Response by Rotavirus-Like Particles," J Virol 73(6):4813-4822 (Jun. 1999).
Crawford, et al.; "Trypsin Cleavage Stabilizes the Rotavirus VP4 Spike," J Viro 75(13):6052-6061 (Jul. 2001).
Dormitzer, et al.; "Calcium Chelation Induces a Conformational Change in Recombinant Herpes Simplex Virus-1-Expressed Rotavirus VP7," Virology 189, 828-832 (1992).
Dormitzer, et al.; "Neutralizing Epitopes on Herpes Simplex Virus-1-Expressed Rotavirus VP7 Are Dependent on Coexpression of Other Rotavirus Proteins," Virology 187, 18-32 (1992).
Dormitzer, et al., "Presentation of Neutralizing Epitopes by Engineered Rotavirus VP7's Expressed by Recombinant Vaccinia Viruses," Virology 204:391-402 (1994).
Dormitzer, et al.; "Proteolysis of Monomeric Recombinant Rotavirus VP4 Yields an Oligomeric VP5 Core," J Virol 75(16): 7339-7350 (Aug. 2001).
Dormitzer, et al.; "Purified Recombinant Rotavirus VP7 Forms Soluble, Calcium-Dependent Trimers," Virology 277:420-428 (2000).
Dormitzer, et al.; "Specificity and Affinity of Sialic Acid Binding by the Rhesus Rotavirus VP8 Core," J Virol 76(20):10512-10517 (Oct. 2002).
Dormitzer, et al.; "The rhesus rotavirus VP4 sialic acid binding domain has a galectin fold with a novel carbohydrate binding site," The EMBO J., 21(5):885-897 (2002).
Douce, et al.; "Genetically Detoxified Mutants of Heat-Labile Toxin from *Escherichia coli* Are Able to Act as Oral Adjuvants," Infection and Immunity 67(9): 4400-4406 (Sep. 1999).
Dowling, et al.; "Selective Membrane Permeabilization by the Rotavirus VP5 Protein Is Abrogated by Mutations in an Internal Hydrophobic Domain," J Virol 74(14):6368-6376 (Jul. 2000).
Dunn, et al.; "Immunogenicity, antigenicity, and protection efficacy of baculovirus expressed VP4 trypsin cleavage products, VP5(1) and VP8 from rhesus rotavirus," Arch Virol 140:1969-1978 (1995).
Estes, et al.; "Proteolytic Enhancement of Rotavirus Infectivity: Molecular Mechanisms," J Virol 39(3):879-888 (Sep. 1981).
Fiore, et al.; "Antigenicity, immunogenicity and passive protection induced by immunization of mice with baculovirus-expressed VP7 protein from rhesus rotavirus," J Gen Virol 76:1981-1988 (1995).
Fiore, et al.; "The VP8 Fragment of VP4 Is the Rhesus Rotavirus Hemagglutinin," Virology 181:553-563 (1991).
Franco, et al.; "Immunity to homologous rotavirus infection in adult mice," Trends in Microbiology 8(2):50-52 (Feb. 2000).
Franco, et al.; "Immunity to Rotavirus in T Cell Deficient Mice," Virology 238, 169-179 (1997).
Franco, et al.; "Role of B Cells and Cytotoxic T Lymphocytes in Clearance of and Immunity to Rotavirus Infection in Mice," J Virol 69(12): 7800-7806 (Dec. 1995).
Gajardo, et al.; "Two Proline Residues Are Essential in the Calcium-Binding Activity of Rotavirus VP7 Outer Capsid Protein," J Virol 71(3):2211-2216 (Mar. 1997).
Gentsch, et al.; "Review of G and P Typing Results from a Global Collection of Rotavirus Strains: Implications for Vaccine Development," J Infect Dis 174(Suppl 1):S30-36 (1996).
Gibbons, et al., "Conformational change and protein-protein interactions of the fusion protein of Semliki Forest virus," Nature 427:320-325 (Jan. 22, 2004).
Gilbert, et al.; "Cleavage of Rhesus Rotavirus VP4 after Arginine 247 Is Essential for Rotavirus-Like Particle-Induced Fusion from Without," J Virol 72(6):5323-5327 (Jun. 1998).
Godley, et al.; "Introduction of Intersubunit Disulfide Bonds in the Membrane-Distal Region of the Influenza Hemagglutinin Abolishes Membrance Fusion Activity," Cell 68:635-645 (Feb. 21, 1992).
Gonzalez, et al.; "Antibody responses to human rotavirus (HRV) in gnotobiotic pigs following a new prime/boost vaccine strategy using oral attenuated HRV priming and intranasal VP2/6 rotavirus-like particle (VLP) boosting with ISCOM," Clin Exp Immunol 135:361-372 (2004).
Gorziglia, et al.; "Neutralization Epitopes on Rotavirus SA11 4fM Outer Capsid Proteins," J Virol 64(9):4534-4539 (Sep. 1990).
Graham, K. L., et al.; Integrin-Using Rotaviruses Bind α2β1 Integrin α2 I Domain via VP4 DGE Sequence and Recognize αX β2 and αVβ3 by Using VP7 during Cell Entry, J Virol 77(18):9969-9978 (Sep. 2003).
Halperin, et al.; "A phase I study of the safety and immunogenicity of recombinant hepatitis B surface antigen co-administered with an immunostimulatory phosphorothioate oligonucleotide adjuvant," Vaccine 21:2461-2467 (2003).
Holm, et al.; "Protein Structure Comparison by Alignment of Distance Matrices," J. Mol Biol 233:123-138 (1993).
Jayaram, et al.; "Rotavirus protein involved in genome replication and packaging exhibits a HIT-like fold," Nature 417, 311-315 (May 16, 2002).
Jones, et al.; "Improved Methods for Building Protein Models in Electron Density Maps and the Location of Errors in these Models," Acta Cryst. A47:110-119 (1991).
Kapikian, et al.; "An Epidemiologic Study of Altered Clinical Reactivity to Respiratory Syncytial (RS) Virus Infection in Children Previously Vaccinated with an Inactivated RS Virus Vaccine," Am J Epidemiol 89(4):405-421 (1969).
Kapikian, et al.; "Rotavirus: The Major Etiologic Agent of Severe Infantile Diarrhea May Be Controllable by a "Jennerian" Approach to Vaccination," J Infect Dis 153(5):815-22 (May 1986).
Kirkwood, et al., "Human rotavirus VP4 contains strain-specific, serotype-specific and cross-reactive neutralization sites," Arch Virol 141, 587-600 (1996).
Kobayashi, et al.; "Identification of operationally overlapping and independent cross-reactive neutralization regions on human rotavirus VP4," J Gen Virol 71:2615-2623 (1990).
Lawton, et al.; "Automated Software Package for Icosahedral Virus Reconstruction," J Struct Biol 116:209-215 (1996).
Lawton, et al.; "Three-dimensional visualization of mRNA release from actively transcribing rotavirus particles," Nat Struct Biol 4(2):118-121 (Feb. 1997).
Lepault, et al.; "Structural polymorphism of the major capsid protein of rotavirus," Embo J 20(7):1498-1507 (2001).
Lescar, et al.; "The Fusion Glycoprotein Shell of Semliki Forest Virus: An Icosahedral Assembly Primed for Fusogenic Activation at Endosomal pH," Cell 105:137-148 (Apr. 6, 2001).
Liemann, et al., Structure of the Reovirus Membrane-Penetration Protein, μ1, in a Complex with Its Protector Protein, σ3, Cell 108:283-295 (Jan. 25, 2002).
Lovgren, et al., "The Iscom: An Antigen Delivery System With Built-In Adjuvant," Mol Immunol 28(3):285-286 (1991).
Ludert, et al.; "Antibodies to Rotavirus Outer Capsid Glycoprotein VP7 Neutralize Infectivity by Inhibiting Virion Decapsidation," J Virol 76(13):6643-6651 (Jul. 2002).
Ludert, et al.; "Identification of mutations in the rotavirus protein VP4 that alter sialic-acid-dependent infection," J Gen Virol 79:725-729 (1998).

(56) References Cited

OTHER PUBLICATIONS

Ludtke, et al.; "EMAN: Semiautomated Software for High-Resolution Single-Particle Reconstructions," J Struct Biol 128:82-97 (1999).
Lycke; "From toxin to adjuvant: the rational design of a vaccine adjuvant vector, CTA1-DD/ISCOM," Cellular Microbiology 6(1):23-32 (2004).
Mackow, et al., "Characterization of Homotypic and Heterotypic VP7 Neutralization Sites of Rhesus Rotavirus," Virology 165:511-517 (1988).
Mackow, et al.; "Immunization with Baculovirus-Expressed VP4 Protein Passively Protects against Simian and Murine Rotavirus Challenge," J Virol 64(4): 1698-1703 (Apr. 1990).
Mackow, et al.; "The rhesus rotavirus gene encoding protein VP3: Location of amino acids involved in homologous and heterologous rotavirus neutralization and identification of a putative fusion region," Proc Natl Acad Sci USA 85:645-649 (Feb. 1988).
Mackow, et al., "The Rhesus Rotavirus Outer Capsid Protein VP4 Functions as a Hemagglutinin and Is Antigenically Conserved When Expressed by a Baculovirus Recombinant," J Virol 63(4):1661-1668 (Apr. 1989).
Mathieu, et al., "Atomic structure of the major capsid protein of rotavirus: implications for the architecture of the virion," EMBO J 20(7):1485-1497 (2001).
Matson, et al., "Fecal Antibody Responses to Symptomatic and Asymptomatic Rotavirus Infections," J Infect Dis 167:577-583 (1993).
McCluskie, et al., "Cutting Edge: CpG DNA Is a Potent Enhancer of Systemic and Mucosal Immune Responses Against Hepatitis B Surface Antigen with Intranasal Administration to Mice," J Immunol 161:4463-4466 (1998).
Modis, et al.; "Structure of the dengue virus envelope protein after membrane fusion," Nature 427:313-319 (Jan. 2004).
Mowat, et al.; "Oral vaccination with immune stimulating complexes," Immunol Lett 65:133-40 (1999).
Mutsch, et al.; "Use of the Inactivated Instranasal Influenza Vaccine and the Risk of Bell's Palsy in Switzerland," N Engl J Med 350:896-903 (2004).
Nicholls, et al.; "Protein Folding and Association: Insights From the Inerfacial and Thermodynamic Properties of Hydrocarbons," Proteins: Structure, Function, and Genetics 11:281-296 (1991).
Offit, et al.; "Passive Protection against Rotavirus-Induced Diarrhea by Monoclonal Antibodies to Surface Proteins vp3 and vp7," J Virol 58(2):700-703 (May 1986).
Offit, et al., "Protection Against Rotavirus-Induced Gastroenteritis in a Murine Model by Passively Acquired Gastrointestinal But Not Circulating Antibodies," J Virol 54(1):58-64 (Apr. 1985).
Padilla, et al.; "A statistic for local intensity differences: robustness to anisotropy and pseudo-centering and utility for detecting twinning," Acta Crystallogr D59:1124-1130 (2003).
Padilla-Noriega, et al.; "Identification of Two Independent Neutralization Domains on the VP4 Trypsin Cleavage Products VP5 and VP8 of Human Rotavirus ST3," Virology 206:148-154 (1995).
Parashar, et al.; "Global Illness and Deaths Caused by Rotavirus Disease in Children," Emerg Infect Dis 9(5):565-572 (May 2003).
Prasad, et al.; "Localization of VP4 neutralization sites in rotavirus by three-demensional cryo-electron microscopy," Nature 343:476-479 (Feb. 1, 1990).
Prasad, et al.; "Three-dimensional Structure of Rotavirus," J Mol Biol 199:269-275 (1988).
Rey, et al.; "The envelope glycoprotein from tick-borne encephalitis virus at 2 A resolution," Nature 375:291-298 (May 25, 1995).
Roman, et al.; "Immunostimulatory DNA sequences function as T helper-1-promoting adjuvants," Nat Med 3(8):849-854 (Aug. 1997).
Ruggeri, et al.; "Antibodies to the Trypsin Cleavage Peptide VP8 Neutralize Rotavirus by Inhibiting Binding of Virions to Target Cells in Culture," J Viro 65(5):2211-2219 (May 1991).
Ruigrok, et al.; "Studies on the Structure of the Influenza Virus Haemagglutinin at the pH of Membrane Fusion," J Gen Virol 69: 2785-2795 (1988).
Schuck, et al.; "Rotavirus Nonstructural Protein NSP2 Self-assembles into Octamers That Undergo Ligand-induced Conformational Changes," J Biol Chem 276(13):9679-9687 (Mar. 30, 2001).
Schwartz-Cornil, et al.; Heterologous Protection Induced by the Inner Capsid Proteins of Rotavirus Requires Transcytosis of Mucosal Immunoglobulins, J Virol 76(16):8110-8117 (Aug. 2002).
Shaw, et al.; "Antigenic Mapping of the Surface Proteins of Rhesus Rotavirus," Virology 155:434-451 (1986).
Shaw, et al.; "Three-Dimensional Visualization of the Rotavirus Hemagglutinin Structure," Cell 74:693-701 (Aug. 27, 1993).
Svensson, et al.; "Immune Response to Rotavirus Polypeptides after Vaccination with Heterologous Rotavirus Vaccines (RIT 4237, RRV-1)," J Gen Virol 68 (Pt 7):1993-1999 (1987).
Taniguchi, et al.; "Identification of Cross-Reactive and Serotype 2-Specific Neutralization Epitopes on VP3 of Human Rotavirus," J Virol 62(7):2421-2426 (1988).
Tessier, et al.; "Enhanced secretion from insect cells of a foreign protein fused to the honeybee melittin signal peptide," Gene 98, 177-183 (1991).
Tihova, et al.; "Localization of Membrane Permeabilization and Receptor Binding Sites on the VP4 Hemagglutinin of Rotavirus: Implications for Cell Entry," J Mol Biol 314:985-992 (2001).
Walz, et al.; "Electron Crystallography of Two-Dimensional Crystals of Membrane Proteins," J Struct Biol 121:142-161 (1998).
Weeks, et al.; "The design and implementation of SnB version 2.0," J Appl Cryst 32:120-124 (1999).
Weissenhorn, et al.; "The ectodomain of HIV-1 env subunit gp41 forms a soluble, -helical, rod-like oligomer in the absence of gp120 and the N-terminal fusion peptide," EMBO J 15(7): 1507-1514 (1996).
Wiley, et al.; "Structural identification of the antibody-binding sites of Hong Kong influenza haemagglutinin and their involvement in antigenic variation," Nature 289:373-378 (Jan. 29, 1981).
Wriggers, et al.; "Situs: A Package for Docking Crystal Structures into Low-Resolution Maps from Electron Microscopy," J Struct Biol 125:185-195 (1999).
Wyatt, et al.; "The antigenic structure of the HIV gp120 envelope glycoprotein," Nature 393:705-711 (Jun. 18, 1998).
Yeager, et al.; "Three-dimensional Structure of Rhesus Rotavirus by Cryoelectron Microscopy and Image Reconstruction," J Cell Biol 110:2133-2144 (Jun. 1990).
Yeager, et al.; "Three-dimensional structure of the rotavirus haemagglutinin VP4 by cryo-electron microscopy and difference map analysis," EMBO J 13(5):1011-1018 (1994).
Yuan, et al.; "Antibody-Secreting Cell Responses and Protective Immunity Assessed in Gnotobiotic Pigs Inoculated Orally or Intramuscularly with Inactivated Human Rotavirus," J Virol 72(1):330-3388 (Jan. 1998).
Yuan, et al.; "Induction of mucosal immune responses and protection against enteric viruses: rotavirus infection of gnotobiotic pigs as a model," Vet Immunol Immunopathol 87: 147-160 (2002).
Yuan, et al.; "Intranasal Administration of 2/6-Rotavirus-Like Particles with Mutant *Escherichia coli* Heat-Labile Toxin (LT-R192G) Induces Antibody-Secreting Cell Responses but Not Protective Immunity in Gnotobiotic Pigs," J Virol 74(19):8843-8853 (Oct. 2000).
Yuan, et al.; "Protective Immunity and Antibody-Secreting Cell Responses Elicited by Combined Oral Attenuated Wa Human Rotavirus and Intranasal Wa 2/6-VLPs with Mutant *Escherichia coli* Heat-Labile Toxin in Gnotobiotic Pigs," J Virol 75(19):9229-9238 (Oct. 2001).
Yuan, et al.; "Systemic and Intestinal Antibody-Secreting Cell Responses and Correlates of Protective Immunity to Human Rotavirus in a Gnotobiotic Pig Model of Disease," J Virol 70(5):3075-3083 (May 1996).
Zhang, et al.; "Conformational Changes of gp120 in Epitopes near the CCR5 Binding Site Are Induced by CD4 Miniprotein Mimetic," Biochemistry 38:9405-9416 (1999).
Shaw, R. D. et al., "Antigenic Mapping of the Surface Proteins of Rhesus Rotavirus", *Virology*. 155:434-451 (Academic Press, Inc., 1986).

\* cited by examiner

FIGURE 7

Biochemical Characteristics of the RRV, DS-1, and KU VP8* cores

| | RRV | DS-1 | KU |
|---|---|---|---|
| Rotavirus VP4 residues in construct | 60-224 | 60-223 | 60-223 |
| Predicted MW | 18570.6 | 18758.3 | 18882.4 |
| MW fresh[a] | 18592.8 | 18826.8 | 19104.4 |
| MW after storage[a] | 18568.2 | 18734.3 | multiple fragments |
| Length of storage (days) | 798 | 718 | 767 |
| Apparent MW (kD)[b] | 23.6 (after storage) | 17.4 (after storage) | 7.9 (fresh) |
| Yield (mg/L of bacterial culture)[c] | 16 | 8.6 | 2.6 |
| Solubility (mg/ml) | ≥ 88 | ≥ 39.1 | ≥ 22.7 |

[a] Determined by MALDI mass spectrometry.

[b] Based on elution volume by gel filtration chromatography (Fig. 1).

[c] Yield refers to final purified VP8* core.

FIGURE 9

Neutralization Escape Mutations Selected by mAbs That Recognize VP8* of Human Rotavirus Strains

| mAb | Escape mutation (strain)[a] | Immunization regimen | P genotypes neutralized (not neutralized)[b] | Immunized species | Initial Screen | Reference |
|---|---|---|---|---|---|---|
| 1-2H | G170D (KU) | natural infection | P[4, 8] (P[5, 6, 9, 10]) | human | binding | Higo-Moriguchi, et al. |
| 2-3E | E203K (KU) | natural infection | P[6, 8] (P[4, 5, 9, 10]) | human | binding | Higo-Moriguchi, et al. |
| HS6 | T72I (ST3) | IP[c] with ST3 | P[6, +/-8][d] (P[4]) | mouse | neutralization | Padilla-Noriega, et al. (II) |
| HS11 | E217K (ST3) | IP with ST3 | P[6] (P[4, 8]) | mouse | neutralization | Padilla-Noriega, et al. (II) |
| RV-5:2 | Q148R (RV-5) | IP and IV[e] with RV-5 | P[4] (P[2, 3, 5, 6, 8, 10]) | mouse | neutralization | Coulson, et al. |

FIGURE 12

VP5* Antigen Trimer

VP5CT

NH2

COOH

FIGURE 13 VP5* Antigen Trimer Hydrophobic Interactions

FIGURE 15
Modification of NSP2-VP8 fusion protein

1. Linker between NSP2 and VP8* core shortened (original could have stretched 87 angstroms!)
2. His tag between NSP2 and VP8* removed.
3. Protease-susceptible arginines removed.
4. Linker to C-terminal His tag lengthened (for increased accessibility).

Gen 1

H$_6$: six histidine affinity tag
GPGP: glycine-proline-glycine-proline flexible hinge Gen 2

ELISA and neutralization titers from immunized guinea pig sera

SEQUENCE LISTING

<160> NUMBER OF SEQ ID NOS: 14

<210> SEQ ID NO 1
<211> LENGTH: 164
<212> TYPE: PRT
<213> ORGANISM: Human rotavirus

<400> SEQUENCE: 1

```
Thr Val Glu Pro Val Leu Asp Gly Pro Tyr Gln Pro Thr Thr Phe Lys
1               5                  10                  15

Pro Pro Asn Asp Tyr Trp Leu Leu Ile Ser Ser Asn Thr Asn Gly Val
            20                  25                  30

Val Tyr Glu Ser Thr Asn Asn Asn Asp Phe Trp Thr Ala Val Ile Ala
        35                  40                  45

Val Glu Pro His Val Ser Gln Thr Asn Arg Gln Tyr Ile Leu Phe Gly
    50                  55                  60

Glu Asn Lys Gln Phe Asn Val Glu Asn Ser Asp Lys Trp Lys Phe
65                  70                  75                  80

Phe Glu Met Phe Lys Gly Ser Ser Gln Gly Asp Phe Ser Asn Arg Arg
                85                  90                  95

Thr Leu Thr Ser Ser Asn Arg Leu Val Gly Met Leu Lys Tyr Gly Gly
            100                 105                 110

Arg Val Trp Thr Phe His Gly Glu Thr Pro Arg Ala Thr Thr Asp Ser
        115                 120                 125

Ser Asn Thr Ala Asp Leu Asn Asn Ile Ser Ile Ile His Ser Glu
    130                 135                 140

Phe Tyr Ile Ile Pro Arg Ser Gln Glu Ser Lys Cys Asn Glu Tyr Ile
145                 150                 155                 160

Asn Asn Gly Leu
```

<210> SEQ ID NO 2
<211> LENGTH: 164
<212> TYPE: PRT
<213> ORGANISM: Human rotavirus

<400> SEQUENCE: 2

```
Thr Val Glu Pro Ile Leu Asp Gly Pro Tyr Gln Pro Thr Thr Phe Lys
1               5                  10                  15

Pro Leu Thr Asp Tyr Trp Ile Leu Ile Asn Ser Asn Thr Asn Gly Val
            20                  25                  30

Val Tyr Glu Ser Thr Asn Asn Ser Asp Phe Trp Thr Ala Val Val Ala
        35                  40                  45

Val Glu Pro His Val Asn Pro Val Asp Arg Gln Tyr Thr Val Phe Gly
    50                  55                  60

Glu Asn Lys Gln Phe Asn Val Arg Asn Asp Ser Asp Lys Trp Lys Phe
65                  70                  75                  80

Leu Glu Met Phe Arg Gly Ser Ser Gln Asn Glu Phe Tyr Asn Arg Arg
                85                  90                  95

Thr Leu Thr Ser Asp Thr Lys Leu Val Gly Ile Leu Lys Tyr Gly Gly
            100                 105                 110

Arg Ile Trp Thr Phe His Gly Glu Thr Pro Arg Ala Thr Thr Asp Ser
        115                 120                 125

Ser Asn Thr Ala Asn Leu Asn Asp Ile Ser Ile Ile His Ser Glu
    130                 135                 140

Phe Tyr Ile Ile Pro Arg Ser Gln Glu Ser Lys Cys Asn Glu Tyr Ile
```

```
                  145                 150                 155                 160
Asn Asn Gly Leu

<210> SEQ ID NO 3
<211> LENGTH: 165
<212> TYPE: PRT
<213> ORGANISM: Rhesus rotavirus

<400> SEQUENCE: 3

Thr Val Glu Pro Val Leu Asp Gly Pro Tyr Gln Pro Thr Thr Phe Asn
  1               5                  10                  15

Pro Pro Val Asp Tyr Trp Met Leu Leu Ala Pro Thr Ala Ala Gly Val
             20                  25                  30

Val Val Glu Gly Thr Asn Asn Thr Asp Arg Trp Leu Ala Thr Ile Leu
         35                  40                  45

Val Glu Pro Asn Val Thr Ser Glu Thr Arg Ser Tyr Thr Leu Phe Gly
     50                  55                  60

Thr Gln Glu Gln Ile Thr Ile Ala Asn Ala Ser Gln Thr Gln Trp Lys
 65                  70                  75                  80

Phe Ile Asp Val Val Lys Thr Thr Gln Asn Gly Ser Tyr Ser Gln Tyr
                 85                  90                  95

Gly Pro Leu Gln Ser Thr Pro Lys Leu Tyr Ala Val Met Lys His Asn
            100                 105                 110

Gly Lys Ile Tyr Thr Tyr Asn Gly Glu Thr Pro Asn Val Thr Thr Lys
        115                 120                 125

Tyr Tyr Ser Thr Thr Asn Tyr Asp Ser Val Asn Met Thr Ala Phe Cys
    130                 135                 140

Asp Phe Tyr Ile Ile Pro Arg Glu Glu Glu Ser Thr Cys Thr Glu Tyr
145                 150                 155                 160

Ile Asn Asn Gly Leu
                165

<210> SEQ ID NO 4
<211> LENGTH: 233
<212> TYPE: PRT
<213> ORGANISM: Rhesus rotavirus

<400> SEQUENCE: 4

Arg Ala Gln Ala Asn Glu Asp Ile Val Val Ser Lys Thr Ser Leu Trp
  1               5                  10                  15

Lys Glu Met Gln Tyr Asn Arg Asp Ile Thr Ile Arg Phe Lys Phe Ala
             20                  25                  30

Ser Ser Ile Val Lys Ser Gly Gly Leu Gly Tyr Lys Trp Ser Glu Ile
         35                  40                  45

Ser Phe Lys Pro Ala Asn Tyr Gln Tyr Thr Tyr Thr Arg Asp Gly Glu
     50                  55                  60

Glu Val Thr Ala His Thr Thr Cys Ser Val Asn Gly Met Asn Asp Phe
 65                  70                  75                  80

Asn Phe Asn Gly Gly Ser Leu Pro Thr Asp Phe Val Ile Ser Arg Tyr
                 85                  90                  95

Glu Val Ile Lys Glu Asn Ser Tyr Val Tyr Val Asp Tyr Trp Asp Asp
            100                 105                 110

Ser Gln Ala Phe Arg Asn Met Val Tyr Val Arg Ser Leu Ala Ala Asn
        115                 120                 125

Leu Asn Ser Val Ile Cys Thr Gly Gly Asp Tyr Ser Phe Ala Leu Pro
    130                 135                 140
```

```
Val Gly Gln Trp Pro Val Met Thr Gly Gly Ala Val Ser Leu His Ser
145                 150                 155                 160

Ala Gly Val Thr Leu Ser Thr Gln Phe Thr Asp Phe Val Ser Leu Asn
            165                 170                 175

Ser Leu Arg Phe Arg Phe Arg Leu Thr Val Glu Glu Pro Ser Phe Ser
        180                 185                 190

Ile Thr Arg Thr Arg Val Ser Arg Leu Tyr Gly Leu Pro Ala Ala Asn
        195                 200                 205

Pro Asn Asn Gly Lys Glu Tyr Tyr Glu Val Ala Gly Arg Phe Ser Leu
        210                 215                 220

Ile Ser Leu Val Pro Ser Asn Asp Asp
225                 230

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Val Glu Pro Val
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Leu Glu Pro Val
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Val Glu Pro Val Ser
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gly Ser Gly Gly
  1               5

<210> SEQ ID NO 9
<211> LENGTH: 272
<212> TYPE: PRT
<213> ORGANISM: Rhesus rotavirus
```

```
<400> SEQUENCE: 9

Glu Asp Ile Val Val Ser Lys Thr Ser Leu Trp Lys Glu Met Gln Tyr
 1               5                  10                  15

Asn Arg Asp Ile Thr Ile Arg Phe Lys Phe Ala Ser Ser Ile Val Lys
             20                  25                  30

Ser Gly Gly Leu Gly Tyr Lys Trp Ser Glu Ile Ser Phe Lys Pro Ala
         35                  40                  45

Asn Tyr Gln Tyr Thr Tyr Thr Arg Asp Gly Glu Glu Val Thr Ala His
     50                  55                  60

Thr Thr Cys Ser Val Asn Gly Met Asn Asp Phe Asn Phe Asn Gly Gly
 65                  70                  75                  80

Ser Leu Pro Thr Asp Phe Val Ile Ser Arg Tyr Glu Val Ile Lys Glu
                 85                  90                  95

Asn Ser Tyr Val Tyr Val Asp Tyr Trp Asp Ser Gln Ala Phe Arg
            100                 105                 110

Asn Met Val Tyr Val Arg Ser Leu Ala Ala Asn Leu Asn Ser Val Ile
            115                 120                 125

Cys Thr Gly Gly Asp Tyr Ser Phe Ala Leu Pro Val Gly Gln Trp Pro
130                 135                 140

Val Met Thr Gly Gly Ala Val Ser Leu His Ser Ala Gly Val Thr Leu
145                 150                 155                 160

Ser Thr Gln Phe Thr Asp Phe Val Ser Leu Asn Ser Leu Arg Phe Arg
                165                 170                 175

Phe Arg Leu Thr Val Glu Glu Pro Ser Phe Ser Ile Thr Arg Thr Arg
                180                 185                 190

Val Ser Arg Leu Tyr Gly Leu Pro Ala Ala Asn Pro Asn Asn Gly Lys
            195                 200                 205

Glu Tyr Tyr Glu Val Ala Gly Arg Phe Ser Leu Ile Ser Leu Val Pro
210                 215                 220

Ser Asn Asp Asp Tyr Gln Thr Pro Ile Thr Asn Ser Val Thr Val Arg
225                 230                 235                 240

Gln Asp Leu Glu Arg Gln Leu Gly Glu Leu Arg Glu Glu Phe Asn Ala
                245                 250                 255

Leu Ser Gln Glu Ile Ala Met Ser Gln Leu Ile Asp Leu Ala Leu Leu
            260                 265                 270

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser His His His His His His Gly Pro Gly Pro
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Pro Gly Pro Ser His His His His His
 1               5                  10
```

```
<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 12

His His His His His His
  1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Gly Pro
  1

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Gly Gly Ser Leu Val Pro Arg Gly Ser His His His His
  1               5                  10                  15

His His
```

ROTAVIRUS ANTIGENS

RELATED APPLICATIONS

This application is a continuation-in-part of International Application No. PCT/US05/023512, filed Jul. 1, 2005, which claims the benefit of Provisional Application 60/584,952, filed Jul. 1, 2004.

GOVERNMENT SUPPORT

Support for research leading to this invention was provided in part by the National Institutes of Health through National Institute of Allergy and Infectious Diseases grants K08 AI 001496 and R01 AI 053174, through National Cancer Institute grant R01 CA 13202, and by a Veteran's Administration Merit Review Grant. Accordingly the United States Government has certain rights with respect to the invention.

BACKGROUND OF THE INVENTION

Rotaviruses are the most common cause of severe vomiting and diarrhea in children worldwide and infect virtually all children by 3 to 4 years of age. Each year among children younger than 5 years of age, about 440,000 deaths worldwide are attributable to rotavirus. In the United States, rotavirus only kills 20-40 children annually, but is responsible for 570,000 physician visits and 55,000 hospitalizations, costing approximately $264 million in direct health care costs and $1 billion in total costs, including the cost of time missed from work by caregivers. Rotavirus also affects adults and is more severe in the elderly Among major worldwide causes of childhood mortality, rotavirus gastroenteritis is particularly amenable to definitive public health intervention by a suitable vaccine. A suitable vaccine would raise neutralizing antibodies, particularly in the gut, to protect against rotavirus gastroenteritis. However, production of such a vaccine has not been facile. A live, oral vaccine against rotavirus (RotaShield) was released in the United States in 1998, but was withdrawn due to a temporal association between immunization and intestinal intussusception. Therefore, a safe, effective, inexpensive, and heat-stable vaccine against rotavirus is urgently needed.

SUMMARY OF THE INVENTION

Innovative structure-based vaccine design could avoid the problems described above. We can apply structural insights to specifically engineer the molecules that present the targets of protective immunity and then verify that these epitopes are present and stable. One format for presenting such engineered antigens is a subunit vaccine, which would be composed of homogeneous, pure components and would be inherently non-infectious and safe to produce. Structure-based antigens can also be integrated with DNA- or vector-based immunization strategies, to improve the efficacy and safety of these relatively new vaccine technologies. The fine control over vaccine characteristics allowed by structure-based molecular engineering could create a new generation of inexpensive, safe vaccines, which more reliably present known neutralization determinants to the host immune system.

We have used the high-resolution structural data of fragments of the rotavirus neutralization antigen VP4 to rationally design a variety of polypeptides to be incorporated into vaccines against rotavirus infection. Further, we have also used the high-resolution structural data of fragments of the rotavirus neutralization antigen VP4 to elucidate the mechanism of viral entry.

Accordingly, provided herein are various polypeptides derived from rotavirus VP4, such as for example, the VP5* antigen domain and the VP8* core. Recombinant versions of such polypeptides, as well as fusions, domains, fragments, variants and derivatives thereof, are also provided. Further provided are isolated nucleic acid sequences encoding the polypeptides or polypeptide fragments, as well as vectors, host cells, and cultures thereof.

In some embodiments, the polypeptides and fragments are antigens. Antibodies specific to such antigens may be raised according to methods well-known in the art. The antigenic polypeptides and nucleic acids may comprise immunogenic compositions and vaccines. Hence, such polypeptides, and nucleic acids encoding such polypeptides may be used as part of an immunogenic composition or vaccine, for example, formulated in a pharmaceutically acceptable carrier, to prevent rotavirus infection. Such immunogenic compositions or vaccines may further other compounds such as adjuvants, or combinations of the antigens (e.g., antigens against various rotavirus strains) of the invention.

The immunogenic compositions and vaccines of the present invention may be used in methods of treating and preventing rotavirus in mammals, for example, humans. In other embodiments, the above-described methods may further serve to vaccinate said mammal rather than simply elicit an immunogenic response.

Such polypeptides have been crystallized and their structures solved as described in detail below, thereby providing information about the structure of the polypeptide, and allowing the identification of structural domains that may serve as antigens and the like contained therein, all of which may be used in vaccine design methods. In particular, information critical to the design of vaccine molecules, including, for example, the protein domains, antigenic regions, structural information, and the like for the polypeptides of the invention is now available or attainable as a result of the ability to prepare, purify and characterize them, and domains, fragments, variants and derivatives thereof.

In other embodiments, kits including the subject nucleic acids, polypeptides, antibodies, and other subject materials, and optionally instructions for their use, are provided. Kits comprising the vaccines and other pharmaceutical compositions of the present invention are also within the scope of the invention. Uses for such kits include, for example, diagnostic, preventative, and therapeutic applications. The embodiments and practices of the present invention, other embodiments, and their features and characteristics, will be apparent from the description, figures and claims that follow, with all of the claims hereby being incorporated by this reference into this Summary.

The practice of the present invention may employ in part, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells*

And Enzymes (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

BRIEF DESCRIPTION OF THE FIGURES

FIG. 1A: The nonenveloped virion has three protein layers: an inner icosahedral layer, made of VP2 and containing the viral genome, polymerase, and guanyltransferase; a middle icosahedral layer, made of VP6; and an outer icosahedral layer, made of VP7. The inner two layers make up the DLP. Sixty VP4 spikes protrude from the virion. Each spike has a head (H), body (B), stalk (S), and foot (F). The drawing is based on an electron cryomicroscopy image reconstruction. FIG. 1B: VP8* (1-231) and VP5* (248-776) are VP4 cleavage fragments produced by trypsin activation of virions. VP8CT and VP5CT are cleavage fragments produced by sequential chymotrypsin and trypsin digestion of purified recombinant VP4. VP8CT forms the head. Residues from both VP8* and VP5*, including VP5CT, form the body. The C-terminal portion of VP5* forms the stalk and foot.

FIG. 2A: The trimer viewed perpendicular to its three-fold symmetry axis. "Top" and "bottom" are based on this perspective. The green and blue subunits depict residues 254-519, and the yellow subunit depicts residues 252-517. "MI"—putative membrane interaction loop. FIG. 2B: The trimer viewed along the three-fold symmetry axis from the bottom. This view shows the hydrophobic apex of the globular domains, made up of the B'C', D'E', and F'G loops. FIG. 2C: The trimer viewed along the three-fold symmetry axis from the top. The protruding CD β-hairpin, tipped by the putative integrin-binding site (Int), arcs towards the reader.

FIG. 3A: Secondary structure assignment of the primary amino acid sequence (SEQ ID NO:9). β-strands are arrows; the α-helix is a yellow tube. Dashed outlines at the N- and C-termini indicate regions where the secondary structure varies with crystal contacts. Blue letters indicate amino acid positions selected in neutralization escape mutants. Blue boxes indicate neutralization escape mutations in strain RRV. The green underline identifies the DGE integrin-binding motif. The red underline identifies the putative membrane interaction loop. Residues that make hydrophobic contacts around the three-fold axis of the triple-stranded coiled-coil as predicted by a heptad repeat pattern are indicated by "a" or "d." FIG. 3B: Ribbon diagram of residues 254-523. Each β-sheet has a different color, matching the diagram in FIG. 3A. The orientation matches that of the blue monomer in FIG. 2A. The orange β-sheet contributes three strands to the nine-stranded β-annulus, as do the equivalent sheets of the other two subunits. "Int"—integrin-binding motif. "MI"—putative membrane interaction loop.

FIG. 4 depicts various views of the VP5CT surface. Blue surfaces have positive electrostatic potential; red surfaces have negative potential. Surfaces formed by residues selected in neutralizing antibody escape mutants are labeled with black text boxes and residue numbers colored by epitope: 5-1, yellow; 5-2, white; 5-3, green; 5-4, pink; 5-5, orange. Other surfaces are labeled with black text in white boxes. Orientations match those in FIG. 2. FIG. 4A: VP5CT surface viewed perpendicular to the three-fold axis. "I254," "L517," and "D519" are the N- and C-termini of the region depicted in this figure. FIG. 4B: Viewed along the three-fold symmetry axis from the bottom. Surfaces formed by hydrophobic residues at apex of the globular domain are labeled on the upper left subunit. FIG. 4C: VP5CT surface viewed along the three-fold symmetry axis from the top. The "propeller" formed by tryptophan side chains from each subunit forms the surface labeled "W262" at the base of a pore-like ring on the three-fold axis. The integrin binding motif at the tip of the claw-like CD loop is labeled "D308," "G309," and "E310" here and in FIG. 4A.

FIG. 5 depicts the fit of VP8CT and the VP5CT globular domain to an electron cryomicroscopy image reconstruction. The models in FIG. 5D-5F are rotated 90° about a vertical axis relative to those in FIG. 5A-5C. FIGS. 5A and 5D: Surface models of VP8CT and the VP5CT globular domain, oriented as in the dimeric spike. The surfaces are colored by conservation in a set of 20 sequences, one from each P genotype: blue, conserved; red, variable. Neutralization epitopes are outlined: 5-1, solid yellow; 5-2, solid white; 5-3, solid green; 5-4, solid pink; 5-5, solid orange; 8-1, dashed yellow; 8-2, dashed white; 8-3, dashed green; 84, dashed pink. The red asterix marks the sialoside-binding cleft of VP8CT. FIGS. 5B and 5E: Cα-traces of VP8CT and VP5CT residues are fit to an image reconstruction of trypsinized virions at ~12 Å resolution, contoured at 0.45 Å. Labeled residues: 65 and 224, termini of the VP8CT trace; 267 and 470, termini of the VP5CT trace; 309, glycine of the DGE integrin-binding motif (CD loop); 393, immunodominant site in the putative membrane interaction region (F'G loop); 417, tip of the GH hairpin, which contributes to the central β-annulus in the trimer. FIGS. 5C and 5F: Ribbon diagrams of VP5CT residues 254-523 oriented as in the dimeric spike. The globular domain that fits the spike is colored as in FIG. 3. The N- and C-terminal regions that must have a different conformation in the spike are black with white outlines. Only the proximal subunit is shown in FIG. 5F. The CD, F'G, and GH loops are marked.

FIG. 6 depicts a model for VP4 rearrangements during priming and entry. FIG. 6A depicts uncleaved VP4. The wavy lines indicate the flexibility of the spikes, resulting in loss from averaged image reconstructions. The VP7 shell is blue. FIG. 6B depicts trypsin-primed VP4. The two clustered molecules correspond to the spike visible in electron cryomicroscopy image reconstructions. The head is a yellow oval with a notch for the sialoside-binding cleft. The body includes the red and orange "kidney" (the VP5CT globular domain with its putative membrane interaction region), the purple appendage, and part of the gray and cyan tubes. The stalk is the lower part of the cyan tubes. The foot is the green hexagonal prism. The activation region (brown in FIG. 6A) separating VP8* and VP5* has been removed by proteolysis. FIG. 6C depicts the post-membrane penetration state, corresponding to the crystal structure. The blue line is dashed because this conformation may form after loss of VP7 due to virion un-coating. FIG. 6D depicts a linear diagram of VP4 structural elements colored to match the cartoons. Residues forming each element: gray, M1-V64; yellow, L65-L224; pink, P225-R231; brown, N232-R247; purple, A248-Q266; red, Y267-T381 and A401-L470; orange, G382-G400; cyan, 1471-unknown; green, unknown-L776. The VP8* and VP5* fragments are in black boxes.

FIG. 7 contains a table with biochemical data on the RRV, DS-1, and KU VP8* cores.

FIG. 8A depicts a ribbon diagram of the DS-1 VP8* core. Labeling of secondary structure elements is as previously described for the RRV VP8* core except that strand βH is continuous in DS-1 but split into strands βH and βH' in RRV. FIG. 8B depicts superimposed Cα traces of the DS-1 VP8* core (blue) and the RRV VP8* core (red). Residue Q135 of RRV, which lacks a structural equivalent in DS-1 is indicated. The blue and red arrows indicate the width of surface clefts in angstroms for the DS-1 and RRV VP8* cores, respectively. FIG. 8C depicts a surface representation of the DS-1 VP8* core colored by electrostatic potential. Blue is positive; red is negative. The bound leader of an adjacent molecule in the asymmetric unit is depicted with a ball-and-stick model. Residues in the space filling model are labeled in white text boxes. Residues in the ball-and-stick model are labeled in yellow text boxes. FIG. 8D depicts a surface representation of the RRV VP8* core colored as in panel C. The bound sialoside is depicted with a ball-and-stick model.

FIG. 9 depicts neutralization escape mutations selected by mAbs that recognize VP8* of human rotavirus strains.

FIG. 10A depicts a portion of the asymmetric unit of the DS-1 VP8* core crystal. FIG. 10B depicts the binding of the leader in a pocket lined by hydrophobic residues at the base of the cleft.

FIG. 12 depicts the crystal structure of VP5CT (left) and the crystal structure of the VP5* antigen (R247-D479) trimer (right).

FIG. 13 depicts various views of the hydrophobic interactions and certain residues involved in the same for the VP5* antigen (R247-D479) trimer.

FIG. 15 depicts schematics of two NSP2-VP8 fusion proteins (Gen 1 and Gen 2) used in the immunogenicity studies described in Example 13 (SEQ ID NOS 10-14 are shown respectively in order of appearance).

DETAILED DESCRIPTION OF THE INVENTION

A. General

Figure 1:
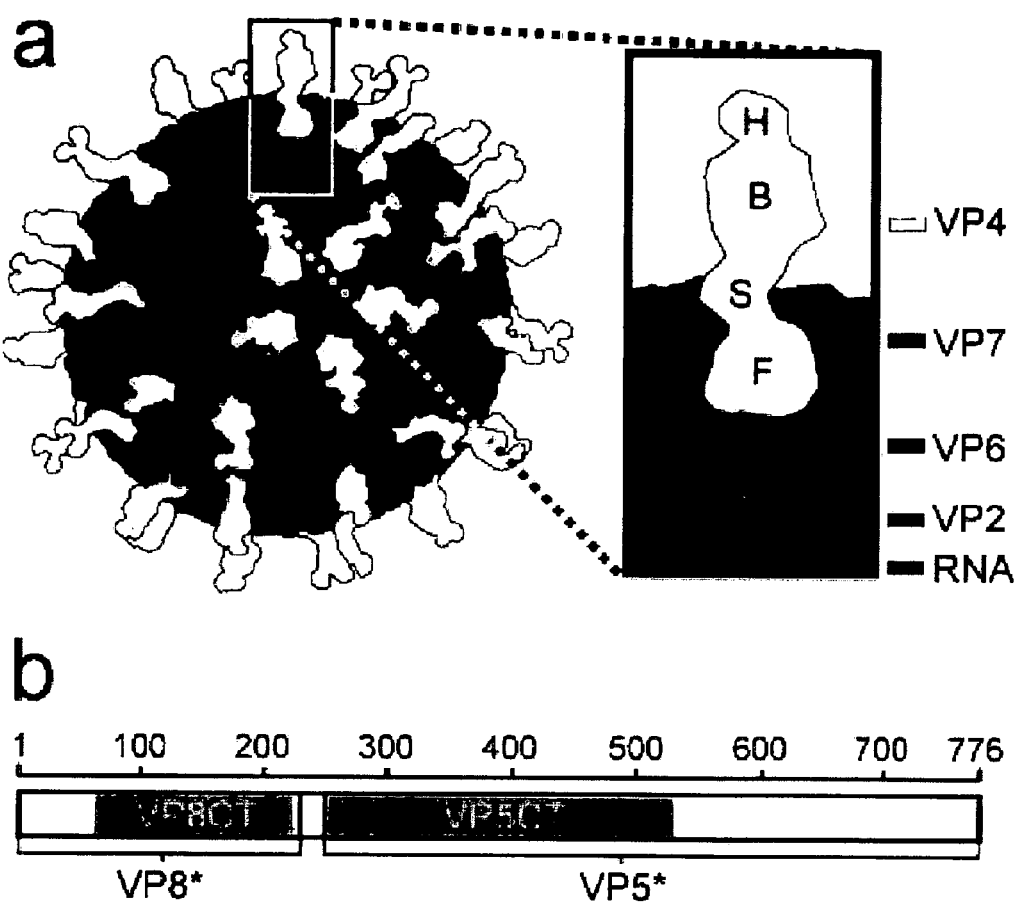
FIG. 1 depicts the structure of the virion and domains of rotavirus VP4.

Rotavirus has 2 neutralization antigens, VP4 and VP7. Neutralizing antibodies recognizing these proteins, when present in the gut lumen, protect from rotavirus gastroenteritis. When expressed recombinantly, both VP4 and VP7 have characteristics that are undesirable in a recombinant immunogen. Recombinant VP4 is sensitive to protease degradation. Recombinant VP7 is sensitive to degradation and fails to stably form the conformation that contains neutralizing epitopes. During the virus replication cycle, authentic VP4 on the virion is cleaved by intestinal trypsin into 2 fragments, VP8* and VP5*. Both of these fragments contain neutralization epitopes. The VP5* fragment contains epitopes recognized by antibodies that neutralize a wide variety of rotavirus strains and may be particularly important in protection from those that cause human disease. Although VP8* and VP5* would, therefore, appear to be promising candidates for recombinant immunogens. Prior to the current work, direct recombinant expression of VP8* or VP5* has not yielded preparations shown to be pure, homogeneous, soluble, efficiently produced, and stable and, therefore, suitable for use in immunization. These antigens may also present targets for inhibitors of rotavirus replication and entry.

We have carried out biochemical and structural analyses of recombinant VP4, VP8*, and VP5*. These analyses include protease mapping, analytical ultracentrifugation, gel filtration chromatography, nuclear magnetic resonance spectroscopy, x-ray crystallography, and recombinant protein engineering. The analyses show that VP8* and VP5* each contain a single well-folded, protease-resistant, soluble, biochemically stable domain. The 2 domains contain all known neutralizing epitopes of VP4. Our analyses have identified the boundaries of these domains, which we call "the VP8* core" and the "globular domain of VP5CT" or "VP5* antigen domain." In strain RRV, the boundaries of the VP8* core are approximately residues 60-224 of full length VP4. The boundaries of the globular domain of VP5CT or "VP5* antigen domain" are approximately residues 267-479 of full length VP4. We have shown that recombinant proteins containing these domains (with some variations in the exact boundaries) can be efficiently expressed and purified as recombinant antigens and have very favorable biochemical characteristics for inclusion in recombinant vaccines against rotavirus. These domains may be expressed in a number of recombinant systems and presented to the immune system by a variety of vehicles and routes. Recombinant proteins based on these structural domains may also serve as recombinant immunogens. Further, such recombinant proteins may serve as targets in assays to identify modulators of the mechanism of rotavirus entry.

B. Definitions

For convenience, before further description of the present invention, certain terms employed in the specification, examples, and appendant claims are collected here. These definitions should be read in light of the entire disclosure and understood as by a person of skill in the art.

The articles "a" and "an" are used herein to refer to one or to more than one (i.e., to at least one) of the grammatical object of the article. By way of example, "an element" means one element or more than one element.

An "adjuvant" is a substance that in combination with specific antigen may produce a greater immunogenic response than the antigen alone.

An "antigen" is a substance that stimulates the production or mobilization of antibodies. An antigen may be, for example, a foreign protein, toxin, bacterium, or other substance. The term "antigenically active" also refers to a substance which has the ability to act as an antigen. In particular, as used herein, it refers to a substance which is a fragment, derivative, or variant of a particular antigen, but still retains the antigenic properties of the antigen.

The term "antibody" as used herein is intended to include fragments thereof which are also specifically reactive with a polypeptide of the invention. Antibodies can be fragmented using conventional techniques and the fragments screened for utility in the same manner as is suitable for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules, as well as single chain (scFv) antibodies. Also within the scope of the invention are trimeric antibodies, humanized antibodies, human antibodies, and single chain antibodies. All of these modified forms of antibodies as well as fragments of antibodies are intended to be included in the term "antibody".

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "binding" refers to an association, which may be a stable association, between two molecules, e.g., between a polypeptide of the invention and a binding partner, due to, for example, electrostatic, hydrophobic, ionic and/or hydrogen-bond interactions under physiological conditions.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

The term "gene" refers to a nucleic acid comprising an open reading frame encoding a polypeptide having exon sequences and optionally intron sequences. The term "intron" refers to a DNA sequence present in a given gene which is not translated into protein and is generally found between exons.

A "gene involved in rotavirus-induced host cell permeation and/or necrosis" refers to a gene which enables a rotavirus to engage in host epithelial cell membrane permeation and/or induce necrosis of such cells. The term "immunogenic" refers to the ability of a substance to elicit an immune response. An "immunogenic composition" or "immunogenic substance" is a composition or substance which elicts an immune response. An "immune reponse" refers to the reaction of a subject to the presence of an antigen, which may include at least one of the following: making antibodies, developing immunity, developing hypersensitivity to the antigen, and developing tolerance.

The term "immunity" refers to the ability of an organism to resist or overcome an infection. The term "protective immunity" refers to the ability of an organism to resist an infection.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" refers to a nucleic acid encoding a polypeptide of the invention.

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

A "patient," "subject" or "host" to be treated by the subject method may mean either a human or non-human animal.

The phrase "pharmaceutically acceptable" refers to those compositions and dosages thereof within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. The term "pharmaceutically acceptable carrier" refers to a carrier(s) that is "acceptable" in the sense of being compatible with the other ingredients of a composition and not deleterious to the recipient thereof. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "phenotype" refers to the entire physical, biochemical, and physiological makeup of a cell, e.g., having any one trait or any group of traits.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a potential structural domain that could serve as an antigen, and optionally additional amino acids on one or both sides of the potential structural domain that could serve as an antigen, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described in the Exemplification section herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; Gene Expression Technology: Methods in Enzymology, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "soluble" as used herein with reference to a polypeptide of the invention or other protein, means that upon centrifugation at least some portion of the purified polypeptide remains in solution and does not form a pellet. Solubility may be further qualified by the sedimentation of the polypeptide at given concentration in the presence of a given buffer or other component of the mixture in which assay of solubility is performed. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups). The solubility of polypeptides may be measured using a variety of art recognized techniques, including centrifugation to separate aggregated from non-aggregated material; analytical ultracentrifugation, dynamic light scattering, and gel filtration chromatography to determine hydrodynamic parameters (such as sedimentation coefficient, apparent molecular weight, hydrodynamic radius, diffusion coefficient, and monodispersity); and SDS gel electrophoresis, UV absorption, or Bradford determination (e.g., the amount of protein in the soluble fraction is compared to the amount of protein in the soluble and insoluble fractions combined). In certain embodiments, a one liter culture of cells expressing a polypeptide of the invention will produce at least about 0.1, 0.2, 0.5, 1, 2, 5, 10, 20, 30, 40, 50 milligrams or more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The term "strain" as used herein refers to a rotavirul cell derived from a primary culture or cell line by the selection and cloning of cells having specific properties.

The terms "structural domain" or "structural motif", when used in reference to a polypeptide, refers to a polypeptide that, although it may have different amino acid sequences, may result in a similar structure, wherein by structure is meant that the domain or motif forms generally the same tertiary structure, or that certain amino acid residues within the motif, or alternatively their backbone or side chains (which may or may not include the Cα atoms of the side chains) are positioned in a like relationship with respect to one another in the domain or motif. These terms may be used interchangeably herein.

As applied to proteins, the term "substantial identity" means that two protein sequences, when optimally aligned, such as by the programs GAP or BESTFIT using default gap weights, typically share at least about 70 percent sequence identity, alternatively at least about 80, 85, 90, 95 percent sequence identity or more. In certain instances, residue positions that are not identical differ by conservative amino acid substitutions, which are described above.

The phrases "systemic administration," "administered systemically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

The term "test compound" refers to a molecule to be tested by one or more screening method(s) as a putative modulator of a polypeptide of the invention or other biological entity or process. A test compound is usually not known to bind to a target of interest. The term "control test compound" refers to a compound known to bind to the target (e.g., a known agonist, antagonist, partial agonist or inverse agonist). The term "test compound" does not include a chemical added as a control condition that alters the function of the target to determine signal specificity in an assay. Such control chemicals or conditions include chemicals that 1) nonspecifically or substantially disrupt protein structure (e.g., denaturing agents (e.g., urea or guanidinium), chaotropic agents, sulfhydryl reagents (e.g., dithiothreitol and b-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). Further, the term "test compound" also does not include compounds known to be unsuitable for a therapeutic use for a particular indication due to toxicity of the subject. In certain embodiments, various predetermined concentrations of test compounds are used for screening such as 0.01 mM, 0.1 mM, 1.0 mM, and 10.0 mM. Examples of test compounds include, but are not limited to, peptides, nucleic acids, carbohydrates, and small molecules. The term "novel test compound" refers to a test compound that is not in existence as of the filing date of this application. In certain assays using novel test compounds, the novel test compounds comprise at least about 50%, 75%, 85%, 90%, 95% or more of the test compounds used in the assay or in any particular trial of the assay.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treating" as used herein is intended to encompass curing as well as ameliorating at least one symptom of any condition or disease.

The term "vaccine" refers to a substance that elicits an immune response and also confers protective immunity upon a subject.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. Infectious expression vectors, such as recombinant baculoviruses, are used to express proteins in cultured cells. Other infectious expression vectors, such as recombinant adenoviruses and vaccinia viruses, are used as vaccines to express foreign antigens in vaccines. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

C. Polypeptides

Provided are isolated, recombinant polypeptides derived from rotavirus VP5* and VP8*. Polypeptides derived from these domains may be from any rotavirus strain, including, but not limited to RRV, SA11 c13, CU-1, OSU, L338, Lp14, FRV-1, K8, ALA, HAL1166, EC. Ty-1, EHP, UK, 69M, H-2, RV-5, Gott, ST3, Wa, B233, 116E, PRV 4F, Mc323, ITO, YO, MO, Hochi, VA70, DS-1, L26, EW, EB, NCDV, YM, EL, M37, Au-1, HCR3, Ro1845, 993/83, KU, P; RV-4, W178, S2, KUN, 1076, McN, RV-3, and 57M. Such polypeptides may comprise antigens, as described below, and may be identified and/or optimized, for example, using the rational design methods described below. Recombinant versions of such polypeptides, as well as fusions, domains, fragments, variants and derivatives thereof, are also provided by the present invention.

Accordingly, where polypeptide sequences or features of polypeptide sequences having a sequence numbering schemes particular to one rotavirus strain are described and claimed, it is to be understood that homologous sequences and/or equivalent features may be present in polypeptides from another rotavirus strain having a different sequence numbering system.

For example, polypeptides comprising the DS-1 VP8* (residues 60-223 from DS-1 VP4) core sequence (SEQ ID NO: 1: TVEPVLDGPY QPTTFKPPND YWLLISSNTN GVVYESTNNN DFWTAVIAVE PHVSQTNRQYILF- GENKQFN VENNSDKWKF FEMFKGSSQG DFSNR- RTLTS SNRLVGMLKY GGRVWTFHGETPRATTDSSN TADLNNISII IHSEFYIIPR SQESKCNEYI NNGL) or fragments and variants thereof are provided.

In another example. polypeptides comprising the KU VP8* (residues 60-223 from KU VP4) core sequence (SEQ ID NO: 2: TVEPILDGPY QPTTFKPLTD YWILINSNTN GVVYESTNNS DFWTAVVAVE PHVNPVDRQY TVF- GENKQFN VRNDSDKWKF LEMFRGSSQN EFYNR- RTLTS DTKLVGILKY GGRIWTFHGE TPRATTDSSN TANLNDISII IHSEFYIIPR SQESKCNEYI NNGL) or fragments and variants thereof are provided.

In another example. polypeptides comprising the RRV VP8* (residues 60-224 from RRV VP4) core sequence (SEQ ID NO: 3: TVEPVLDGPYQPTTFNPPVDYWML- LAPTAAGVVVEGTNNTDRWLATILVEPNVTSE TRSYTLFGTQEQITIANASQTQWKFIDV- VKTTQNGSYSQYGPLQSTPKLYAVMKHNG KIYTYN- GETPNVTTKYYSTTNYDSVNMTAFCD- FYIIPREEESTCTEYINNGL) or fragments and variants thereof are provided.

Further, polypeptides comprising the RRV VP5* antigen domain (residues 247-479 from RRV VP4) sequence (SEQ ID NO: 4: RAQA NEDIVVSKTS LWKEMQYNRD ITIR- FKFASS IVKSGGLGYK WSEISFKPAN YQYTYTRDGE EVTAHTTCSV NGMNDFNFNG GSLPTDFVIS RYEVIK- ENSY VYVDYWDDSQ AFRNMVYVRS LAANLNSVIC TGGDYSFALP VGQWPVMTGG AVSLHSAGVT LSTQFTDFVS LNSLRFRFRL TVEEPSFSIT RTRVSR- LYGL PAANPNNGKE YYEVAGRFSL ISLVPSNDD) or fragments and variants thereof are provided. For example, polypeptides may comprise residues 247-479 from RRV VP4 in certain embodiments, but in other embodiments may comprise more minimal fragments such as residues 267-479 or residues 263-474 of RRV VP4 in other embodiments.

In certain embodiments, the present invention provides an isolated recombinant polypeptide or fragment thereof having, for example, at least about 30%, at least about 40%, at least about 50%, at least about 60%, at least about 70%, at least about 80%, at least about 85%, at least about 90%, at least about 95%, at least about 96%, at least about 97%, at least about 98%, or at least about 99% identity to the polypeptides described above. Further provided are polypeptides derived from rotavirus that may have low identity to the polypeptides described above, but have the same protein fold or structural domains.

In certain embodiments, the polypeptides of the invention may be modified so as to increase their immunogenicity. For example, a polypeptide, such as an antigenically or immunologically equivalent derivative, may be associated, for example by conjugation, with an immunogenic carrier protein for example bovine serum albumin (BSA) or keyhole limpet hemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

In certain embodiments, the above-described VP8* and VP5* antigen domain polypeptides and fragments may comprise a larger, multidomain protein construct or a fusion protein. In certain embodiments, the VP8* and VP5* antigen domain polypeptides and fragments may comprise a multidomain construct having multiple copies of the VP8* and VP5* antigen domain polypeptides and fragments, or a mixture of the VP8* and VP5* antigen domain polypeptides and fragments (e.g., at least one copy each of a VP8* and a VP5* antigen domain polypeptide or fragment). In other embodiments, the multidomain construct may comprise at least one other molecule, for example, a multivalent display platform. Suitable multivalent display platforms include VP6 and NSP2 platforms. Such multivalent display platforms and multivalent constructs produced thereby encompassed by the term "fusion polypeptides" when used, e.g., in the claims, throughout this application.

Techniques for optimizing antigens to make them ideal immunogens include (1) reducing complex antigenic molecules to their neutralization epitope-containing domains; (2) stabilizing antigen conformation by engineering disulfide cross-links; (3) increasing production efficiency by mutating residues to alter the hydrophobic surfaces that cause aggregation and insolubility; (4) enhancing immunogenicity by displaying the neutralization epitopes on multivalent platforms; (5) facilitating inoculation by mucosal routes by mutating surface-exposed protease sites. Other techniques for optimizing antigens are described in the Examples below.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

In certain embodiments, the hydrophobic residues outside of the neutralization epitopes present on the antigen may be mutated to more hydrophilic residues or deleted. Such mutations and deletions must be selected such that the epitopes maintain their conformation and electrostatic profile.

In certain embodiments, the subject polypeptides may comprise a fusion protein containing at least one domain which increases its solubility and/or facilitates its purification, identification, detection, and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, at both the N- and C-terminus of the polypeptide or at a location within the coding sequence of the polypeptide. Linker sequences between a polypeptide of the invention and the fusion domain may be included in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, the subject polypeptides may be modified so that the rate of traversing the cellular membrane is increased. For example, the polypeptide may be fused to a second peptide which promotes "transcytosis," e.g., uptake of the peptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) *Cell* 55:1179-1188). Alternatively, the internalizing peptide may be derived from the *Drosophila antennapedia* protein, or homologs thereof. The 60 amino acid long homeodomain of the homeo-protein antennapedia has been demonstrated to translocate through biological membranes and can facilitate the translocation of heterologous polypeptides to which it is coupled. Thus, polypeptides may be fused to a peptide consisting of about amino acids 42-58 of *Drosophila antennapedia* or shorter fragments for transcytosis (Derossi et al. (1996) *J Biol Chem* 271:18188-18193; Derossi et al. (1994) *J Biol Chem* 269: 10444-10450; and Perez et al. (1992) *J Cell Sci* 102:717-722). The transcytosis polypeptide may also be a non-naturally-occurring membrane-translocating sequence (MTS), such as the peptide sequences disclosed in U.S. Pat. No. 6,248,558.

Accordingly the present invention also provides isolated nucleic acid sequences encoding the polypeptides or polypeptide fragments (referred to in the remainder of this section collectively as "polypeptide"), as well as vectors, host cells, and cultures thereof.

In embodiments wherein a polypeptide fragment is provided, said polypeptide fragment may be produced using standard polypeptide synthesis methods as will be known to one of skill in the art. Alternatively, such polypeptide fragments, as well as the subject polypeptides, may be produced using recombinant techniques. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

Another aspect of the invention relates to polypeptide fragments derived from the full-length polypeptides of the invention. Isolated peptidyl portions of those polypeptides may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, proteins may be arbitrarily divided into fragments of desired length with no overlap of the fragments, or may be divided into overlapping fragments of a desired length. The fragments may be produced (recombinantly or by chemical synthesis) and tested to identify those peptidyl fragments having a desired property, for example, the capability of functioning as a modulator of the polypeptides of the invention. In an illustrative embodiment, peptidyl portions of a protein of the invention may be tested for binding activity, as well as inhibitory ability, by expression as, for example, thioredoxin fusion proteins, each of which contains a discrete fragment of a protein of the invention (see, for example, U.S. Pat. Nos. 5,270,181 and 5,292,646; and PCT publication WO94/02502).

Expression vehicles for production of a recombinant polypeptide include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli. In one aspect of the invention, the subject nucleic acid is provided in a vector comprising a nucleotide sequence encoding a polypeptide of the invention, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a chimeric polypeptide. Approaches include insertion of the nucleic acid in viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell. The subject nucleic acids may be used to cause expression and over-expression of polypeptide of interest in cells propagated in culture, e.g. to produce proteins or polypeptides.

This invention also pertains to a host cell transfected with a recombinant gene in order to express a polypeptide of the invention. The host cell may be any prokaryotic or eukaryotic cell. For example, a gene comprising a polypeptide of interest may be expressed in bacterial cells, such as E. coli, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide are known to those in the art.

A cell culture includes host cells, media and other byproducts. Suitable media for cell culture are well known in the art. A polypeptide may be secreted and isolated from a mixture of cells and medium comprising the polypeptide. Alternatively, a polypeptide may be retained cytoplasmically and the cells harvested, lysed and the protein isolated. A polypeptide may be isolated from cell culture medium, host cells, or both using techniques known in the art for purifying proteins, including ion-exchange chromatography, gel filtration chromatography, ultrafiltration, electrophoresis, and affinity purification with antibodies specific for particular epitopes or with the ligand of a fusion tag.

Generally, a nucleic acid encoding a polypeptide of the invention is introduced into a host cell, such as by transfection or infection, and the host cell is cultured under conditions allowing expression of the polypeptide. Methods of introducing nucleic acids into prokaryotic and eukaryotic cells are well known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

Thus, a nucleotide sequence encoding all or part of a polypeptide of the invention may be used to produce a recombinant form of a protein via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

Other embodiments of nucleic acid sequences encoding the polypeptides of the invention, as well as vectors, host cells, and cultures thereof are further described below.

In another embodiment, the nucleic acid encoding a polypeptide of the invention is operably linked to a bacterial promoter, e.g., the anaerobic *E. coli*, i promoter or the *E. coli* lipoprotein llp promoter, described, e.g., in Inouye et al. (1985) *Nucl. Acids Res.* 13:3101; *Salmonella* pagC promoter (Miller et al., supra), *Shigella* ent promoter (Schmitt and Payne, *J. Bacteriol.* 173:816 (1991)), the tet promoter on Tn10 (Miller et al., supra), or the ctx promoter of *Vibrio cholera*. Any other promoter can be used in the invention. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

In another embodiment, a signal peptide sequence is added to the construct, such that the polypeptide is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor.

In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. (Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) *Gene* 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the invention.

In another embodiment, the bacterium further comprises a DNA encoding a second polymerase which is capable of mediating transcription from the second promoter, wherein the DNA encoding the second polymerase is operably linked to a third promoter. In a preferred embodiment, the third promoter is a bacterial promoter. However, more than two different polymerases and promoters could be introduced in a bacterium to obtain high levels of transcription. The use of one or more polymerase for mediating transcription in the bacterium can provide a significant increase in the amount of polypeptide in the bacterium relative to a bacterium in which the DNA is directly under the control of a bacterial promoter. The selection of the system to adopt will vary depending on the specific use of the invention, e.g., on the amount of protein that one desires to produce.

When using a prokaryotic host cell, the host cell may include a plasmid which expresses an internal T7 lysozyme, e.g., expressed from plasmid pLysSL (see Examples). Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., $t_0$ from phage lambda and $t_4$ from the rrnB operon in *E. coli*, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pFastBac-derived vectors.

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression of a polypeptide may be driven by any of a number of promoters. For example, viral promoters such as the 35S RNA and 19S RNA promoters of CaMV (Brisson et al., 1984, Nature, 310:511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224:838-843); or heat shock promoters, eg., soybean hsp 17.5-E or hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol., 46:584, Smith, U.S. Pat. No. 4,215,051).

In a specific embodiment of an insect system, the DNA encoding the subject polypeptide is cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from *Trichoplusia ni* egg cell homogenates; available from Invitrogen, San Diego, Calif.) insect cells, to produce large quantities of appropriately post-translationally modified subject polypeptide. Although it is possible that these cells themselves could be directly useful for drug assays, the subject polypeptides prepared by this method can be used for in vitro assays.

In another embodiment, the subject polypeptides are prepared in transgenic animals, such that in certain embodiments, the polypeptide is secreted, e.g., in the milk of a female animal.

Viral vectors may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo, particularly into mammals. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the antisense E6AP constructs, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14, and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for nucleic acids encoding the subject polypeptides, it is important to note that a prerequisite for the successful infection of target cells by most retroviruses, and therefore of stable introduction of the genetic material, is that the target cells must be dividing. In general, this requirement will not be a hindrance to use of retroviral vectors. In fact, such limitation on infection can be beneficial in circumstances wherein the tissue (e.g., nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example, PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) *PNAS* 86:9079-9083; Julan et al. (1992) *J. Gen Virol* 73:3251-3255; and Goud et al. (1983) *Virology* 163:251-254); or coupling cell surface ligands to the viral env proteins (Neda et al. (1991) *J Biol Chem* 266:14143-14146). Coupling can be in the form of the chemical cross-linking with a protein or other variety (e.g., lactose to convert the env protein to an asialoglycoprotein), as well as by generating chimeric proteins (e.g., single-chain antibody/env chimeric proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the genetic material of the retroviral vector.

Another viral gene delivery system utilizes adenovirus-derived vectors. The genome of an adenovirus can be manipulated such that it encodes a gene product of interest, but is inactive in terms of its ability to replicate in a normal lytic viral life cycle (see, for example, Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, for example, Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject chimeric polypeptides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors comprising as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes.

In a representative embodiment, genetic material can be entrapped in liposomes bearing positive charges on their surface (e.g., lipofectins) and, optionally, which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viac et al. (1978) *J Invest Dermatol* 70:263-266; see also Mizuno et al. (1992) *Neurol. Med. Chir.* 32:873-876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) *Science* 260-926; Wagner et al. (1992) *PNAS* 89:7934; and Christiano et al. (1993) *PNAS* 90:2122).

D. Antigens

The polypeptides of the invention, or fragments thereof may comprise rotavirus antigens. Antigens generally have the ability to induce an immunogenic response. More specifically, the antigens of interest are targets of neutralizing antibodies against rotavirus. Protective immunity against rotavirus is most strongly associated with the presence of a neutralizing antibody response against the virus and with the presence of rotavirus-specific antibodies in the gut lumen. Thus, the antigens should contain the structures recognized by neutralizing antibodies and be incorporated into preparations that can induce these antibodies. Assays for recognition of the antigens by neutralizing antibodies include visualization of protein structure, visualization of protein-antibody complexes, and reactivity between antigen and antibodies in enzyme-linked immunosorbent assay (ELISA) or immunoprecipitation formats. Assays for the ability to induce appropriate antibodies in immunized animals include tests for serum neutralization of rotavirus particles; tests for serum, intestinal, or fecal antibodies recognizing rotavirus recombinant or native antigens (ELISA or immunoprecipitation or western blot); and tests for rotavirus-specific or recombinant antigen-specific antibody-producing cells in the lamina propria, Peyer's patches, mesenteric lymph nodes, spleen, or peripheral blood (enzyme-linked immunospot assay—ELISPOT).

Cell mediated immunity may also have some role in protection from rotavirus infection. More specifically, antigens have the ability to induce proliferation and/or cytokine production (i.e., interferon-.gamma. and/or interleukin-12 production) in T cells, NK cells, B cells and/or macrophages derived from a rotavirus-immune individual. The selection of cell type for use in evaluating an immunogenic response to a antigen will depend on the desired response. For example, interleukin-12 production is most readily evaluated using preparations containing B cells and/or macrophages. T cells, NK cells, B cells and macrophages derived from rotavirus-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through "FICOLL" (Winthrop Laboratories, N.Y.). T cells for use in the assays described herein may also be purified directly from PBMCs. These cells may then be cloned and tested with individual proteins, using methods known to those of ordinary skill in the art, to more accurately define individual T cell specificity. In general, antigens that test positive in assays for proliferation and/or cytokine production (i.e., interferon-.gamma. and/or interleukin-12 production) performed using T cells, NK cells, B cells and/or macrophages derived from an rotavirus-immune individual are considered immunogenic. Such assays may be performed, for example, using the representative procedures described below in the Exemplification. Immunogenic portions of such antigens, e.g. "antigenically active fragments," may be identified using similar assays, and may be present within the polypeptides described herein.

The ability of a polypeptide (e.g., an immunogenic antigen, or a portion or other variant thereof) to induce cell proliferation may be evaluated, for example, by contacting the cells (e.g., T cells and/or NK cells) with the polypeptide and measuring the proliferation of the cells. In general, the amount of polypeptide that is sufficient for evaluation of about 10.sup.5 cells ranges from about 10 ng/mL to about 100 .mu.g/mL and preferably is about 10 .mu.g/mL. The incubation of polypeptide with cells is typically performed at 37.degree. C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-.gamma. and/or interleukin-12 in cells may be evaluated, for example, by contacting the cells with the polypeptide and measuring the level of interferon-.gamma. or interleukin-12 produced by the cells. In general, the amount of polypeptide that is sufficient for the evaluation of about $10^5$ cells ranges from about 10 ng/mL to about 100 μg/mL and preferably is about 10 μg/mL. The polypeptide may be, but need not be, immobilized on a solid support, such as a bead or a biodegradable microsphere, such as those described in U.S. Pat. Nos. 4,897,268 and 5,075,109. The incubation of polypeptide with the cells is typically performed at 37°C. for about six days. Following incubation with polypeptide, the cells are assayed for interferon-γ. and/or interleukin-12 (or one or more subunits thereof), which may be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50 pg of interferon-γ. per mL of cultured supernatant (containing $10^4$-$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3 \times 10^5$ PBMC) is considered able to stimulate the production of IL-12.

In general, immunogenic antigens are those antigens that stimulate proliferation and/or cytokine production (i.e., interferon-γ. and/or interleukin-12 production) in T cells, NK cells, B cells and/or macrophages derived from at least about 25% of rotavirus-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals who are not rotavirus-immune, thereby eliminating responses that are not specifically due to rotavirus-responsive cells. Those antigens that induce a response in a high percentage of T cell, NK cell, B cell and/or macrophage preparations from rotavirus-immune individuals (with a low incidence of responses in cell preparations from other individuals) have superior therapeutic properties.

Antigens with superior therapeutic properties may also be identified based on their ability to diminish the severity of rotavirus infection in experimental animals, when administered as a vaccine. Suitable vaccine preparations for use on experimental animals are described in detail below. Efficacy may be determined based on the ability of the antigen to provide at least about a 70% reduction in shed virus antigen or infectious particles and/or at least about a 70% decrease in diarrhea following experimental infection. Suitable experimental animals include mice, pigs, and primates.

E. Immunogenic Compositions and Vaccines and Methods of Use

1. Immunogenic Compositions and Vaccines Comprising Recombinant Antigens

The polypeptides may comprise immunogenic compositions and vaccines. In certain embodiments, a polypeptide antigen may correspond to a protein that is essential for virulence or infectivity of rotavirus. Hence, such strains and polypeptides may be used as part of an immunogenic composition or vaccine, for example, formulated in a pharmaceutically acceptable carrier, to prevent rotavirus infection or disease. Such immunogenic compositions or vaccines may further comprise other known rotavirus vaccines or combinations of polypeptides of the present invention. Combinations of various of the above-described polypeptide antigens may comprise a subject vaccine or immunogenic composition, i.e. comprise a "cocktail" of antigens. For example, a subject vaccine or immunogenic composition may comprise VP8* and/or VP5* antigens from multiple rotavirus strains, such as RRV, DS-1 and KU.

In certain embodiments such compositions are used for immunization against rotavirus.

A polypeptide of the invention may be used as an antigen for vaccination of a host to produce specific antibodies which protect against invasion of rotavirus, for example by blocking entry of the virus. In certain embodiments, a vaccine comprises an immunoprotective and non-toxic amount of an antigen of the invention. Purified or partially purified antigenic polypeptides or fragments thereof may be formulated as a vaccine or immunogenic composition. In general, the amount of polypeptide present in a dose (or produced in situ by the DNA in a dose as described in the next section) ranges from about 1 pg to about 100 mg per kg of host, typically from about 10 pg to about 1 mg, and preferably from about 100 pg to about 1 μg. Suitable dose range will vary with the size of the patient, but will typically range from about 0.1 mL to about 5 mL.

Determination of an effective amount of the strain or polypeptide for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or strains of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of polypeptide or strain that, when administered as described above, is capable of raising an immune response in an immunized patient sufficient to protect the patient from rotavirus infection for at least 1-2 years.

Such compositions may also include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, or Bortadella pertussis. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, Al(OH)$_3$ and CpG oligonucleotide (WO96/02555).

In the vaccines of the present invention, the adjuvant may induce an immune response comprising Th1 aspects. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and may comprise a formulation.

2. Immunogenic Compositions and Vaccines Comprising Nucleic Acids

Nucleic acids of the invention encoding immunogenic polypeptides and fragments thereof, may comprise also immunogenic compositions and vaccines.

In one embodiment, the subject nucleic acids may be used to form nucleic acid vaccines, e.g., DNA vaccines, for immunization against rotavirus. DNA vaccination presents a number of features of potential value. Multiple antigens may included simultaneously in the vaccination. Such vaccination may work even in the presence of maternal antibodies.

The use of a nucleic acid of the invention in genetic immunization may employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol. Chem. 1989: 264, 16985), coprecipitation of DNA with calcium phosphate (Benvenisty & Reshef, PNAS USA, 1986: 83, 9551), encapsulation of DNA in various forms of liposomes (Kaneda et al., Science 1989: 243, 375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81, 5849).

DNA vaccination may be applied to eliminate or ameliorate existing disease or conditions, including chronic infectious diseases. For instance, the subject DNA vaccines may be used for immunizing subjects against such infections as rotavirus.

The goal of vaccination is the induction of protective immunity. The target was once limited to infectious diseases, but has now broadened to include treatment of tumors, allergy, and even autoinmune diseases. The delivery of naked plasmid DNA results in the expression of the encoded antigen by muscle cells, and perhaps APCs, resulting in the induction of protective CTLs as well as antibody responses. This method of "genetic immunization" with polynucleic acid vaccines (PNV) may represent a significant advance in vaccination technology because it may be used repeatedly to immunize to different antigens while avoiding the risk of an infectious virus and the problem of the immune response to the vector.

DNA vaccination using the nucleic acids of the present invention may produce different results from other vaccination efforts using DNA, such as naked injection of DNA. The pattern of antigen express, both temporally and spatially, may differ from naked injection of DNA.

The nucleic acids of the present invention may be used to deliver a coding sequence for an antigen(s) as part of a genetic immunization protocol. U.S. Pat. No. 5,783,567 and WO 94/04171 present a number of potential polypeptide sequences for inducing an immunogenic response.

As described in the appended examples, the subject nucleic acids may elicit a strong immune response even at low dose. The choice of components with which the nucleic acids are formulated, along with selection of regulatory elements, may be used to optimize the vaccine response. For example, the material in which the nucleic acid or other material is incorporated may serve as an adjuvant. Additional adjuvants may be administered, for example, within the composition or in conjunction with the composition to enhance the inherent adjuvant effect of the compositions By controlling the rate of release of the sequence giving rise to the antigen, it may be possible to prepare a single dose vaccine to replace a vaccination protocol requiring an initial vaccination followed by booster doses.

In another aspect of the present invention, a variety of DNA vaccination techniques may be employed to elicit a stronger immune response. For example, in certain embodiments, a naked nucleic acid, such as DNA, may be administered along with a composition of the present invention loaded with the same nucleic acid or, alternatively, a different nucleic acid or acids (as well as possibly other materials). In this example, the initial dose of naked nucleic acid followed by release of nucleic acid from the composition may result in a more effective vaccination.

In one embodiment, the subject method may be used as part of a vaccination against microbial pathogens. A major obstacle to the development of vaccines against viruses and bacteria, particularly those with multiple serotypes or a high rate of mutation, against which elicitation of neutralizing antibodies and/or protective cell-mediated immune responses is desirable, is the diversity of the external proteins among different isolates or strains. Since cytotoxic T-lymphocytes (CTLs) in both mice and humans are capable of recognizing epitopes derived from conserved internal viral proteins (Yewdell et al., *PNAS* 82:1785 (1985); Townsend, et al., *Cell* 44:959 (1986); McMichael et al., *J. Gen. Virol.* 67:719 (1986)); Bastin et al., *J. Exp. Med.* 165:1508 (1987); Townsend et al., *Annu. Rev. Immunol.* 7:601 (1989)), and are thought to be important in the immune response against viruses (Lin et al., *J. Exp. Med.* 154:225 (1981); Gardner et al., *Eur. J. Immunol.* 4:68 (1974); Taylor et al., *Immunol.* 58:417 (1986)), efforts have been directed towards the development of CTL vaccines capable of providing heterologous protection against different viral strains.

Those skilled in the art will recognize appropriate epitopes for use generating an immunizing form of the subject nucleic acids. It is known that CTLs kill virally- or bacterially-infected cells when their T cell receptors recognize foreign peptides associated with MHC class I and/or class II molecules. These peptides may be derived from endogenously synthesized foreign proteins, regardless of the protein's location or function within the pathogen. By recognition of epitopes from conserved proteins, CTLs may provide heterologous protection. In the case of intracellular bacteria, proteins secreted by or released from the bacteria are processed and presented by MHC class I and II molecules, thereby generating T-cell responses that may play a role in reducing or eliminating infection.

In an exemplary embodiment, the subject method may be used to produce a protective vaccination against infection by rotavirus. Genes encoding rotavirus proteins may cloned into eukaryotic expression vectors, and formulated for expression of the encoded proteins in mammalian muscle cells in vivo.

In another embodiment of the present invention, DNA vaccination may use mucosal delivery, which allows for easy administration, reduced side-effects, and the possibility of frequent boosting without requiring trained medical personnel. Mucosal delivery of vaccines appears to be the only effective means of inducing immune responses in the mucosal secretions. In addition, many pathogens enter the body through the mucosal tissues of the gut or the respiratory or genital tracts 3. Compositions Formulations containing a polypeptide or nucleic acid may be administered to a subject per se or in the form of a pharmaceutical or therapeutic composition. Pharmaceutical compositions comprising the proteins may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the polypeptides into preparations which can be used pharmaceutically. Pharmaceutically acceptable carriers, suitable neutralizing buffers, and suitable delivering systems can be selected by the person skilled in the art. Proper formulation is dependent upon the route of administration chosen.

The mode of administration of the vaccines of the present invention may be any suitable route which delivers an immunoprotective amount of the vaccine to the subject. However, the vaccine is most commonly administered orally or intranasally.

For topical administration, the polypeptides may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the polypeptides may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the polypeptides with pharmaceutically acceptable carriers well known in the art. Such carriers enable the polypeptides to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the polypeptides for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

The polypeptides may also be formulated in rectal or vaginal compositions such as suppositories or retention enemas, e.g., containing conventional suppository bases such as cocoa butter or other glycerides.

In addition to the formulations described previously, the polypeptides may also be formulated as a depot preparation. Such long acting formulations may be administered by implantation (for example subcutaneously or intramuscularly) or by intramuscular injection. Thus, for example, the polypeptides may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. For example, liposomes and emulsions are well known examples of delivery vehicles that may be used to deliver an antigen. Certain organic solvents such as dimethylsulfoxide also may be employed, although usually at the cost of greater toxicity. The strains or polypeptides may also be encapsulated in microspheres (U.S. Pat. Nos. 5,407,609; 5,853,763; 5,814,344 and 5,820,883). Additionally, they may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the material for a few weeks up to over 100 days. Depending on the chemical nature and the biological stability of the reagent, additional strategies for stabilization may be employed.

4. Methods of Use

The above-described immunogenic compositions and vaccines of the present invention may be used in methods of treating or preventing rotavirus in mammals, for example, humans. In certain embodiments, a method for eliciting an immunogenic response in a mammal may comprise administering to a mammal an effective amount of a rotavirus strain of the invention. In other embodiments, a method for eliciting an immunogenic response in a mammal may comprise administering to an subject at least one polypeptide or antigenically active fragment thereof. In other embodiments, a method for eliciting an immunogenic response in a mammal may comprise administering to an subject a nucleic acid encoding at least one antigenically active gene product, for example a polypeptide or antigenically active fragment thereof. In embodiments where a nucleic acid is administered, the nucleic acid sequence may be comprised of DNA or RNA, and may optionally comprise a vector. In certain embodiments, such methods may comprise a method of treating rotavirus.

In other embodiments, the above-described methods may further serve to vaccinate said mammal rather than simply elicit an immunogenic response. Accordingly, a method for vaccinating a mammal against rotavirus may comprise in certain embodiments administering to an subject at least one polypeptide or antigenically active fragment thereof. In other embodiments, a method for vaccinating a mammal against rotavirus comprises administering to an subject a nucleic acid encoding at least one antigenically active gene product. In embodiments where a nucleic acid is administered, the nucleic acid sequence may be comprised of DNA or RNA, and may optionally comprise a vector. Such methods may elicit an immunogenic response that leads to protective immunity. In certain embodiments, such methods may comprise a method of treating rotavirus.

G. Kits

In other embodiments, the invention contemplates kits including the subject nucleic acids, polypeptides, and other subject materials, and optionally instructions for their use. Kits comprising the pharmaceutical compositions of the present invention are also within the scope of the invention. The compositions may be pharmaceutical compositions comprising a pharmaceutically acceptable excipient. In other embodiments involving kits, this invention contemplates a kit including compositions of the present invention, and optionally instructions for their use. Kit components may be packaged for either manual or partially or wholly automated practice of the foregoing methods. Such kits may have a variety of uses, including, for example, imaging, diagnosis, therapy, and other applications.

EXEMPLIFICATION

The invention having been generally described, may be more readily understood by reference to the following examples, which are included merely for purposes of illustration of certain aspects and embodiments of the present invention, and are not intended to limit the invention in any way.

Example 1

Domain Structure of VP4, as Determined by Protease Analysis

Efficient infectivity of rotavirus in cell culture requires trypsin cleavage of VP4 into two fragments, VP5* and VP8*, both of which remain associated with the virion. Activation of rotavirus for membrane interaction and infectivity has been mapped to a specific cleavage after residue R247 of VP4. The VP8* trypsin cleavage product contains the viral hemagglutinin; the VP5* fragment contains an internal hydrophobic region that has been linked to the ability of activated rotavirus virions to permeabilize membranes. VP5* has also been implicated in the binding of sialic acid-independent strains of rotavirus to cells. Both VP8* and VP5* contain the targets of neutralizing antibodies against rotavirus.

Image reconstructions from electron cryomicroscopy of trypsinized rotavirus particles demonstrate that VP4 forms protruding spikes with apparent 2-fold symmetry and lobed heads. An additional portion of VP4 is buried beneath the VP7 shell and interacts extensively with the underlying VP6 layer.

We performed biochemical and biophysical analysis of purified recombinant VP4. The goals of this analysis were to define a protease-triggered, entry-associated conformational change in VP4, to obtain sequence-specific structural data on VP4, and to obtain the biochemical understanding of VP4 required for successful atomic-resolution structural studies.

Gel filtration chromatography and analytical ultracentrifugation demonstrate that purified, recombinant VP4 is a moderately elongated monomer, well behaved in solution. Image reconstructions from electron cryomicroscopy of rotavirus particles alone and complexed with VP4-specific Fabs provide convincing evidence that VP4 forms dimers on trypsinized rotavirus particles. These findings suggest that interactions of clustered VP4 molecules on the virion probably require stabilization either through a molecular rearrangement induced by trypsin cleavage or through interactions with VP6 (middle capsid layer) or VP7 (outer capsid layer).

Arias and coworkers showed that during trypsin activation of virus, VP4 is initially cleaved C-terminal to R241, then to R231 and R247. Enhancement of infectivity is specifically associated with the relatively inefficient cleavage after R247. The other potential trypsin recognition sites on virion-associated VP4 are protected from cleavage. Further evidence for this activation pathway was provided by a mutational analysis in which VP4 cleavage after R247 (but not after R231 or R241) was required for the induction of cell-cell fusion by virus-like particles.

Trypsin cleavage of purified, soluble VP4 is much more extensive. Trypsin whittles 3.3 kD from the N-terminus of VP8* and approximately 30 kD from the C-terminus of VP5*. These findings suggest that the N-terminal 3.3 kD and the C-terminal 30 kD of virion-associated VP4 are sequestered from protease or folded into protease-resistant structures as a direct or indirect consequence of interactions between VP4 and VP6 or VP7.

The most abundant tryptic core of the VP5* region of purified VP4 lacks the entry-associated N-terminus at A248 due to preferential trypsin cleavage after K258. Chymotrypsin digestion of purified VP4 protects the site after K258 and allows subsequent specific trypsin cleavage C-terminal to R247. VP8CT and VP5CT, the products of sequential digestion of purified VP4 with chymotrypsin and trypsin, have the primary structure of the VP4 activation region found on entry-competent virions. Other investigators have found that chymotrypsin cleaves in the activation region of virion-associated VP4, but that this cleavage results in only a transient or minimal increase in infectivity. Subsequent trypsin treatment of chymotrypsin-treated rotavirus results in full enhancement of infectivity.

VP8CT is a homogeneous monomer, which is folded into a relatively detergent-resistant structure and is composed primarily of β-sheets. Reducing SDS-PAGE of un-boiled VP5CT indicates that it forms stable, SDS- and β-mercaptoethanol-resistant oligomers.

In contrast to VP5CT produced proteolytically, VP5CT expressed directly as a glutathione S-tranferase (GST)-tagged fusion protein in bacteria or as a histidine-tagged fusion protein in insect cells or bacteria is insoluble. Proteolytic removal of the GST tag did not yield soluble VP5CT. Other investigators have found that directly expressed VP5* constructs are mainly insoluble (personal communication, Erich Mackow), but that they selectively permeabilize liposomes.

The protease analysis of purified VP4 defines structural domains that match previously defined functional regions. VP8CT contains the mapped VP8*-specific neutralizing antibody escape mutations, the minimal VP8* antigenic peptide, and the hemagglutination region. VP5CT contains the hydrophobic region associated with membrane interaction, the mapped VP5*-specific neutralization escape mutations, the minimal VP5* antigenic peptide, and a short heptad repeat region.

The results of the studies described above define the basic biochemistry of the VP4. They show it to be soluble and relatively efficiently produced in insect cells. The protease analysis shows that purified VP4 in solution is unstable—about half its structure is degraded by trypsin and chymotrypsin. This protease sensitivity limits its utility as a vaccine component. The protease digestion also defines two structural domains of VP4-VP5CT and VP8CT. These two domains contain all neutralizing epitopes known on VP4. They are both stable and protease resistant. Thus, they would make good antigens for inclusion in a vaccine were it not for the inefficiency of their production by serial proteolysis from an intact purified VP4 precursor, with a yield of approximately 150 µg of each purified fragment per liter of starting cell culture after a 4 column prep and serial protease digestion. VP8CT and VP5CT are excellent targets for structural analysis. The protease-triggered oligomerization of VP5CT provides an in vitro model for rearrangements in VP4 during cell entry.

Example 2

Direct Expression of VP8CT in Bacteria Yielding an Efficiently Produced, Soluble Protein The majority of neutralizing monoclonal antibodies (mAbs) that recognize VP4 of hemagglutinating rotavirus strains select mutations in VP8*. Several of these mAbs block cell attachment. In contrast, the majority of neutralizing mAbs that recognize VP4 of sialic acid independent human rotavirus strains select mutations in the VP5* fragment. As VP8*-specific neutralizing antibodies show limited cross-neutralization among rotavirus strains, VP8* is the main determinant of rotavirus "P" serotype. VP8* may also have intracellular functions in virus replication, as it has been shown to activate cell signaling pathways upon binding to TRAFs (tumor necrosis factor receptor associated factors).

Constructs.

To construct plasmid pGex-VP8$_{46-231}$, the nucleotide sequence encoding residues A46 to R231 of RRV VP4 was amplified by PCR from plasmid pRRV-4, which contains a previously described clone of RRV gene segment 4. The amplified sequence was subcloned into pGex 4T-1 (Amersham-Pharmacia Biotech) to create an in-frame fusion downstream of GST.

Protein Expression and Purification.

E. coli, strain BL21 DE3, transformed with the plasmid described above, was grown at 37° C. to an $A_{600}$ of 0.6 in LB medium supplemented with 100 µg/ml of ampicillin. The cultures were then incubated at 25° C. and, after one hour, were induced with 1 mM isopropyl-β-D-thiogalactopyranoside. Cells were harvested by pelleting 4 hours after induction and frozen.

Frozen cell pellets were thawed in 20 mM Tris, pH 8.0, 100 mM NaCl, 1 mM EDTA (TNE), supplemented with 1% Triton X-100 and 1 mM phenylmethylsulfonyl fluoride (PMSF). The suspension was sonicated and centrifuged at 235,400×g for 2 hrs. The supernatant was passed over a glutathione sepharose column (Amersham Pharmacia Biotech), which was then washed with 20 mM Tris, pH 8.0, 100 mM NaCl, 1 mM CaCl$_2$ (TNC) and digested with 5 µg/ml TPCK-treated trypsin (Worthington Biochemical) for 2 hrs. at room temperature. The cleaved protein was eluted with TNC, the eluate was passed over benzamidine sepharose (Amersham Pharmacia Biotech), and 1 mM PMSF and 2.5 mM benzamidine were added. The protein was then concentrated by ultrafiltration using a Centricon 10 unit and subjected to size exclusion chromatography over a Superdex 200 Hi-Load 16/60 column (Amersham-Pharmacia Biotech) equilibrated in 20 mM NaPO$_4$, pH 7.0, 100 mM NaCl (for NMR studies) or TNE (for crystallographic studies), using an FPLC system (Amersham-Pharmacia Biotech). The concentration of pooled fractions was estimated by $A_{280}$. During purification of selenomethionine-substituted protein, 5 to 10 mM DTT was included in all buffers. The purified proteins were analyzed by MALDI time-of-flight mass spectrometry and N-terminal sequencing (done by the Tufts Core Protein Chemistry Facility) and by dynamic laser light scattering, using a DynaPro 801 instrument (Protein Solutions, Inc.).

Biochemical Results.

A previous biochemical analysis of purified, recombinant RRV VP4 (see EXAMPLE 1) demonstrated that the VP8* region of VP4 contains a compact and homogeneous protease-resistant core from residues A46 to R231. This core contains all mapped antigenic sites on VP8*, the hypervariable region (residues T72 to C203), and the hemagglutination region (residues V93-1208). Because the VP8* core is monomeric, purified preparations do not hemagglutinate. E. coli expression of a construct equivalent to this core (EcVP8$_{46-231}$) produces a high yield of purified protein (approximately 20 mg per liter of starting culture) after a simple two-column preparative procedure. EcVP8$_{46-231}$ is highly soluble (to greater than 65 mg/ml) and monodisperse (polydispersity 9.5% for a 3 mg/ml solution by dynamic laser light scattering). It produces a single peak by mass spectrometry and by gel filtration chromatography. Although EcVP8$_{46-231}$ does not crystallize, it produces good NMR spectra. It is highly protease resistant, being eluted from a glutathione affinity column by trypsin digestion. Thus, an optimized VP8* core produced in bacteria might be a practical component of a rotavirus vaccine.

Example 3

Structures of RRV VP8* Core as Determined by NMR Spectroscopy and X-ray Crystallography and Initial Optimization of the VP8* Core Antigen Structure Description. NMR and X-ray analyses revealed the same basic protein structure. The rotavirus VP8* core is a single, compactly folded, globular domain with dimensions of 36.6 Å by 37.7 Å by 28.3 Å, as measured on a Cα trace. Although there is a two-fold rotational symmetry axis in space group P41212, the two-fold crystal contact (centered around residues A89, E109, P110, W138, and K163) does not suggest a stable dimeric interaction. The NMR spectra contain no NOE cross peaks that would come from a dimer in solution. The VP8* core contains two cysteines (C203 and C216), but they do not form a disulfide bond in the folded structure. Prolines 68 and 182 are in the cis configuration. In addition, there is electron density for two alternate positions of the proline 157 carbonyl, indicating that the crystals contain a mixture of molecules with the G156-P157 peptide bond in either cis or trans.

Figure 3:
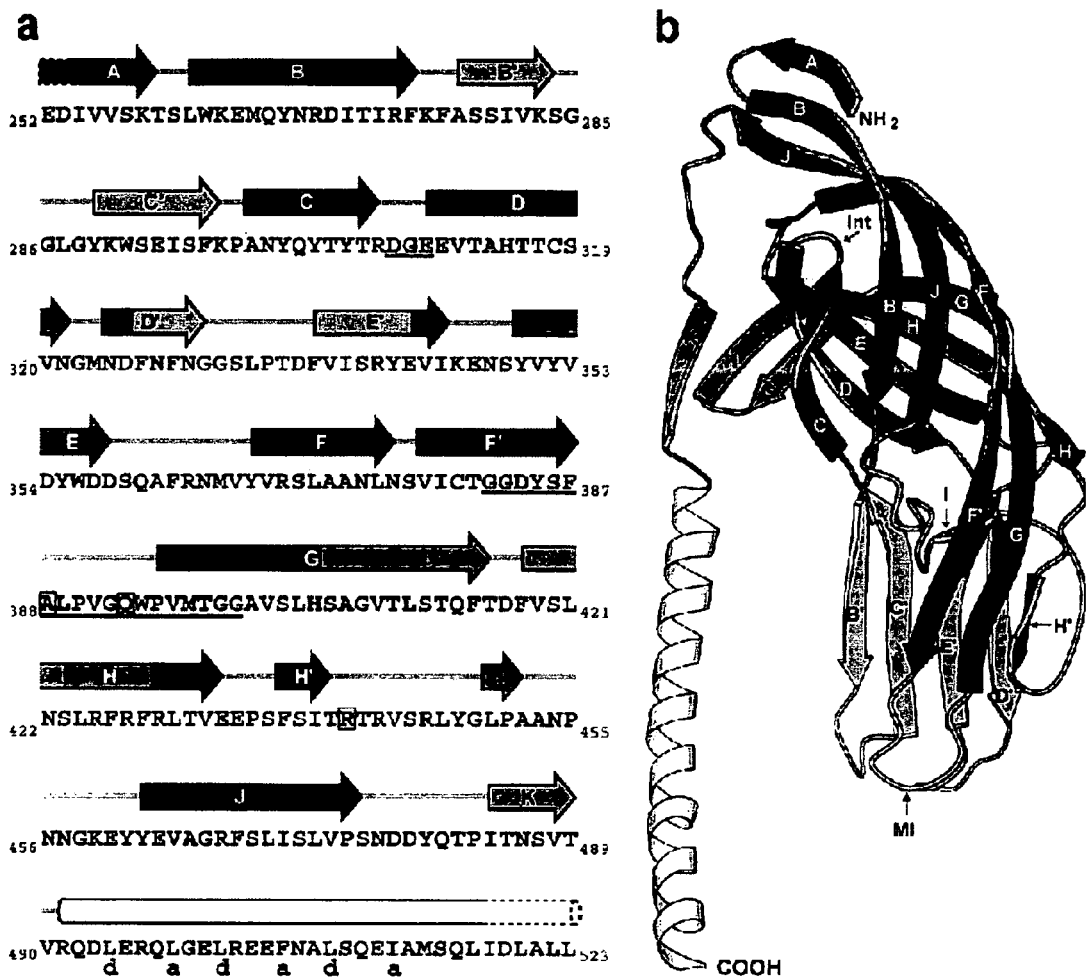
FIG. 3 depicts various views of the VP5CT fold.

The central structural feature of the domain is an eleven-stranded anti-parallel β-sandwich, formed from a five-stranded β-sheet (in blue, strands βM, βB, βI, βJ, and βK) and a six-stranded β-sheet with an interrupted top strand (in green, strands βA, βL, βC, βD, βG, and βH/H'). FIG. 3 shows the alignment of the secondary structure with the amino acid sequence. The two β-sheets are joined by five short inter-sheet loops as well as by a brief stretch of parallel β structure between strand βH' of the six-stranded sheet and βJ of the five-stranded sheet. The cleft between the β-sheets is broad near the carbohydrate binding site but narrows toward the bridging parallel β-strands. The cleft is filled by a dense core of hydrophobic side chains contributed by all strands of the sheets except for βH and βH'. The α-carbons of the N-terminal (L65) and C-terminal (L224) residues are only 10 Å apart. Thus, the VP8* core arises from a narrow attachment to the remainder of the VP4 spike. Indeed, the side chains of L65 and L224 contribute to the same hydrophobic core.

The domain contains three other structural elements. First, the inter-sheet loop connecting strands βK and βL contains a short α-helix (αA). Second, a longer α-helix (αB) at the C-terminus packs against strands βM, βB, βI, and βJ of the five-stranded β-sheet. Third, an extended β-ribbon (strands βE and βF) arises from the loop between strands βD and βG and packs against strands βC, βD, βG, βH, and βH' of the six-stranded β-sheet.

The tight fold of the β-sandwich, the cross bracing of the β-sheets by the β-ribbon and the C-terminal α-helix, the short loops between strands, and the dense hydrophobic cores between the major structural elements suggest a rigid structure that is unlikely to undergo major rearrangements during cell entry. The compact structure accounts for the protease resistance and stability of the VP8* core, which shows no evidence of degradation or denaturation after storage for months at 4° C. in the absence of protease inhibitors. This physical resistance may be an adaptation to the harsh conditions in the gut and the external environment.

Binding-Induced Structural Changes in the VP8* Core.

Comparison of the liganded crystal and unliganded NMR structures shows no evidence for a major conformational rearrangement induced by sialic acid binding. The backbone trace of the crystal structure superimposes on the mean NMR structure with an RMSD of 1.34 Å. For comparison, within the suite of 20 accepted NMR structures, the backbone RMSD is 0.78 Å.

There is, however, evidence that sialoside binding causes local changes in the VP8* core. Specifically, the cleft above which the sialoside binds is slightly narrowed in the crystal structure relative to the NMR structure. In the triple resonance NMR spectra, the S190 backbone peaks are missing, and the T191 backbone peaks have two alternate amide proton chemical shifts, suggesting flexibility in the absence of ligand (and preventing accurate T2 relaxation measurements). In the crystal structure, S1190 and T191 have well-defined electron density and low thermal parameters (7.3 for S190 atom N, and 8.7 for T191 atom N), indicating that their conformation is stabilized in the presence of ligand. The network of hydrogen bonds between the sialoside glycerol and carboxylate groups and residues R101, Y155, and S190 is probably responsible for this stabilization. These findings suggest a binding-induced fit of the sialoside and its recognition site.

Fit to an Electron Cryomicroscopy Reconstruction.

The sialic acid binding domain fits size and shape of the "heads" of the rotavirus spike, as seen in an electron cryomicroscopy-based reconstruction. Like the VP8* core, the heads make no dimeric contacts. The placement of the crystal structure buries the highly conserved region near the N- and C-termini (see below) and exposes the sialic acid binding site and the widely distributed neutralizing antibody escape mutations. This positioning is also consistent with an image reconstruction of trypsinized particles decorated with mAb 7A12. A precise orientation of the sialic acid binding domain within the head can not be determined, however, because of its globular shape and the 26 Å resolution of the map.

The identification of residues L65-L224 as the "heads" of the VP4 spike indicates that the first 64 residues of VP8* form a part of the "stalk," interacting with VP5*. It is, therefore, likely that non-covalent interactions of these N-terminal residues (and possibly P225-R231) with VP5* link authentic VP8* to the virion after trypsin activation. This placement also indicates that the trypsin activation region (R231-R247) must be near the junction of the head and the stalk. Antibody decoration experiments locate the membrane interaction motif of VP5* at the top of the stalk, near this junction. This placement suggests that trypsin cleavage may permit an unmasking of the membrane interaction motif. As the N- and C-termini of the VP8* core are separated by only 10 Å and are located in a prominence with a strong negative charge, the connection between head and stalk may be flexible.

Antigenic Surfaces.

The antigenic topography of VP8* has been investigated extensively because antibodies against VP8* can both neutralize virus and protect experimental animals from disease. Neutralization escape mutant analyses have provided sequence-specific data that allow correlation of antigenic maps of the VP8* core with its structure. None of the twenty mutated residues listed in Table I is located in the center of a β-sheet. Five escape mutations map to residues with evidence for significant flexibility (residues Q135, Q148, G150, E180, and S190), but the other fifteen selected residues are relatively inflexible.

Antibody competition experiments and escape mutant analyses indicate that VP8* contains several interrelated epitopes recognized by neutralizing antibodies. Neutralization escape mutations against hemagglutinating strains are widely distributed across the accessible surface of the VP8* core, but do show clustering. We call the clusters epitopes 8-1, 8-2, 8-3, and 8-4. Antibody competition experiments and analysis of the cross-resistance of variants, while reflecting this clustering, also show some competition between antibodies located in different epitopes. For example, mAb 954/23, which selects a mutation in epitope 8-1 at residue 194 competes for binding with mAbs that select mutations in epitopes 8-2 and 8-3 at residues 136, 180, and 183.

Epitope 8-1 is located near the bound sialic acid and the positions of proximal sugar residues in an oligosaccharide side chain. Some antibodies that select mutations at residues in this epitope interfere with early entry events. For example, mAbs that select escape mutations at residues 100, 148, and 188 block binding to cells; a S190 to L escape mutant no longer hemagglutinates; and infection by a G150 to D escape mutant is no longer sensitive to neuraminidase digestion of cells.

Epitope 8-2 is defined by mutations selected at residues E180 and N183 by mAbs that destabilize the outer capsid of the virion. The residues from G179 to V184, which include the βJ-βK loop, make key contacts, participating in the parallel β-strands (βJ and βH') that link the five-stranded and six-stranded β-sheets and forming hydrogen bonds with Q137 in the βF-βG loop, T161 in the βH'-βI loop, and N221 near the C-terminus of αB. Antibody binding may disrupt these interactions, and transmission of the resulting distortions to the remainder of the spike through the domain's C-terminus may result in the observed outer capsid destabilization.

Residues in epitope 8-3 are located in the β-ribbon and the loops that connect the β-ribbon to the 6-stranded β-sheet. A number of IgA monoclonals map to this epitope. Although some escape mutations in epitope 8-3 are located close to those in epitope 8-2, antibodies that select these mutations do not destabilize the outer capsid, and their mechanism of neutralization has not been determined.

Epitope 8-4 consists of three adjacent residues on the βB-βC loop, which connects the two β-sheets. It is predicted to lie on an accessible surface at the edge of the cleft between the two "heads" of the spike. A mechanism of neutralization has not been determined for mAbs mapping to this epitope.

Although a number of neutralizing mAbs map to VP5* from sialic acid-independent human rotavirus strains, only three neutralizing mAbs have been mapped to VP8* of such strains. One such VP8*-specific mAb selects a mutation at residue 148 in epitope 8-1, demonstrating that interference with sialic acid binding is not the sole mechanism of neutralization for epitope 8-1 mAbs. The other two mAbs select mutations at residues 72 and 217, which are located outside the known neutralization epitopes of sialic acid-dependent strains and are remote from the sialic acid binding site. The paucity of neutralizing mAbs against VP8* of sialic acid-independent strains and the separate locations of these two escape mutations suggest that there are substantially different roles for VP8* from sialic acid-independent and sialic acid-dependent strains in early entry events.

TABLE 1

Neutralization Escape Mutations on the VP8* Core

| Residue[a] | Mutation | Epitope[b] | Strain[c] | Antibody | Comment[d] |
|---|---|---|---|---|---|
| 72 | T to I | NA | ST3 | HS6 | neutralizes human strain |
| 87 | T to A | 8-4 | RRV | M11 | |
| 88 | T to L | 8-4 | RRV | A1 | |
| 89 | A to P | 8-4 | RRV | A15 | |
| 100 | D to N | 8-1 | RRV | 1A9 | blocks binding |
| 114 | S to F | 8-3 | RRV | 5D9 | |
| 116 | E to D | 8-3 | C486 | 2E8 | |
| 132 | Y to D | 8-3 | RRV | 3G6 | IgA |
| 133 | A to N | 8-3 | RRV | 2A10 | IgA |
| 133 | A to V | 8-3 | RRV | 3F12 | IgA |
| 135 | Q to K | 8-3 | RRV | 4B7 | IgA |
| 135 | Q to R | 8-3 | RRV | 4C2 | IgA |
| 136 | D to N | 8-3 | SA11 cl3 | 9F6 | |
| 146 | Q to R, K, or Y | 8-1 | SA11 4f | Hyper-immune[e] | |
| 148 | Q to R | 8-1 | RRV | 2B12 | IgA |
| 148 | Q to R | 8-1 | RV-5 | RV5:2 | neutralizes human strain |
| 148 | Q to R | 8-1 | RRV | M14 | IgM, blocks binding, passively protects mice |
| 150 | G to E | 8-1 | RRV | 5C4 | V150 is neuraminidase-insensitive |
| 180 | Q to R | 8-2 | SA11 cl3 | 7G6 | destabilizes virus |
| 183 | N to D | 8-2 | SA11 cl3 | 10G6 | destabilizes virus |
| 188 | Y to F | 8-1 | RRV | 7A12 | blocks binding |
| 190 | S to L | 8-1 | RRV | 4B6 | IgA; v4B6 doesn't HA |
| 194 | Y to C | 8-1 | RRV | 954/23 | blocks binding; v194 doesn't HA |
| 217 | E to K | NA | ST3 | HS11 | neutralizes human strain |

[a]Residue numbering is based on the RRV sequence.
[b]"NA" indicates mutations seen only in sialic acid-independent strains and not assigned to an epitope.
[c]Characteristics of these strains are as follows: ST3 is a P[6] human strain; RRV is a P[3] simian strain; C486 is a P[1] bovine strain; SA11 cl3 is a P[2] simian strain; RV-5 is a P[4] human strain; and SA11 4f is a P[1] simian strain.
[d]Monoclonal antibodies are IgG unless otherwise specified. "Binding" refers to binding to cells. "HA" - hemagglutination.
[e]The hyperimmune antiserum to SA11 4f selected mutations at residue 146 in 4/7 variants sequenced, although other mutations were also selected. Mutations at 146 are probably responsible for neutralization escape and are included in the table.

Overall Surface Variability.

VP8* surface residues are highly variable among P genotypes, probably reflecting selection pressure for diversity by the host immune response. The residues around the N- and C-termini form the only surface that is highly conserved. As this surface contains the point of attachment to the remainder of VP4, much of it is probably buried on the complete spike. This surface variability poses a challenge for using the VP8* core as an immunogen and as a target for structure-based drug design: although most human disease is caused by P genotypes 4 and 8, a number of other P genotypes also infect humans, raising the possibility of the early emergence of strains that escape neutralization or resist antivirals.

Summary.

The structure determinations by X-ray crystallography and NMR spectroscopy defined the hemagglutination domain of rotavirus. They showed that the VP8* specific epitopes are present on this single, compactly folded domain. The NMR structure allowed the refinement of the boundaries of the domain, allowing a trimmed version that crystallized in the presence of a simple sialoside.

Example 4

X-Ray Crystallographic Determination of the Structures of VP8* Cores from Virulent Human Rotaviruses and from RRV in the Absence of Sialic Acid and Further Optimization of the VP8* Core The molecular apparatus that mediates cell entry by rotavirus is a promising target for vaccine development. There are major gaps, however, in our understanding of the entry pathway of this virus. Sialic acid-dependent strains of rotavirus, which include many of those that cause disease in non-human animals, initially attach to the host cell by binding cell-surface sialic acid. This binding is presumably followed by subsequent interactions with downstream receptors on the cell surface, leading to membrane penetration by the virus. Most strains of rotavirus that cause disease in humans, on the other hand, are sialic acid-independent and do not require cell-surface sialic acid for efficient infectivity. These strains of the virus likely bind to the host cell initially through a second receptor on the cell surface, possibly a shared receptor with the sialic acid-dependent strains. Sialic acid is a common initial attachment molecule for many different viruses and has been implicated in determining viral host range and infection efficiency. Sialic acid binding may also act as a trigger for entry-related conformational changes in other viral attachment proteins.

Beyond initial cell-surface attachment, the role of sialic acid binding by rotavirus is unclear. The identity of cell-surface receptors downstream of sialic acid remains controversial, although some evidence suggests that VP5* binds to an integrin or a heat shock-associated protein. While rotavirus sialoside specificity is broader than that of influenza or polyomavirus, the rhesus rotavirus strain (RRV) binds N-acetyl neuraminic acid with approximately 10 times its affinity for N-glycolyl neuraminic acid. Less quantitative assays have suggested that other strains of rotavirus may preferentially bind N-glycolyl neuraminic acid. The preference of some sialic acid-dependent strains for the N-glycolyl variant of sialic acid could partly explain the sialic acid independence of most rotavirus strains that infect humans, since humans differ from other animals in failing to synthesize N-glycolyl from N-acetyl neuraminic acid. Sialic acid binding also determines the polarization of rotavirus entry at the apical versus basolateral membranes of polarized epithelial cells. While sialic acid-independent strains can infect through either membrane, sialic acid-dependent strains can only infect at the apical surface. Although no direct evidence exists that sialic acid binding by rotavirus VP8* triggers subsequent conformational changes or other downstream events in rotavirus entry, some neutralizing antibodies that bind to VP8* have been shown to cause disassembly of triple-layered viral particles. This result suggests a possible role for VP8* in triggering conformational changes that lead to uncoating of the virus during the natural process of cell entry.

While many rotavirus strains require sialic acid (SA) on the cell surface for entry, most strains that cause human disease do not. Conventional genetic studies of SA-independent mutants of rotavirus suggest that SA-binding may trigger an entry-related molecular event, possibly a rearrangement to trigger membrane penetration. Therefore, understanding the role of sialic acid in entry is relevant to understanding entry by all rotavirus strains. We have crystallized the VP8* core from a sialic acid-independent virulent human rotavirus strain (DS-1) and from a sialic acid-independent mutant of a normally sialic acid-dependent strain (RRV). X-ray analysis of these crystals reveals reflections to at least 1.5 Å resolution and will allow molecular replacement structure determinations.

VP8CT can be efficiently expressed as a soluble recombinant protein in *E. coli* Initial structure determination by nuclear magnetic resonance spectroscopy (NMR) and an NMR carbohydrate binding analysis showed that a monosaccharide sialoside is its minimal carbohydrate ligand. Based on the NMR solution structure, a second recombinant construct with trimmed termini was expressed. This protein, the VP8* core (residues 62-224), crystallized in complex with the simple sialoside, permitting a structure determination by X-ray crystallography at 1.4 Å resolution (see EXAMPLE 3).

The structure reveals details of the molecular surfaces recognized by neutralizing and protective antibodies against VP8* (epitopes 8-1 to 8-4). The neutralizing epitopes of VP8* are formed by a tightly folded structure. Moreover, the VP8* core is a single, compact domain, the minimal structure that can be expected to fold into the molecular surfaces recognized by neutralizing antibodies. Comparison to electron cryomicroscopy image reconstructions of trypsin-cleaved virions reveals that the VP8* core forms the "heads" of the VP4 spikes. This compact target for protective immunity can be efficiently purified from *E. coli* lysates by affinity and gel filtration chromatography, with current yields of 20 mg of pure antigen per liter of bacterial culture. The VP8* core is soluble to greater than 65 mg/ml. It is very stable, with protein stored for more than 6 months at 4° C. showing no signs of degradation or denaturation by SDS-PAGE or by 2D NMR spectroscopy. These properties are not specific to VP8* cores from RRV. An equivalent VP8* core from a virulent human rotavirus stain, DS-1, shares all basic biochemical characteristics tested thus far. We have determined the structure of the DS-1 VP8* core. Despite lacking sialic acid binding activity, the DS-1 VP8* core has the same basic structure as the RRV VP8* core. Thus, structural and biochemical analysis of VP4 has allowed the engineering of a potential immunogen with outstanding biochemical characteristics for a component of a subunit vaccine.

Crystal Structure of Unliganded Wild Type RRV VP8*.
Optimization of the VP8* Core for Crystallization.

During purification the VP8* core is separated from an N-terminal GST tag by trypsin digestion. Trypsin cleavage prior to residue 62 of a VP8* construct containing residues 62-224 was inefficient and resulted in an N-terminal leader of 19 disordered residues on the purified protein. The known crystal structure of the VP8* core in complex with sialic acid indicates that L65 is the first ordered residue. Crystallization in the absence of sialic acid ligand is most likely to be successful with a homogeneous product containing a minimal disordered leader. Therefore, the VP8* construct was optimized for efficient cleavage at the N-terminus of the core protein. New primers were designed with a potential trypsin cleavage site (an arginine residue) just N-terminal to the VP8* coding sequence, beginning with either residue 60 or residue 58 (5pVP8 60-224, 5pVP8 58-224). This strategy improves accessibility of the trypsin cleavage site by increasing the number of residues between the arginine and the first ordered residue (L65) of the compact VP8* core.

The new N-terminal primers were used with primer 3pVP8 62-224 to amplify VP8* residues 60-224 and VP8* residues 58-224 from an existing RRV VP4 construct and subclone them into the GST-tagged expression vector pGex 4T-1. The proteins were expressed in *E. coli* and purified as described above. For one liter of bacterial culture, this procedure yielded 12-16 mg of the purified proteins, which were extraordinarily soluble, remaining in solution at concentrations greater than 80-100 mg/mL. Mass spectrometry and N-terminal sequencing of the trypsinized products revealed that both proteins were cut cleanly from GST at the intended trypsin cleavage site. The VP8* 60-224 construct contains the shortest leader, with 5 residues N-terminal to the ordered L65, and was therefore selected for crystallization screening.

Comparison of Wild Type VP8* Structures in the Presence and Absence of Sialoside.

An overlay of Cα traces from the unbound VP8* core and the previously-determined structure of VP8* in complex with sialic acid shows that. these backbone structures are very similar overall, but some subtle conformational changes can be seen. In the sialic acid-bound structure, the sialic acid-binding cleft is narrower than in the unbound structure by about 1.5 Å between backbone atoms of β-strands bordering the cleft. This narrowing is most significant at the open end of the cleft due to a shift in position of the prominent loop forming the upper cleft wall. This shift, for Cα atoms of the loop, is about 1.7 Å maximum. The displacement of this loop, combined with a small shift in the β-ribbon, also causes an adjacent cleft between the loop and the β-ribbon to widen upon sialoside binding by about 2.3 Å backbone-to-backbone. In addition, a second loop, which connects the six-stranded β-sheet to the β-ribbon, has a minor shift upon binding of about 1.0 Å maximum for Cα atoms.

Narrowing of the sialic acid-binding cleft is associated with the formation of a hydrogen bond across this cleft between a strand of the six-stranded β-sheet and a strand of the five-stranded β-sheet, at the end of the cleft neighboring the prominent shifted loop. The side chain atom OD1 of residue D100 and the backbone amide of residue T192 move from 4.37 Å apart in the unliganded structure to a hydrogen bonding distance of 3.22 Å in the liganded structure. At the other end of the sialic acid-binding cleft, the peptide bond between residues G156 and P157 is in the cis conformation in the unliganded VP8* structure, but has both cis and trans alternative conformations in the sialoside-bound structure. In addition, the side chain of residue K187 becomes more ordered upon sialic acid binding, and its electron density reaches across the cleft toward residue G156 in the liganded structure.

Widening of the second cleft, adjacent to the sialic acid-binding cleft, is associated with the disruption of two water bridges that are present between the six-stranded β-sheet and the β-ribbon. The enlargement of this cleft exposes a pocket of hydrophobic residues. Surface models of the full VP8* core with and without bound sialoside demonstrate the effect of this change on the structure of the VP8* surface that faces toward a target cell. In these images, it is apparent that the second cleft forms a significantly wider groove in the VP8* surface of the sialic acid-bound structure than in the surface of the unliganded structure.

Discussion.

Comparison of the structures of RRV VP8* in the presence and absence of sialic acid reveals no major structural rearrangements in this hemagglutination domain of the VP4 spike upon sialic acid binding. Some subtle conformational changes are observed, however, particularly in the sialic acid-binding cleft and an adjacent cleft bordered by the β-ribbon. Although these shifts are on the order of 1 to 2 angstroms, the high-resolution structures (1.2 Å and 1.5 Å) allow such changes to be measured accurately.

It is difficult to see how these subtle changes could be transmitted directly to the rest of the spike, since the points of attachment between the VP8* core and the rest of VP4, including the N- and C-termini of the core, do not shift significantly. However, the changes associated with sialic acid binding may contribute to other downstream events in the rotavirus entry pathway. Specifically, the widening of a second cleft adjacent to the sialic acid-binding cleft suggests the hypothesis that VP8* binds another ligand in this cleft. It is possible that sialic acid binding by sialic acid-dependent strains of rotavirus could open a binding site for a second cellular receptor involved in the cell entry pathway. The hydrophobic pocket that opens upon sialic acid binding lies on the outward-facing surface of VP8*, orienting this potential binding cleft in an appropriate position to contact proteins on the cell surface.

The possibility that subtle conformational changes in sialic acid-bound VP8* may be important for rotavirus entry is supported by the distribution of conserved residues on the VP8* surface. A surface representation of VP8* colored by the degree of variability in each surface residue over a range of rotavirus strains demonstrates that the potential receptor-binding cleft, adjacent to the sialic acid-binding cleft, contains a particularly high density of the few conserved patches on the VP8* surface, suggesting that residues in this cleft may have conserved functions. Since sialic acid binding increases the solvent exposure of these residues, their conservation across rotavirus strains supports the hypothesis that binding of sialic acid results in functionally-important conformational changes in VP8*.

Many neutralization escape mutations have been mapped to the regions of VP8* that shift upon sialic acid binding. The mechanism of neutralization at some of these epitopes is already understood: antibodies that bind epitope 8-1 can directly interfere with sialic acid binding; and antibodies that bind epitope 8-2 destabilize virions, suggesting that VP8* may play a role in rotavirus uncoating. The mechanism of neutralization for antibodies mapping to epitopes 8-3 and 8-4, however, is currently unknown. Epitope 8-3 maps to the loop connecting to the β-ribbon. This loop shifts upon sialic acid binding. The shift in epitope 8-4 is of similar magnitude to the other shifts (about 0.9 Å). The conformational changes in VP8* described here suggest that antibodies recognizing these epitopes could indirectly block sialic acid binding by interfering with binding-associated conformational changes or could interfere with biologically-important functions of the associated regions of VP8*.

Finally, several sialic acid-independence mutations identified in VP8* (Juan Ludert, personal communication) map to the rims of the two clefts that shift upon sialic acid binding. Two mutations that affect sialic acid independence (D100N and K187R) are in residues that form hydrogen bonds across the sialic acid binding cleft. These mutations could alter the equilibrium between sialic acid-bound and unbound conformations of VP8*. Two other mutations (G150E and Q125R) are unlikely to directly affect sialic acid binding due to their distance from the binding cleft. The side chain of Q125, in particular, is disordered and protrudes into solvent. While this mutation could affect interactions with another ligand, it seems unlikely to affect the internal dynamics of VP8*.

The motions observed upon sialic acid binding, the conservation of residues in the cleft that widens upon binding, and the location of mutations associated with neutralization escape and sialic acid independence together indicate that sialic acid binding-induced conformational changes in VP8* are functionally relevant to rotavirus entry. These results also suggest the hypothesis that sialic acid binding by sialic acid-dependent rotavirus strains is required to open a binding site in VP8* for a downstream cellular receptor.

Crystal Structure of the VP8* Core from a Human Rotavirus Strain.

Generation of VP8* Constructs from Human Strains KU and DS-1.

VP4 clones from human strains KU (genotype P[8]) and DS-1 (genotype P[4]) were obtained as recombinant baculoviruses. DNA was isolated from infected Sf9 insect cells and used as template in PCR reactions to amplify the VP8* regions of each strain. Primers to amplify KU VP8* residues 60-224 were designed based on the available nucleic acid sequence for KU VP4. The KU VP8* 60-224 sequence was therefore amplified directly from the baculovirus DNA and subcloned into the GST-tagged expression vector pGex 4T-1.

Because no nucleic acid sequence was available for the DS-1 strain, full length DS-1 VP4 was initially amplified using primers complementary to sequences in the BlueBac2 vector on either side of the VP4 coding sequence. This purified PCR product was sequenced using the same BlueBac2 primers and provided the 5' DS-1 VP4 cDNA sequence through amino acid residue 130. To obtain the remaining VP8* sequence (up to residue 223 of DS-1 VP4), a forward primer was designed to extend from the coding sequence of residue 130. The resulting sequence allowed primers to the 5' and 3' ends of DS-1 VP8* to be designed, and these were used to amplify residues 60-223 from the baculovirus DNA and subclone them into the GST-tagged expression vector pGex 4T-1.

Both KU and DS-1 VP8* proteins were expressed in *E. coli* and behaved similarly to RRV VP8*. Both proteins were protease resistant and could be purified by the procedure described for RRV. This procedure yielded 8-9 mg of DS-1 VP8* and under 3 mg of KU VP8* from one liter of bacterial culture, and the proteins were concentrated to approximately 60 mg/mL and 20 mg/mL, respectively. Mass spectrometry and N-terminal sequencing of the trypsinized products revealed that both proteins were cut cleanly from GST by trypsin.

Comparison of DS-1 and RRV VP8* Structures.

The backbone structure of the DS-1 VP8* core is similar to that of the RRV VP8* core. The major structural difference between DS-1 VP8* and unliganded RRV VP8* is an expansion of the potential receptor-binding cleft, adjacent to the sialic acid-binding cleft of the RRV strain, in DS-1 VP8*. This widening is primarily the result of a large shift in position of the DS-1 β-ribbon.

DS-1 VP8* Binds an Amino Acid Chain.

In the DS-1 VP8* crystal, the N-terminal leader of each protein extends away from its own core and inserts into the widened cleft, described above, of a neighboring molecule in the crystal. These N-terminal residues form part of a new three-stranded β-sheet, consisting of the inserted strand and the two strands of the β-ribbon bordering the cleft. Five β-sheet-type hydrogen bonds are formed between the backbones of the bound amino acid chain (residues 60, 62, and 64) and the β-ribbon (residues 131, 129, and 127, respectively). The inserted residues are too far from the β-strand lining the opposite wall of the cleft to form additional hydrogen bonds to those residues. A surface representation shows that this bound N-terminal leader fits into a deep cleft in the surface of DS-1 VP8* that results from the shift in the DS-1 β-ribbon mentioned above. In addition, the side chain of leader residue V61 is oriented down into this cleft and inserts into a pocket lined by hydrophobic residues, stabilizing the binding of the N-terminal leader by hydrophobic interactions.

Discussion.

Sialic acid binding by RRV VP8* is accompanied by the widening of one end of a cleft adjacent to the sialic acid-binding cleft. Comparison to the DS-1 VP8* structure described here reveals that this end of the cleft in DS-1 VP8* resembles the widened sialic acid-bound conformation of the cleft in RRV VP8*. The hypothesis that conformational changes associated with sialic acid binding by RRV are functionally important, predicts that the conformation of VP8* from a naturally-occurring sialic acid-independent rotavirus strain should be similar to sialic acid-bound VP8* from the sialic acid-dependent RRV strain. The DS-1 VP8* structure confirms this prediction. This result suggests the hypothesis that the VP8* core from sialic acid-independent strains is primed for downstream entry events that require sialic acid binding by sialic acid-dependent strains.

In fact, the cleft of interest is significantly wider in the DS-1 VP8* core than in either observed RRV VP8* conformation, possibly due to a one-residue deletion in the loop that connects the β-ribbon to the six-stranded β-sheet in DS-1 VP8*. The deletion is seen in VP8* from essentially all known naturally-occurring sialic acid-independent rotavirus strains, suggesting that the widened cleft may be a common characteristic of these strains. This loop shifts in the sialic acid-dependent strain upon sialic acid binding and may contribute to the widening of the potential receptor-binding cleft in RRV VP8*.

In addition, the DS-1 VP8* crystal structure provides direct evidence that the widened cleft is capable of binding a second molecule, since this cleft binds to the N-terminal five residues of a neighboring VP8* molecule in the crystal. A strand from a host cell protein, potentially a second cellular receptor, could bind to this cleft of VP8* in a similar manner. This observation supports the hypothesis that sialic acid binding by sialic acid-dependent rotavirus strains may open a second receptor-binding site. It also suggests that sialic acid-independent rotavirus strains might initially attach to a host cell by binding this hypothesized receptor on the cell surface.

The size of the hydrophobic pocket in the cleft, into which the side chain of leader residue V61 inserts in the crystal, is easily large enough to accommodate a larger hydrophobic side chain, suggesting that tighter binding of a natural ligand is possible through more extensive hydrophobic interactions. In addition, the inserted N-terminal amino acids in the DS-1 VP8* core crystal structure hydrogen bond only to the β-ribbon and not to the opposite strand of the binding cleft. This strand is too far from the inserted residues to form hydrogen bonds, possibly due to the proline (residue 63) of the inserted chain, which props the cleft open. In addition, the number of N-terminal amino acids on the leader that are available for binding is limited, although the cleft continues beyond the N-terminus of the leader. The C-terminal end of the inserted chain is forced out of the cleft to join its own VP8* core. This constraint may also disrupt potential hydrogen bonds between the inserted chain and the opposite cleft wall. If this cleft does bind to a cellular receptor during rotavirus entry, however, the β-strands on either side of the cleft might close slightly to form a continuous β-sheet, with the inserted amino acid chain as an internal strand. These interactions could lead to a tight interaction between VP8* and a specific receptor protein on the cell surface.

The high-resolution structures of variants of the rotavirus VP8* hemagglutination domain presented here reveal that a sialic acid-dependent strain, RRV, undergoes subtle structural changes upon sialic acid binding. In addition, similarities between the VP8* core structure of a sialic acid-independent strain, DS-1, and the bound conformation of the RRV VP8* core support the hypothesis that sialic acid-independent strains of rotavirus are structurally and functionally similar to sialic acid-bound sialic acid-dependent strains. Taken together, these data suggest the hypothesis that sialic acid-independent rotavirus strains initially attach to cells during entry by binding a cellular protein ligand in a potential receptor-binding cleft. Furthermore, in sialic acid-dependent strains, the opening of this cleft upon sialic acid binding may potentiate this subsequent interaction with a cell-surface receptor. The concept of sequential, dependent binding events in viral entry has precedent in the entry of HIV. CD4 binding by HIV gp 120 exposes or creates the binding sites for the second receptors CCR4 and CXCR4.

A first step toward determining whether binding of the N-terminal leader sequence by the DS-1 VP8* protein in the crystal structure models a biologically-important receptor-ligand interaction is to test for this binding in solution. For this test, an NMR binding experiment will be carried out with an $^{15}$N-labeled peptide corresponding to the leader. The N-terminal sequence TVEPV (SEQ ID NO: 5) (residues 60-64) and a similar sequence (TLEPV) (SEQ ID NO: 6) with a larger hydrophobic side chain at the position of residue 61, facing into the DS-1 hydrophobic pocket, have been synthesized as labeled peptides. To limit competition between the peptides and the N-terminal leaders of other DS-1 molecules in solution, I have mutated the leader of DS-1 to a sequence containing only serines and glycines. The modified DS-1 VP8* cores and $^{15}$N-labeled peptides will be used in NMR binding experiments, similar to those described here. Finally, the identity of a possible authentic cellular ligand for the second binding cleft in VP8* will be sought in a phage display experiment. Peptides made from a human intestinal epithelial cDNA library, presented by recombinant bacteriophage, will be screened for binding to the DS-1 VP8* core.

Example 5

Additional Biochemical, X-Ray Crystallographic Structural, and Neutralization Escape Studies of VP8* Cores from Virulent Human Rotaviruses Structural Comparison of the DS-1 and RRV VP8* Cores.

Figure 8:
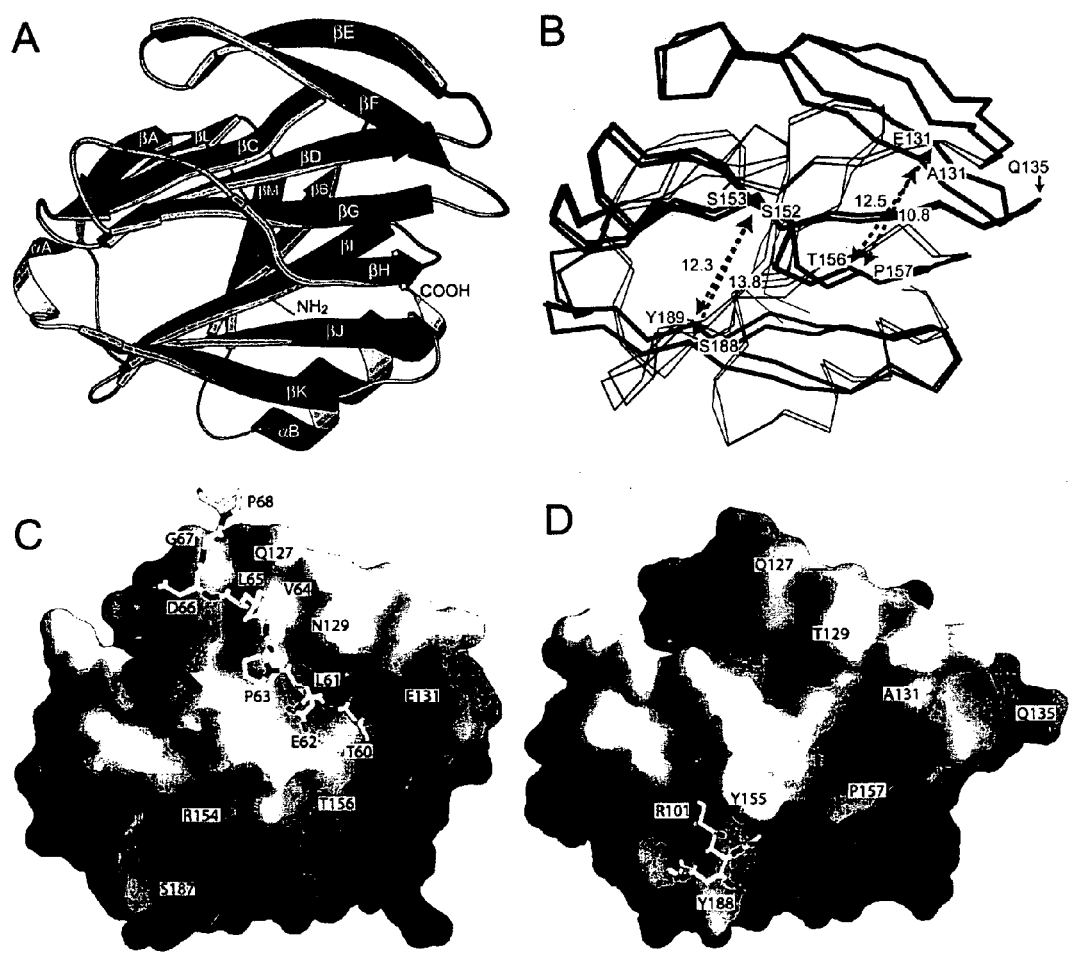
FIG. 8 depicts a comparison of the DS-1 and RRV VP8* cores.

The DS-1 VP8* core crystallizes in space group P1. Using the crystal structure of the RRV VP8* core as an initial phasing model for molecular replacement, we determined the X-ray crystal structure of the DS-1 VP8* core at 1.6 Å resolution. The DS-1 VP8* core has a galectin-like fold, as does the RRV VP8* core (FIG. 8A, B). It is built around a central β-sandwich, with a β-ribbon (EF, red) packed against a six-stranded β-sheet (green) and a C-terminal α-helix packed against a five-stranded β-sheet (blue). Each asymmetric unit contains eight molecules of the DS-1 VP8* core. There are no major conformational differences between the eight molecules, which superimpose on each other with an average RMSD between Cα atoms of 0.256 Å (not shown).

Although the DS-1 and RRV VP8* cores share only 45% amino acid identity (for residues 60-224 of RRV and 60-223 of DS-1), they superimpose on each other with an RMSD of 1.04 Å for 159 equivalent Cα atoms. The broad surface that is formed by EF β-ribbon, strands H and G of the six-stranded β-sheet, and strands J and K of the five-stranded β-sheet is furrowed by two clefts. Both clefts are wider in the DS-1 VP8* core than in the RRV VP8* core. In the DS-1 VP8* core, the architecture of the cleft between the five-stranded and six-stranded β-sheets, which corresponds to the RRV SA binding site, is extensively altered. In the RRV VP8* core, the R101 side chain amide makes key contacts with the sialoside. It projects up from strand D to form a positively charged patch on the floor of the binding site and make bidentate hydrogen bonds to the glycerol group of the bound carbohydrate. In the DS-1 VP8* core, phenylalanine replaces arginine at this site. F101 of DS-1 makes no contribution to the molecular surface, and its aromatic ring forms part of a hydrophobic core in the interface between the β-sheets. In the RRV VP8* core, the aromatic rings of Y155 and Y188 project into solvent to form walls on either side of the sialoside binding pocket. In the DS-1 VP8* core, replacement of these residues by R154 and S187 removes these walls. In fact, the R154 side chain stretches across the gap between the six- and five-stranded β-sheets to make a low ridge in place of the floor of the sialoside binding pocket. Although the structural data do not exclude the possibility that an alternative carbohydrate ligand binds in place of sialic acid in DS-1, the surface of the DS-1 VP8* core that corresponds to the RRV sialoside binding site does not contain an obvious binding pocket.

Structural Polymorphism.

Sequencing of genes encoding VP4 from different rotavirus isolates shows that many strains, such as DS-1, have a single residue deletion in the FG loop. The FG loop links the EF β-ribbon to the six-stranded β-sheet. The missing residue in DS-1 would correspond structurally to RRV residue Q135. The packing of the EF β-ribbon against the six-stranded β-sheet creates a cleft, which is adjacent to the cleft between the β-sheets that forms the SA binding pocket in RRV. Near the deletion, the cleft between the EF β-ribbon and the six-stranded β-sheet is wider in the DS-1 VP8* core than in the RRV VP8* core, possibly because the shorter loop does not permit as close an approximation of the proximal portion of the β-ribbon to the six-stranded β-sheet.

Most rotavirus strains isolated from humans, including strains from the most common human rotavirus P types, share the deletion in the FG loop. Rotavirus strains without the deletion that have been isolated from humans are members of P types, such as 5A[3], 3[9], 4 [10], and 11 [14], that also contain animal rotavirus strains and are infrequently isolated from humans. This observation suggests that human strains without the deletion have descended relatively recently from viruses that crossed the species barrier from non-human animals. Strains with the deletion are consistently SA-independent, as verified by the presence of a hydrophobic residue at position 101. However, the deletion is not required for SA-independence, as it is not shared by all SA-independent strains. Thus, most strains that infect humans are not only SA-independent, but also share a deletion and probably also share a widened cleft between the β-ribbon and the six-stranded β-sheet This common structural feature in human rotavirus strains could be an adaptation to efficient replication and spread in human populations or simply a consequence of common ancestry. The phylogeny of rotavirus VP4 does not clearly distinguish these two possibilities. The deletion is not unique to human rotavirus strains. Most strains with the deletion do cluster in a single VP4 clade, which contains P genotypes 4, 6, 8, and 19. However, strains in P genotype 11, which includes both human and bovine rotavirus strains, also have the deletion. Because VP4 of P[11] is an evolutionary outlier among group A strains, common ancestry is not a definitive explanation for the distribution of this polymorphism.

DS-1 VP8* Binds an Amino Acid Chain in a Second Surface Cleft.

Figure 10:
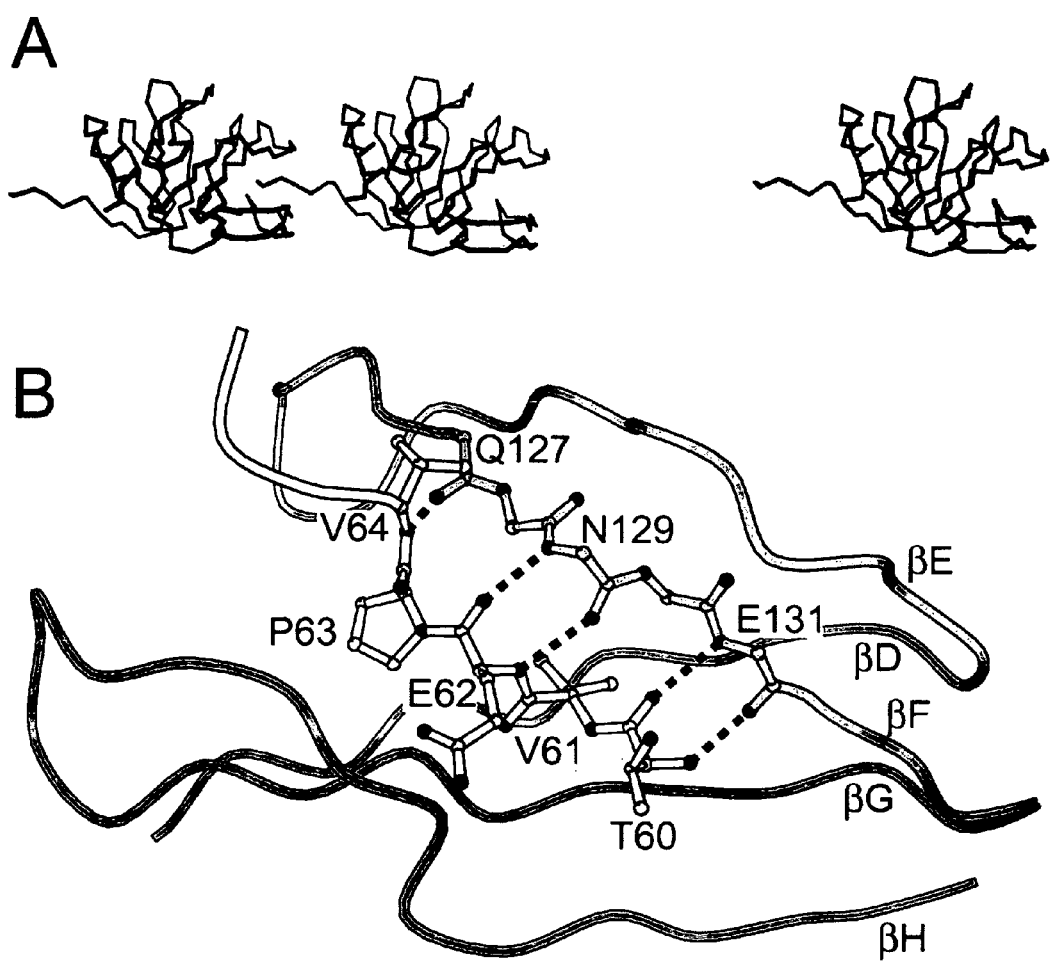
FIG. 10.

The DS-1 VP8* core crystal structure suggests that the broadened cleft between the β-ribbon and the six-stranded β-sheet may, in fact, be an adaptation that allows VP8* to bind a protein ligand. In the asymmetric unit of the DS-1 VP8* core crystal, each of the eight protein molecules "bites its neighbor's tail" (FIG. 10A). That is, the cleft between the β-ribbon and the six-stranded β-sheet of each VP8* core binds the N-terminal five residues (60-64) of a neighboring VP8* core, linking the cores into chains. The bound N-terminal residues are not part of the tightly folded structure of the core, but instead form a "leader." The equivalent residues are disordered in the RRV VP8* core crystal and solution structures. In the DS-1 VP8* core crystal, the binding of the leader is stabilized by the insertion of the aliphatic V61 side chain into a pocket lined by hydrophobic residues at the base of the cleft. The leader is held in alignment by five backbone amide-to-carbonyl hydrogen bonds that form between residues 60, 62, and 64 of the leader and residues 131, 129, and 127 of strand F in the β-ribbon, thus making a new intermolecular three-stranded β-sheet with strands E and F (FIG. 10B).

We used nuclear magnetic resonance (NMR) spectroscopy to assay the binding in solution of a peptide based on the leader to the potential peptide binding cleft. The assayed peptide was $^{15}$N-labeled on valine and had the sequence, TVEPVS (SEQ ID NO: 7), corresponding to DS-1 VP4 residues 60-64 plus a C-terminal serine. To avoid competition between the peptide and residues of the authentic N-terminal leader of the unlabeled VP8* core, residues 60-64 of the core were mutated to SGSGG (SEQ ID NO: 8) using PCR. Two-dimensional $^{15}$N-$^{1}$H heteronuclear single quantum correlation (HSQC) spectra showed no change in the chemical shifts of the $^{15}$N valines of the peptide when 0.29 mM DS-1 VP8* core was added to 0.1 mM peptide. Thus, the free peptide in solution did not bind the cleft with measurable affinity. There is no evidence the VP8*(or uncleaved VP4) molecules interact with each other in this manner during viral replication.

Indeed, close inspection of the DS-1 VP8* core crystal structure indicates that the bound leader does not fit the cleft optimally. The cleft continues beyond the N-terminus of the bound leader; the hydrophobic pocket that holds the V61 side chain could accommodate a bulkier moiety (not shown); the P63 side chain prevents formation of potential hydrogen bonds between the leader and residues in strand H and the GH loop; and the leader is forced out of the cleft beyond P63 by steric hindrance from the tightly folded region of its own VP8* core. However, the crystal packing demonstrates that the surface of DS-1 VP8* has a potential ligand binding site that is large enough to accommodate a peptide chain and offers extensive potential hydrogen bonding and hydrophobic interactions.

A similar, although narrower, cleft is also present on the surface of the RRV VP8* core. This potential ligand-binding cleft contains some of the few conserved regions on the otherwise highly variable surface of the VP8* core. Based on fitting to electron-cryomicroscopy image reconstructions of rotavirus virions of SA-dependent strains, this cleft is exposed at the tips of the VP4 spikes in a position favoring interaction with host cell proteins. As described previously, the VP8* β-ribbon appears to be an elaboration of a much shorter loop in the galectins, and it blocks the galectin carbohydrate binding site. The DS-1 VP8* core crystal structure suggests that the elaboration of the β-ribbon may also have created a new ligand binding site at the tip of the primed VP4 spike.

Escape Mutations Selected by Human Neutralizing mAbs Against Rotavirus.

We previously described three human neutralizing mAbs against rotavirus, derived from a phage display library of B lymphocyte cDNA from naturally infected humans. The phage antibodies were selected for binding to rotavirus strain KU virions, tested for neutralization of strain KU, and converted to IgG1 mAbs through recombinant DNA manipulation. One of the mAbs, 2-11G, binds VP7. The other two bind VP4 and neutralize heterotypically: 1-2H neutralizes P[4] and P[8] rotaviruses; 2-3E neutralizes P[6] and P[8] rotaviruses.

We have now mapped the residues recognized by 1-2H and 2-3E in strain KU, using neutralization escape mutant analysis (FIG. 9). MAb 1-2H selects a unique G to D mutation at VP4 residue 170, and mAb 2-3E selects a unique E to K mutation at VP4 residue 203. Both mutations are in the VP8* fragment of VP4. Three VP8*-specific antibodies that neutralize human strains of rotavirus have been described previously. Two of these mAbs, HS11 and RV5:2, neutralize homotypically. The other mAb, HS6, neutralizes P[6] and some P[8] viruses (FIG. 9). Thus, three of five neutralizing monoclonal antibodies that recognize VP8* of human rotavirus strains neutralize heterotypically. A more limited degree of heterotypic neutralization has been observed among the 20 mapped mAbs that bind VP8* and neutralize animal rotavirus strains. Heterotypic neutralization by monoclonals derived from naturally infected humans may reflect selection for broad specificity following repeated rotavirus infection. This result correlates well with the increasingly broad serum neutralizing response against rotavirus elicited by re-infection with rotaviruses of the same or different rotavirus serotypes.

Although VP5* is more conserved between strains than is VP8*, the presence of heterotypic neutralization epitopes on VP8* of human strains suggests that immunization with recombinant VP8* of human strains could induce a heterotypic neutralizing antibody response (which we define as eliciting antibodies that neutralize more than one P type). In fact, primary immunization of laboratory animals with recombinant VP8* of an animal rotavirus strain (RRV) does produce heterotypically neutralizing antibody.

Mapping of Neutralization Escape Mutations on the DS-1 VP8* Core Structure.

Figure 11:
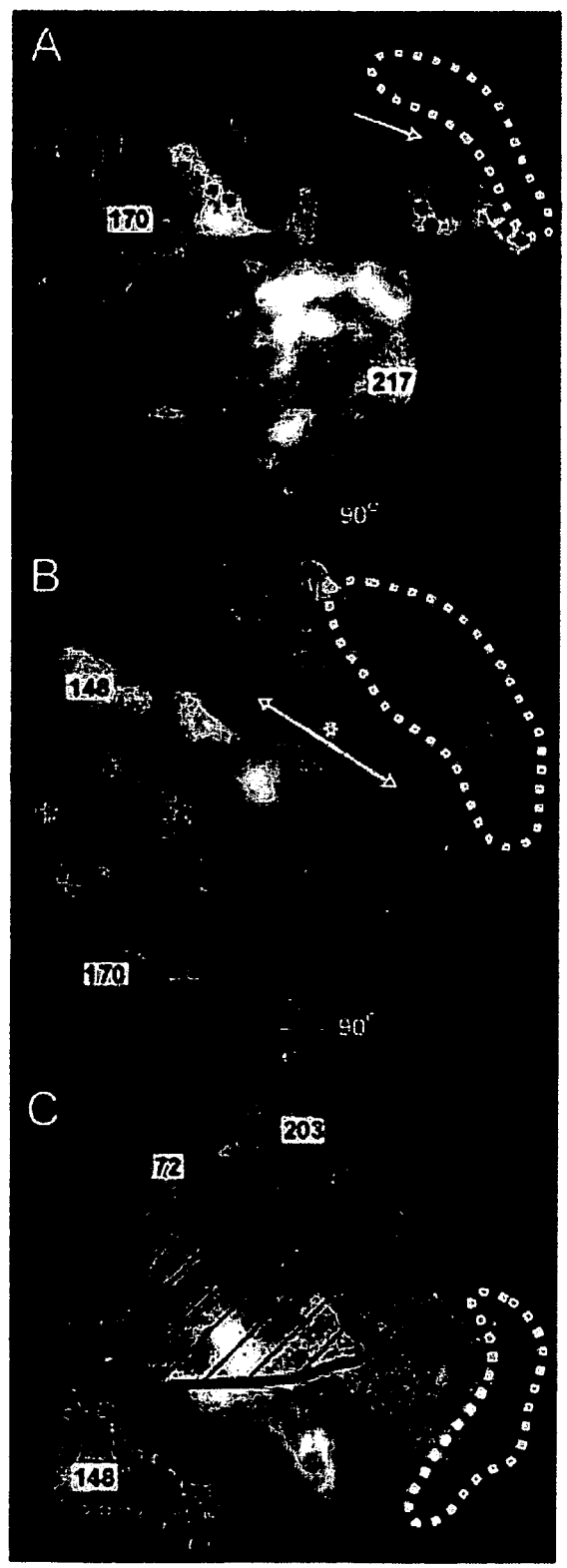
FIG. 11 depicts neutralization escape mutations mapped onto the DS-1 VP8* core. The view in FIG. 11B matches the view in FIG. 8. The views in FIGS. 11A and 11C are rotated about a horizontal axis by 90' in either direction from the view in FIG. 11B, as indicated by the arrows. The surface representations are colored by conservation among a previously described set of VP8* sequences from 19 P genotypes. The most conserved surfaces are colored blue; the most variable surfaces are colored red. Neutralization escape mutations of SA-independent rotavirus strains (all of them isolated from humans) are identified by residue number. Surfaces corresponding to the previously described neutralization epitopes on VP8* of SA-dependent strains are indicated by dotted outlines: green outline, epitope 8-1; blue outline, epitope 8-2; yellow outline, epitope 8-3; pink outline, epitope 8-4. In panels A and B, the potential peptide binding cleft is indicated by a white arrow. In panel B, the hydrophobic pocket at the base of this cleft is indicated by a white asterisk. In panel C, red cross-hatching marks a surface that would be inaccessible to antibody binding if the DS-1 VP8* core crystal structure were fit to an electron cryomicroscopy envelope of the head of the SA11-4F VP4 spike.

As previously described, the twenty neutralization escape mutations mapped to VP8* of SA-dependent animal rotavirus strains cluster in four epitopes (FIG. 11). The five neutralization escape mutations mapped to VP8* of SA-independent human rotavirus strains do not cluster in these epitopes. Only the mutation at residue 148 of human strain RV-5 lies within one of the previously described epitopes (designated 8-1). Rather, the escape mutations mapped to VP8* of human rotavirus strains are broadly distributed on the molecular surface and do not form any easily identifiable new epitopes. Because the DS-1 and RRV VP8* cores share a common fold, gross structural differences do not explain the distinct distributions of escape mutations.

When the RRV VP8* core crystal structure is fit to the envelope of the spikes in electron cryomicroscopy image reconstructions of trypsin primed SA-dependent rotavirus particles, the sites of all the escape mutations on VP8* of SA-dependent strains are accessible for antibody binding. However, if the DS-1 VP8* core structure is fit to the same molecular envelope, two of the five escape mutations on VP8* of SA-independent human rotavirus strains are located in the gap between the paired heads, where they are not accessible for antibody binding. Thus, the distribution of escape mutations suggests that the form of the spike recognized by some of the VP8*-specific antibodies that neutralize SA-independent human rotavirus strains differs from the form recognized by VP8*-specific antibodies that neutralize SA-dependent animal rotavirus strains. No electron cryomicroscopy image reconstructions of particles from SA-independent strains are currently available to test the hypothesis that the conformations of trypsin-primed spikes on SA-independent and on SA-dependent strains expose different molecular surfaces of the VP8* core for potential antibody binding.

VP4 spikes are known be have multiple conformations. Prior to trypsin priming, the spikes are not visible in icosahedral image reconstructions, reflecting flexibility. Three-fold symmetry of the portion of VP4 buried under the VP7 shell, the trimeric appearance of altered VP4 spikes on virions that have been treated with alkali (Prasad, in press), and the stable trimer formed by a rearranged VP5* fragment suggest that each VP4 cluster on the virion surface may contain three molecules, one of which remains flexible after trypsin priming. In addition, electron cryomicroscopy image reconstructions demonstrate conformational differences in spike morphology between SA-dependent rotavirus strains. Thus, strain differences in spike morphology or the multiple conformational states of VP4 could allow antibodies to bind all sites of neutralization escape mutations in SA-independent human rotavirus strains.

Conclusions.

Although the VP8* cores of a SA-dependent strain (RRV) and of a SA-independent strain (DS-1) share a common overall architecture, there are significant structural differences between the two phenotypic variants. The biochemical characteristics of both variants, including ease of expression and purification, high solubility, and chemical stability make them promising components for a potential second generation, recombinant rotavirus vaccine. In this regard, heterotypic neutralization by mAbs recognizing VP8* of human strains is a particularly promising finding. Differences between the RRV and DS-1 VP8* cores in the region that corresponds to the RRV SA binding site make it unlikely that DS-1 VP8* binds an alternative carbohydrate ligand in this location. A widened cleft between the EF β-ribbon and the six-stranded β-sheet in the DS-1 VP8* core and the binding of a peptide chain in this cleft suggest that VP8* may bind a protein ligand. The different neutralization surfaces of SA-dependent and SA-independent viruses suggest different mechanisms of neutralization and, possibly, differences in spike organization. Further structural studies on SA-independent rotavirus strains could reveal differences in the VP4 spike that are directly relevant to the pathogenesis of rotavirus gastroenteritis in children.

Example 6

Considerations in VP8* Core-Based Vaccine Design

The VP8* cores used in the structural studies is very stable, efficiently produced in *E. coli*, and contains many neutralizing epitopes. However, due to high surface variability, it may elicit a relatively narrow neutralizing response. Fortunately, as two serotypes cause approximately 97% of rotavirus gastroenteritis in children, the need for heterotypic neutralization may be limited. Most mAbs recognizing VP8* neutralize sialic acid-dependent strains, but sialic acid-independent strains cause most human disease. We will determine whether immunizing with a single VP8* core or a cocktail of VP8* cores from different rotavirus strains provides a sufficiently heterotypic neutralizing response. The immune sera will be tested for breadth of neutralization. As multimeric complexes are particularly effective immunogens, linking the monomeric VP8* core into a multimer by genetic or chemical manipulation may increase its immunogenicity.

Based on its well-defined termini, efficient expression in *E. coli* (yield of 20 mg of pure protein per liter of culture), rapid two column purification (glutathione affinity with elution by trypsin digestion followed by gel filtration), high solubility (>65 mg/ml), protease resistance (trypsin digestion is part of the purification protocol), and chemical stability (stable NMR spectra in old samples) the VP8* core may meet the biochemical criteria that we wish to achieve through structure-based engineering.

We will optimize codon usage for VP8* antigens from human rotavirus strains to further boost efficiency of expression in the last stages of development. In addition, because VP8* is the major determinant of P serotype, several VP8* variant antigens will be expressed. Immunization with the current RRV antigen (P[3]) will allow for homotypic challenge in the suckling mouse model and heterotypic challenge in the adult mouse and gnotobiotic pig models. As P[4] and P[8] viruses cause most symptomatic rotavirus infections in humans, antigens representing both of these P types are likely components of a protective vaccine. Our DS-1 (P[4]) VP8* core covers one of these types, and the KU (P[8]) VP8* core, which we have expressed, covers the other type. Immunization of gnotobiotic pigs with the KU VP8* core will allow homotypic challenge with Wa (P[8]). If the VP8* core does not mediate heterotypic protection in the adult mouse model, a VP8* core based on the P type of a virulent murine challenge virus will be expressed. The determination of which P types to include in the final vaccine will require monitoring of global epidemiologic data. For example, P[6] rotavirus strains are increasing in prevalence in India and Africa. If the P type of the VP8* core proves important, the antigenic mix will be tailored to the strains circulating in target populations.

Example 7

Structure of RRV VP5CT, a Purified Protease Fragment of RRV VP4, and Implications for VP4 Rearrangements We determined the X-ray crystal structure of the presumptive membrane interaction domain VP5CT of rhesus rotavirus (RRV) VP4, in what we believe represents its post-membrane penetration state.

Figure 2:
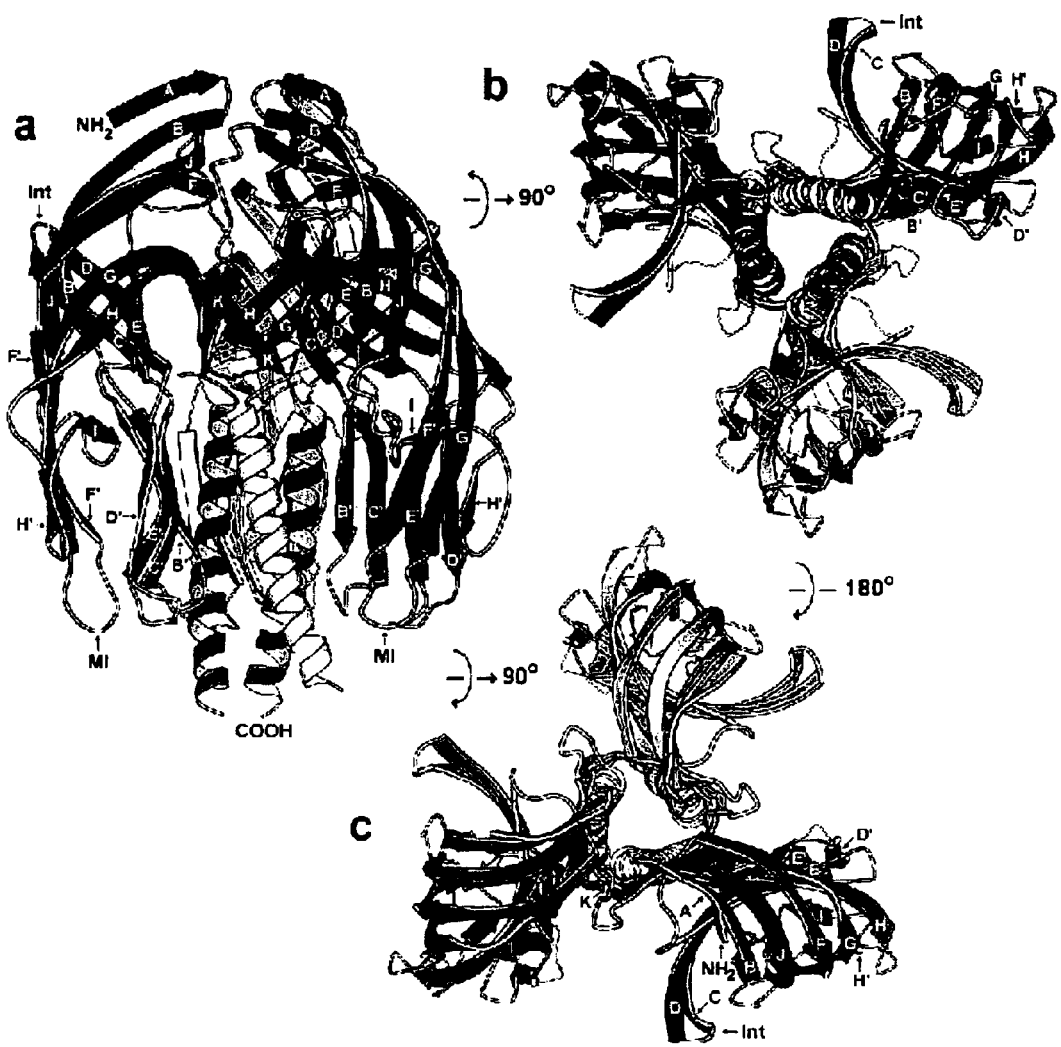
FIG. 2 depicts ribbon diagrams of the VP5CT trimer.
Figure 4:
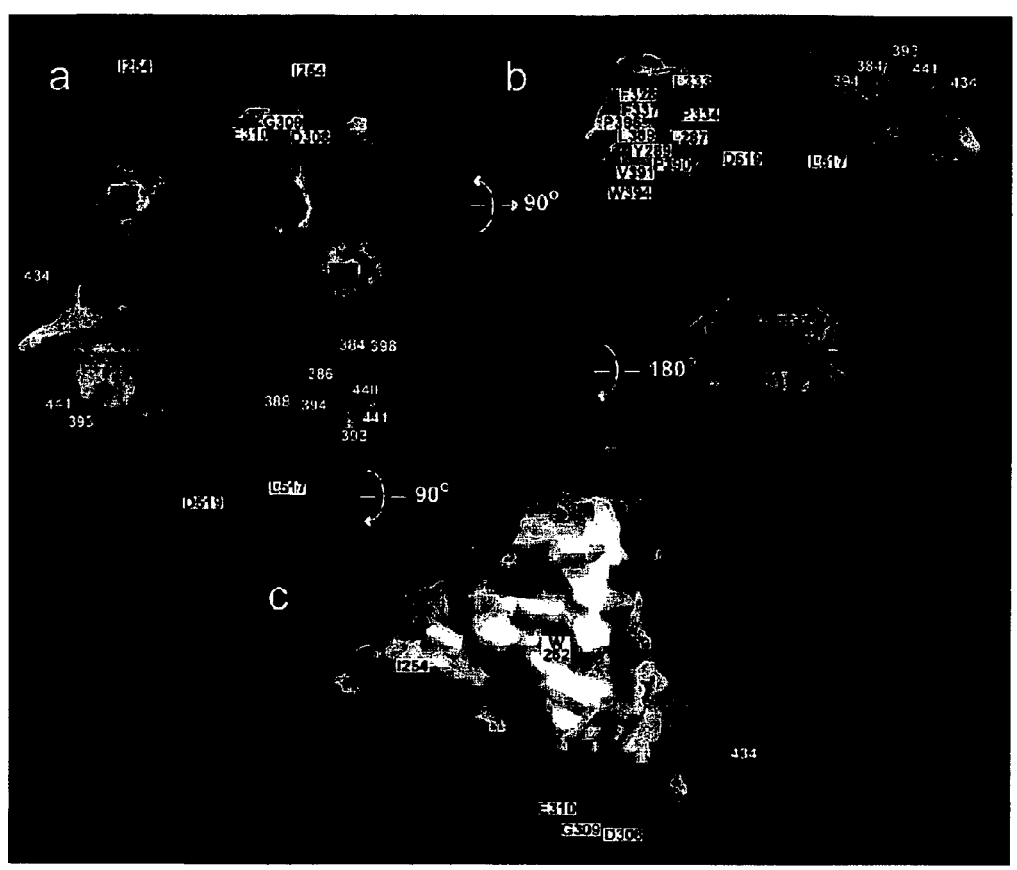

VP5CT is a well-ordered homotrimer. As depicted in FIG. 2A, it stands 84 Å high (measured on a Cα trace) and has a maximum radius of 37 Ø. The trimer resembles a folded umbrella, in which the post is a C-terminal, triple-stranded, α-helical coiled-coil, and each of the shade's three panels is an N-terminal globular domain. The sequence of the coiled-coil forms a heptad repeat from L494 to I512 (FIG. 3A), and hydrophobic side chains pack around the three-fold axis as predicted by this pattern. Beyond I512, the α-helices splay away from the three-fold axis (FIG. 2A). The external surface of the coiled-coil, against which the globular domains pack, carries a strong negative charge (FIG. 4A). The globular domain of each subunit contacts the groove between the α-helices of the other two (FIGS. 2A and 2B). An additional foot domain (FIG. 1A), similar in mass to the determined structure, is attached to the C-terminus of the coiled-coil in full-length VP5*.

The trimer is held together further by a nine-stranded, continuously hydrogen-bonded β-annulus, located on the three-fold axis just above the coiled-coil (FIG. 2A). The β-annulus contains β-strands K, H, and G from each monomer. At the top of the structure, the aromatic side chains of W262 (strand B) stack around the three-fold axis in a propeller-like fashion (FIG. 4C), forming an additional trimer contact. Between the β-annulus and the W262 propeller, a large cavity (volume 390 Å$^3$) centered on the 3-fold axis leaves room for potential rearrangements.

The core of each globular domain is an eight-stranded anti-parallel β-sandwich (light and dark blue in FIG. 3B). Two features of potential functional importance project from its top edge: the GH β-hairpin and the CD β-hairpin. The GH β-hairpin of each subunit arcs around to join strands K in the β-annulus (FIG. 2A), thus clamping the globular domains in the "folded umbrella" position. The CD β-hairpin has a flexible tip (high thermal parameters) with the sequence "DGE," which may bind α2β1 integrins. This tip protrudes into solvent (FIGS. 2C and 4C) and would be accessible for ligand binding. Integrin ligands often present exposed aspartic acid or glutamic acid side chains on extended flexible loops, like the CD hairpin.

Potential membrane-binding functions are plausibly attributed to extensions from the bottom edge of the β-sandwich (pink and purple in FIG. 3B). Four loops, of which the three longest are β-hairpins with hydrophobic residues at their tips (B'C, D'E', and F'G), project towards the C-terminus to create the apolar apex of the globular domain (FIGS. 2B, 3B, and 4B). The loops form β-sheets B'C'E'D' and F'G(H/H'), which are separated from each other near the 8-stranded β-sandwich by interposition of β-strand I (FIG. 3B and the green subunit in FIG. 2A). This unusual interposition creates a deep "hydrophobic bowl."

Of the four loops that project from the bottom of the β-sandwich, F'G is the most hydrophobic. The apolar side chains of P390 and V391 extend from its tip, and the aromatic W394 side chain lies over its solvent-exposed face (FIGS. 4A and B). Each strand of the hairpin has an in-register glycine-glycine pair (residues 382-383 and 399-400) at the positions of labels "F'" and "G" in the blue subunit of FIG. 2A and in FIG. 3B. These 4 glycines, conserved in all 20 P genotypes, could provide a hinge for the hairpin, opening up the hydrophobic bowl beneath and allowing relatively extensive and flexible membrane interactions during cell entry.

Fit to the Trypsin-Primed VP4 Spike

In a ~12 Å resolution image reconstruction from electron cryomicroscopy of trypsinprimed virions, the body of the VP4 spike has good two-fold symmetry, but its axis is displaced from the center of its base, to which it connects by a narrow, split, asymmetric stalk (FIGS. 5B and 5E). VP5CT residues Y267 to L470 neatly fit the spike body. As Y267 and L470 hydrogen bond to each other on adjacent β-strands (B and J), this region constitutes a self-contained structural domain (FIGS. 5C and F). This domain does not include the three structural elements that make central three-fold contacts in the VP5CT trimer: the C-terminal (α-helix, β-strand K (which links the GH hairpins in the β-annulus), and β-sheet ABJ. Thus, the N- and C-terminal regions of VP5CT must assume a different conformation in the dimeric spike. As the rearrangement that produces VP5CT protects K258 in β-strand A from trypsin cleavage, β-sheet ABJ probably forms during trimerization by the N-terminus of VP5* folding back against one edge of the eightstranded β-sandwich (FIG. 3B).

This fit places the hydrophobic apex of the VP5CT globular domain at the viriondistal end of the body (FIGS. 5B-F). Monoclonal antibody 2G4 selects a neutralization escape mutation at residue 393 of the F'G loop, which fits a "shoulder" adjacent to the head. Electron cryomicroscopy of FAb-decorated virions shows that 2G4 binds the shoulders,[22] confirming the orientation of the VP5CT globular domain in the spike. The hemagglutination domain, VP8CT, fits the heads, as shown previously at lower resolution[9] and confirmed by the present higher resolution reconstruction (FIGS. 5B and 5E). The heads cover much of the hydrophobic apex of the VP5CT globular domain. While a portion of the hydrophobic F'G loop, including the projecting W394 side chain, is probably solvent-exposed, the hydrophobic tips of the B'C' and D'E' loops are covered, as is the hydrophobic bowl between the three loops.

Figure 5:
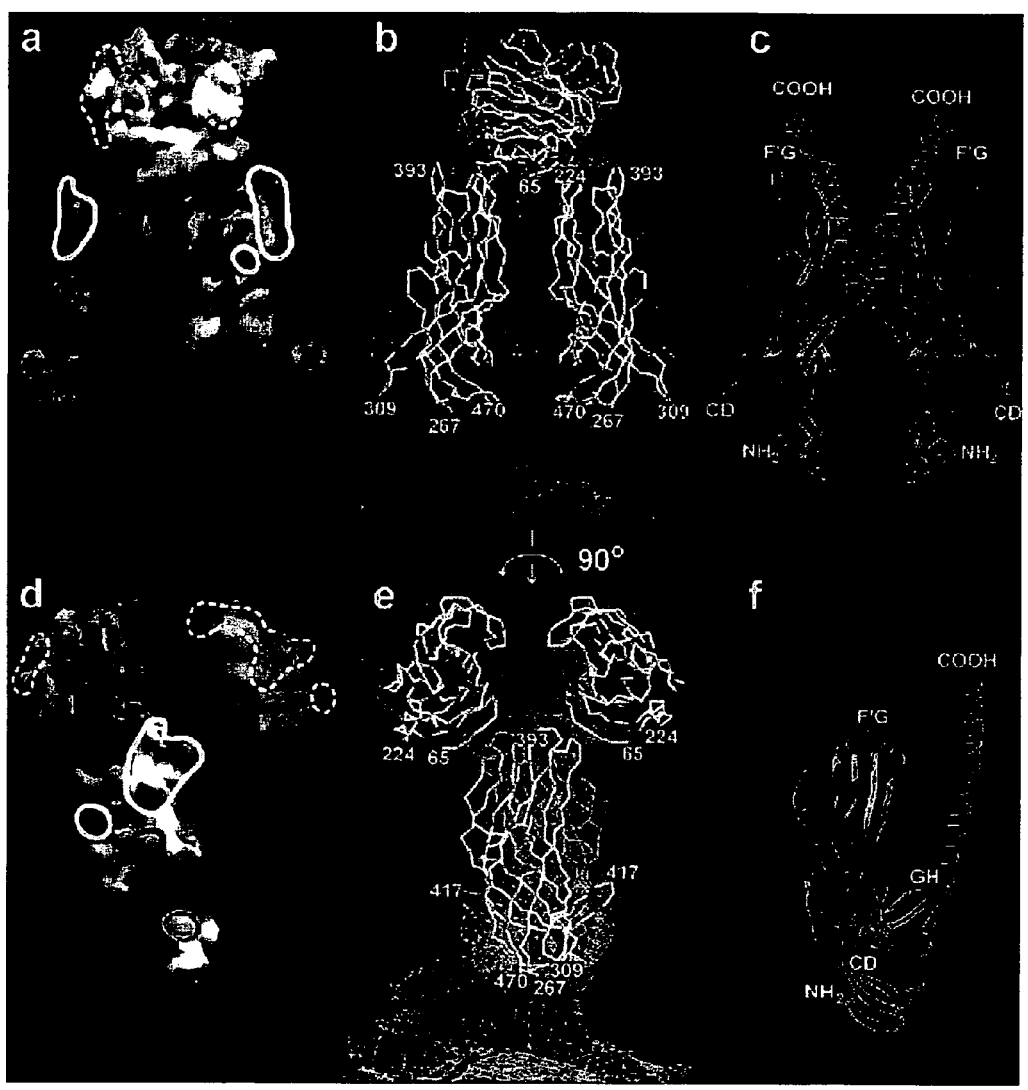

The two subunits of the body have proximal and distal dyad contacts but leave a gap between them (FIGS. 5B and E). The VP8CT and VP5CT domains that we have fit to the image reconstruction lack the residues that make these two-fold contacts. Both termini of VP8CT occupy the "neck" between the head and body. Both termini of the VP5CT globular domain occupy the base of the body. While the C-terminus (L224) of the VP8CT model in FIG. 5 is only 7 residues from the true VP8* C-terminus, the Nterminus (L65) of the model is 64 residues from the VP8* N-terminus. Therefore, VP8* residues M1-V64 form the distal dyad contact of the spike and tether the heads to the body. The portion of VP5CT not included in the fit domain (residues A248-Q266 and I471-L523, white outlines in FIGS. 5C and F), must form the proximal dyad contact, perhaps together with residues C-terminal to VP5CT.

The modeled VP8CT C-terminus (L224) is separated from the nearest modeled VP5CT N-terminus (Y267) by 63 Å (FIGS. 5B and E). While the intervening 42 residues could span this gap in an extended conformation, the VP5CT domain completely fills the image reconstruction between the proximal and distal dyad contacts. No path of unfilled density remains to suggest the presence of a connecting strand in the cleaved spike. Therefore, trypsin cleavage must remove the 16 residues that separate VP8* from VP5*, render them disordered, or allow a rearrangement to separate the cleaved termini. The image reconstruction does not resolve which head was covalently linked to which body subunit prior to the priming cleavage.

Entry-Associated Rearrangements

Image reconstructions from electron cryomicroscopy of rotavirus particles have provided good evidence for two conformational states of VP4: an uncleaved, flexible state and a trypsin-cleaved, rigid state with two-fold symmetry of the parts external to the VP7 shell (FIGS. 6A and 6B) These parts include residues 1 to 470—that is, VP8* and the globular domain of VP5CT (FIGS. 6B and D). Contrary to the clearly dimeric character of the projecting spikes on the virion, the X-ray crystal structure of VP5CT reveals a trimer. The extensive trimer contacts, including a triple-stranded coiled-coil, a nine-stranded β-annulus, and a "propeller" of tryptophan side chains, provide structural evidence that the VP5CT region of VP4 evolved to trimerize. Trimer contacts bury 3956 Å$_2$ (25.8%) of the surface area of each subunit from solvent accessibility, accounting for the resistance of the trimer to dissociation by SDS. The possibility that the trimeric association of VP5CT is a biochemical artifact rather than a functionally significant state is exceedingly remote.

Reconstructions of particles decorated by FAb fragments of monoclonal antibodies specific for either the VP8* or VP5* fragment show two FAb's bound to each spike. The local dyad axes of the spikes do not coincide with local or general icosahedral symmetry axes and are therefore not imposed by the icosahedral averaging used for image reconstruction. VP5CT thus represents a third conformational state of VP4. This conclusion suggests that a dimer-to-trimer rearrangement of at least one part of VP4 accompanies cell entry (FIGS. 6B and 6C). In previous experiments, we found that serial digestion of purified VP4 monomers by chymotrypsin and trypsin yields SDS-resistant VP5CT oligomers, providing a simple in vitro model for a VP4 conformational rearrangement.

Analytical ultracentrifugation of the rearranged product, VP5CT, did not clearly distinguish between trimers or tightly associated dimers that weakly associate into tetramers (dimers of dimers). The latter interpretation appeared at the time more consistent with the electron cryomicroscopy data and suggested that the rearrangement of VP4 in solution modeled the priming rearrangement on virions. We now know, however, that the serial protease digestion yields a very stable trimer and therefore probably models rearrangement to the final, post-membrane penetration state of the protein. The characteristics of the VP5CT trimer are reminiscent of the low-energy, post fusion states of enveloped virus fusion proteins, such as the influenza hemagglutinin and the HIV envelope glycoprotein. In these proteins, a primed conformation generated by proteolytic cleavage awaits triggering, by low pH or receptor binding, respectively, to release receptor binding domains and allow a conformational rearrangement. Likewise, when VP4 is assembled into the virion, interactions with VP6 and VP7 probably arrest the progression of rearrangements at the primed stage and also protect the VP4 foot from protease digestion, preventing separation of foot and body.

When, and how, does a two-fold to three-fold reorganization of VP4 occur? Either each spike location contains three VP4 subunits at all stages, or VP4 must dissociate during penetration, trimerize, and carry out its functions un-tethered to the viral capsid. A number of observations strongly favor the former model. First, the clustered Nterminal portions of two VP4 subunits, which associate only after trypsin priming, project from an angled stalk that emerges asymmetrically from the foot. Thus, the foot need not share the symmetry of the projecting spike. The N-terminal portion of a third subunit could remain flexible and hence invisible in the virion image reconstruction (FIG. 6B). Second, an image reconstruction of VP4 obtained by subtracting images of spikeless particles from images of trypsinized particles with spikes indicates that the foot of the spike has three-fold symmetry. This observation was explained previously by the suggestion that each of two VP4 subunits contributes three similarly shaped domains to the foot, creating a pseudo-hexameric arrangement. We suggest instead that the image actually reveals the correct oligomeric state of the foot. Third, an image reconstruction of trypsinized rotavirus particles after treatment at pH 11 reveals foreshortened spikes with apparent three-fold symmetry. We suggest that unfolding at high pH causes each molecule of VP4 to condense around the center of its peripentonal channel. If just two of the three VP4 molecules at each spike location cluster after trypsin cleavage, the interactions of VP4 with VP7 and/or VP6 must select the ones that form the visible spike. The VP8* and VP5* fragments of the third, flexible molecule need not remain associated after trypsin cleavage, and this molecule could even perform a different function in cell entry. The alternative model, in which the trimer forms only after uncoating, requires that VP4 acts like a soluble toxin, either alone or in complex with VP7, to mediate translocation of the DLP across a cell membrane. In the absence of a maintained physical connection between the membrane penetration apparatus and the DLP, the means by which this apparatus translocates the DLP into the cytoplasm is difficult to envision.

In the dimeric spike, the putative membrane interaction hairpin (F'G) points away from the foot and the GH hairpin points approximately 90° away from the axis that separates the two subunits of the body (FIGS. 5B, 5C, 5E, and 5F). In the VP5CT trimer, the F'G hairpin points towards the C-terminus of the coiled-coil, to which the foot attaches, and the GH hairpin participates in the β-annulus around the three-fold axis (FIG. 2A). Therefore, in the dimer-to-trimer rearrangement, each subunit of the body must rotate approximately 180° about an axis roughly perpendicular to the long axis of the spike body (FIGS. 6B and C). This dramatic domain movement translocates the putative membrane interaction hairpin by at least 55 Å from the shoulder of the spike towards the foot.

Rearrangements of the VP4 sequences that form the proximal and distal dyad contacts in the spike probably control the large-scale displacements of the globular domains. The distal dyad contact (residues 1-64) also anchors the heads to the body (FIGS. 6B and 6D). Rotation of the body subunits during the dimer-to-trimer rearrangement would separate the VP5* surfaces contacted by these residues, releasing VP8* (FIG. 6C). Conversely, loss of VP8*, promoted, for example, by cell-surface binding, would expose hydrophobic surfaces at the apex of the VP5CT globular domain and could relieve a conformational constraint on the body, triggering the fold-back rearrangement.

Interaction of the F'G hairpin with lipids, interaction of the CD hairpin with integrins, and disruption of the VP7 shell in a low-calcium environment are other possible triggers. The proximal dyad contact of the spike must contain the residues that, in the trimer, form the coiled-coil (FIGS. 6B-D). The "zipping up" of the coiled-coil may power the dimer-to trimer transition.

Model for the Entry Pathway

Figure 6:
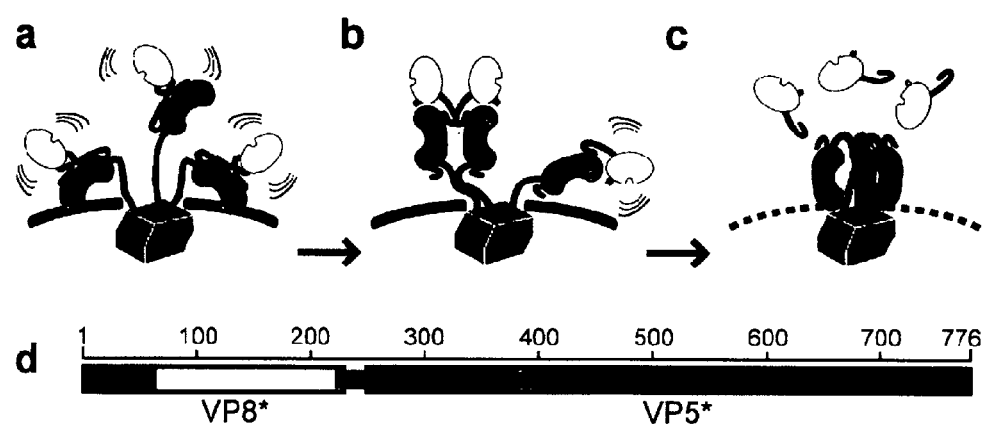

The structural data presented here delineate key steps in rotavirus entry (FIG. 6). An initial conformational change, triggered by protease cleavage between VP8* and VP5*, primes VP4 for membrane attack. The primed spike is made rigid by dimeric interactions in the external portion of VP4. The heads of the spike shield hydrophobic prominences at the top of the body. VP4 binds the cell surface through interactions with cell surface carbohydrates and/or proteins (with strain variation in receptor usage). Dissociation of VP8* (which includes the heads) from VP5* unmasks the hydrophobic apex of the VP5CT globular domain, which may insert into a host cell membrane. A dimer-to-trimer rearrangement accompanies the folding-back of the membrane interaction domain. The resulting translocation of the putative membrane interaction region toward the foot (and possibly the virion surface) may disrupt a host cell membrane. This disruption could create the breach through which the DLP enters the cytoplasm. Alternatively, it may simply make a transient channel that lowers the calcium concentration near the virion, triggering uncoating and subsequent entry events. To validate and extend this model, we must determine whether the dimer-to-trimer transition occurs on or off the virion, study the membrane interactions of well-defined conformational states of VP4, and correlate the molecular rearrangements observed in simple biochemical systems with events that occur during the productive entry of rotavirus into cells.

Example 8

VP4 Neutralization Epitopes on VP5CT

The information about neutralization antigens provided by the high-resolution structure of RRV VP5CT described above permits the design of improved immunogens. The structure of the membrane interaction region of rotavirus (VP5CT) shows that major rearrangements in the spike take place in the course of entry, with a possible membrane interaction peptide being translocated from a position near the top of the spike to a position proximal to the viral surface. the neutralizing epitopes on VP5* are contained within a single compactly folded domain, which we call the "VP5* antigen domain." The VP5* antigen domain is a substructure of VP5CT. This domain also induces neutralizing antibodies in immunized mice. Examination of the structure suggests a strategy for efficient production of this very stable antigen.

While the VP4 protease fragment, VP5CT, would be an especially desirable immunogen because it contains the target of broadly heterotypic neutralizing antibodies, attempts to express VP5CT directly produced only insoluble protein—the fragment requires cleavage from an intact VP4 precursor to fold properly. VP5CT is purified with four chromatographic steps and a serial protease digestion, yielding only about 150 μg of protein per liter of insect cell culture. Therefore, VP5CT is not practical as a vaccine component. The structure of VP5CT, yields insights into rearrangements of VP4 during cell entry, reveals the VP5* neutralization surfaces, and provides the structural understanding needed to engineer a VP5* antigen with biochemical characteristics that allow its inclusion in a vaccine.

The globular domain of VP5CT contains all known heterotypic neutralizing epitopes on VP4 as well as a number of homotypic neutralizing epitopes (Table 2).

TABLE 2

Neutralization Epitopes on VP5CT

| Position* | Mutation | Strain† | Epitope | Antibody | Neutralized P serotypes‡ |
|---|---|---|---|---|---|
| 306 | L to P | KU | 5-5 | YO-2C2 | 1A, 2A |
| 384 | N to K | RV-3 | 5-1 | RV-3:3 | 2A |
| 386 | N to E | ST3 | 5-1 | HS16 | 2A |
| 386 | D to N | KU | 5-1 | KU-12H | 1A |
| 388 | A to E | RRV | 5-1 | M2 | 1A, 2B, 5B, 7 |
| 393 | Q to P | RRV | 5-1 | M7 | 5B, 7 |
| 393 | Q to P | RRV | 5-1 | 2G4 | 5B, 7, 9 |
| 393 | A to V | Wa | 5-1 | 1E4 | 1A, 2A |
| 393 | A to V | KU | 5-1 | KU-10C | 1A, 2A |
| 393 | A to V | F45 | 5-1 | F45:4 | 1A, 2A |
| 393 | A to T | KU | 5-1 | YO-1S3, ST-1F2 | 1A, 2A |
| 393 | A to T | KU | 5-1 | KU-6B11 | 1A, 2A, 5B, 6 |
| 393 | K to E | DS-1 | 5-1 | S2-2F2 | 1B |
| 393 | N to H, K, S | SA11-4fM | 5-1 | Hyper-immune § | |
| 394 | H to Y | K8 | 5-1 | 2C12 | 3 |
| 398 | S to R | ST-3 | 5-1 | ST-3:3 | 2A |
| 429 | S to R | KU | 5-4 | KU-2A, KU-10H | 1A, 1B |
| 434 | E to K | KU | 5-2 | KU-7E | 1A, 1B |
| 434 | E to K | KU | 5-2 | KU-4D7 | 1A, 1B, 2A |
| 434 | E to D | KU | 5-2 | S3-5E | 1A, 1B, 2A |
| 440 | L to S | KU | 5-1 | YO-1E6 | 1A, 2A |
| 441 | R to G | RRV | 5-1 | KU-6B11 | 1A, 2A, 5B, 6 |
| 459 | G to R | Wa | 5-3 | 1A10, 1C6 | 1A |

*Position based on alignment to the RRV sequence. Corresponding residues in VP4 of strains Wa, DS-1, KU, ST3, RV-3, and F45 are −1 relative to this numbering, due to the absence of a residue corresponding to residue 136 in RRV.

The VP8* core contains the remaining VP4 neutralizing epitopes. VP8CT and the antigen domain of VP5CT thus constitute the VP4 neutralization antigens, and they are logical minimal antigens for use in recombinant rotavirus vaccines. Mapping amino acid sequence variability among the 20 P genotypes of VP4 onto the surfaces of these antigens demonstrates both variability in the heads and conservation in the body of the spike, suggesting greater functional constraints on the body (FIGS. 5A and D). Immunization with VP5CT or its globular domain may elicit antibodies that neutralize a wide variety of rotavirus strains.

Mapping antibody neutralization escape mutations onto the VP5CT structure allows grouping of these mutations into five neutralization epitopes (FIG. 5A-C and Table 2). All the mutations map to surfaces that are solvent exposed in both the dimeric and trimeric conformations (FIG. 4A-C and FIGS. 5A and D). The solvent-exposed surfaces of the VP5CT trimer formed by the B'C'E'D' β-sheet and the ABJ β-sheet lack neutralization epitopes (FIG. 3A). These "silent" surfaces are inaccessible on the dimeric spike: the B'C'E'D' β-sheet faces the dyad axis, and the ABJ β-sheet is rearranged. Thus, the silent surfaces are not presented on the trypsin-primed virions used as immunogens and/or screening antigens to produce the monoclonal antibodies described to date.

Immunization with VP5CT trimers or the VP5CT globular domain alone might elicit antibodies that recognize the silent surfaces. Such antibodies could inhibit cell entry by novel mechanisms and be used to pinpoint structural rearrangements during cell entry. Approximately two-thirds of described VP5*-specific neutralizing monoclonal antibodies map to epitope 5-1 (Table 2). This epitope corresponds to the F'G β-hairpin and the adjacent H'I loop (FIG. 3). The post-attachment entry event blocked by an antibody mapping to this epitope might be the dimer-to-trimer rearrangement (see above) or hypothesized interactions of the F'G hairpin with cell membranes. Epitopes 5-1, 5-2, 5-3, and 5-4 are linked by a network derived from crosscompetition of antibodies for binding and cross-resistance of escape mutations to neutralization (Table 2). Antibodies recognizing these epitopes may therefore have similar mechanisms of neutralization. In contrast, epitope 5-5 is distinct: it is defined by an escape mutant that is neutralized by antibodies mapping to the other epitopes. Epitope 5-5 is located on the CD hairpin, adjacent to the putative integrin-binding site, suggesting that antibodies binding this epitope may block integrin interactions. Antibodies recognizing epitope 5-5 also bind a short synthetic peptide,$_{23}$ consistent with the flexibility of the CD hairpin.

The information about neutralization antigens provided by high-resolution structure determination of VP5CT permits the design of improved immunogens. In the case of many pathogens, sequence analysis of neutralization escape mutants has defined the specific targets of the neutralizing antibodies that protect from disease. High-resolution structures reveal the molecular surfaces and the underlying molecular architectures corresponding to these identified epitopes. The structures tell us what parts of an antigen must be left intact and what parts can be changed to optimize biochemical and immunologic performance. Thus, we can design optimized antigens that are more stable, soluble, homogeneous, efficiently produced, and effective at presenting known targets of immunity than the native molecules upon which they are based. Improved vaccines that incorporate these antigens will broaden the range of vaccine-preventable diseases, further improve safety, and make immunization less expensive and more practical.

Structural biology has revealed the specific molecular surfaces that form the desired target epitopes on microbial neutralization determinants, but existing subunit vaccines have not harnessed this knowledge for optimal antigen design. As a result, these vaccines still contain components that are not necessary for inducing immunity, require a cold chain, and can be expensive and inefficient to produce. Furthermore, native antigens may not present the desired target structures efficiently—microbial surface proteins are adapted to evade immunity, not to induce it. We aim to manipulate the physical and antigenic properties of neutralization determinants to make them optimal immunogens. These properties result from three-dimensional folding and quaternary associations, which can not be predicted from amino acid sequence alone. Therefore, rational engineering depends on a high-resolution understanding of antigenic structure.

Example 9

Structure of Directly Expressed RRV VP5* Antigen Domain and Implications for VP4 Rearrangements and Vaccine Design We also performed biochemical and X-ray crystallographic analyses of a directly expressed VP5* antigen domain. These analyses demonstrate that this autonomously folding domain can self-associate in both a dimeric and a trimeric state, with many of the same structural elements switching between states. This intrinsic molecular property underlies the molecular gymnastics of the cleaved VP4 spike.

Expression and Purification.

Initial constructs encoded residues 247-479 and 263-474 of VP4. Both of the proteins encoded by these constructs contain all known heterotypic neutralizing epitopes from VP5*. Since both recombinant proteins behaved similarly, we chose the longer construct, 247-479, for further study since we could potentially learn about a larger portion of the entire protein. However, the shorter construct may be more suitable for use as a vaccine or pharmaceutical.

Genetic constructs containing the coding sequence for the rhesus rotavirus (RRV) VP5* antigen domain, based on RRV residues 247-479 (raqa nedivvskts lwkemqynrd itirfkfass ivksgglgyk wseisfkpan yqytytrdge evtahttcsv ngmndfnfrig gslptdfvis ryevikensy vyvdywddsq afrnmvyvrs laanlnsvic tggdysfalp vgqwpvmtgg avslhsagvt lstqftdfvs lnslrfrfrl tveepsfsit rtrvsrlygl paanpnngke yyevagrfsl islvpsndd—in one-letter amino acid code) and separated from an N-terminal histidine tag by a thrombin cleavage site, were prepared using standard techniques. When expressed in E. coli, the VP5* antigen domain is insoluble (data not shown). When expressed in Sf-9 cells from a recombinant baculovirus vector, the domain is readily purified by nickel affinity chromatography and size exclusion chromatography. In some preparations, anion exchange chromatography was interposed between the affinity and size exclusion steps. This procedure yields up to 4 mg of purified protein per liter of insect cell culture (although the yield is quite variable between preparations), and the purified protein is soluble to 4 mg/ml. SDS-PAGE, mass spectrometry, and N-terminal sequencing reveal heterogeneity based on incomplete cleavage of the histidine tag by contaminating proteases (not shown).

Solution Behavior.

The predicted MW of the VP5* antigen domain is 28 kD. Its apparent MW by size exclusion chromatography on Superdex 200 (Amersham-Pharmacia) is 45 kD. As the domain is globular, the high apparent MW suggests self-association. Equilibrium analytical ultracentrifugation reveals complicated self-associative behavior and indicates that at 25° C., the VP5* antigen domain is in a dynamic equilibrium between oligomeric states. The ultracentrifugation data are not sufficient to determination the distribution of these states. At 8° C., ultracentrifugation data indicate that the protein is trapped in a fixed distribution of states. Based on the average MW, this distribution must include oligomers with three or more subunits.

Crystal Structure of the VP5* Antigen Trimer.

The VP5* antigen domain crystallizes at 25° C. in hanging drops, using MPD as a precipitant. Crystals formed within 72 hours in (composition of MPD solution) at 25° C. These crystals were frozen using MPD as a cryoprotectant. MPD was increased then flash frozen in liquid nitrogen. Data was collected to 1.5 Å resolution at Advanced Light Source (ALS) beamline 8.2.2. When frozen, these crystals diffract X-rays coherently to 1.5 Å interplanar spacing (although anisotropy limits the resolution of useable data to 1.6 Å). When the same preparation of concentrated protein used for crystallization in MPD was stored at 8° C., crystals formed spontaneously in the bottom of the tube. These crystals were frozen using glycerol as the cryoprotectant and using flash freezing in liquid nitrogen. Data were collected to 2.0 Å resolution at ALS beamline 8.2.2. Following integration and scaling of each data set using HKL2000, structures were determined using phases derived from molecular replacement using the relevant residues from a monomer of the VP5CT structure as a search model. We determined the structure of these crystals by molecular replacement using part of the VP5CT crystal structure described in Example as an initial phasing model.

Figure 12:
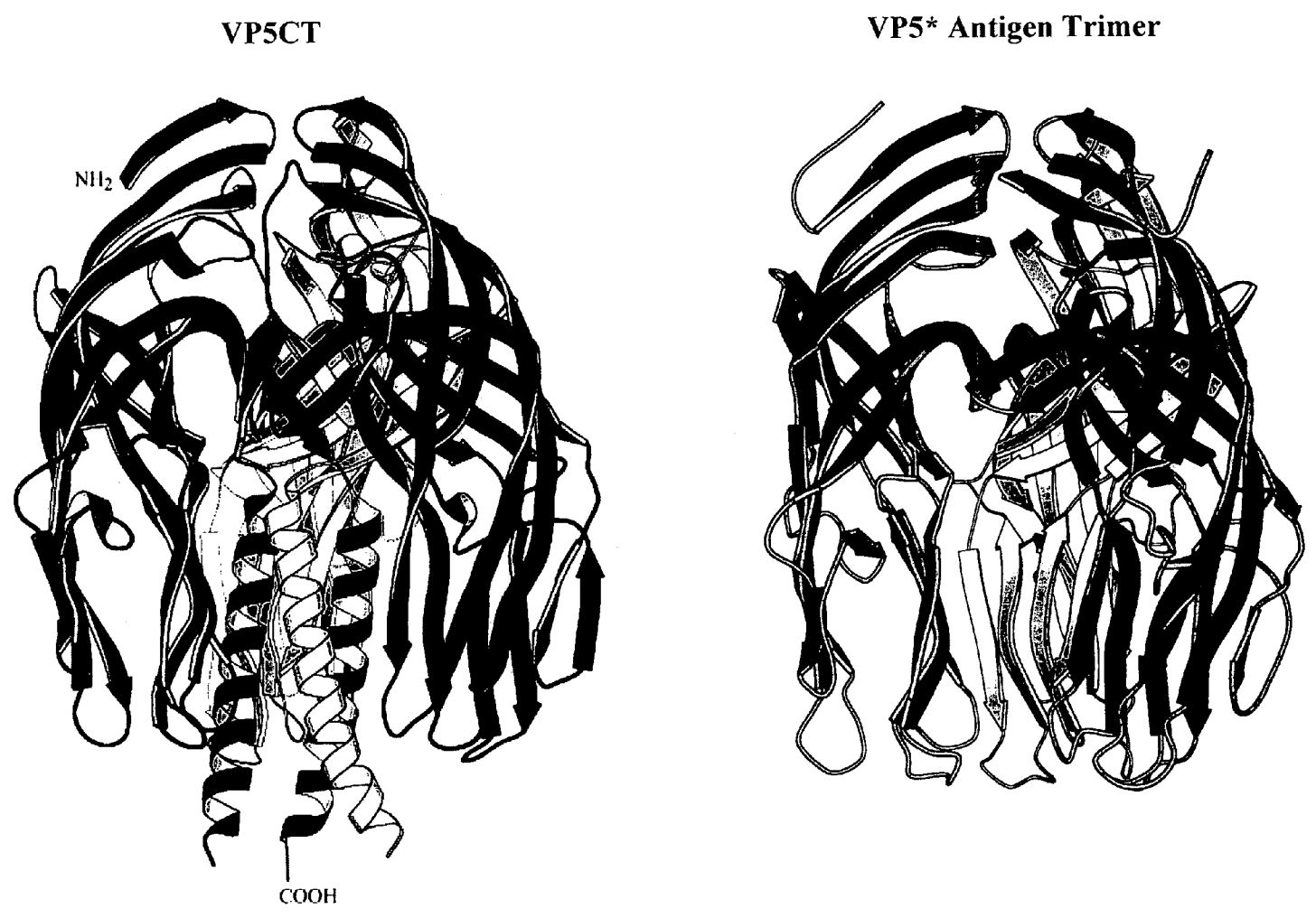
Figure 13:
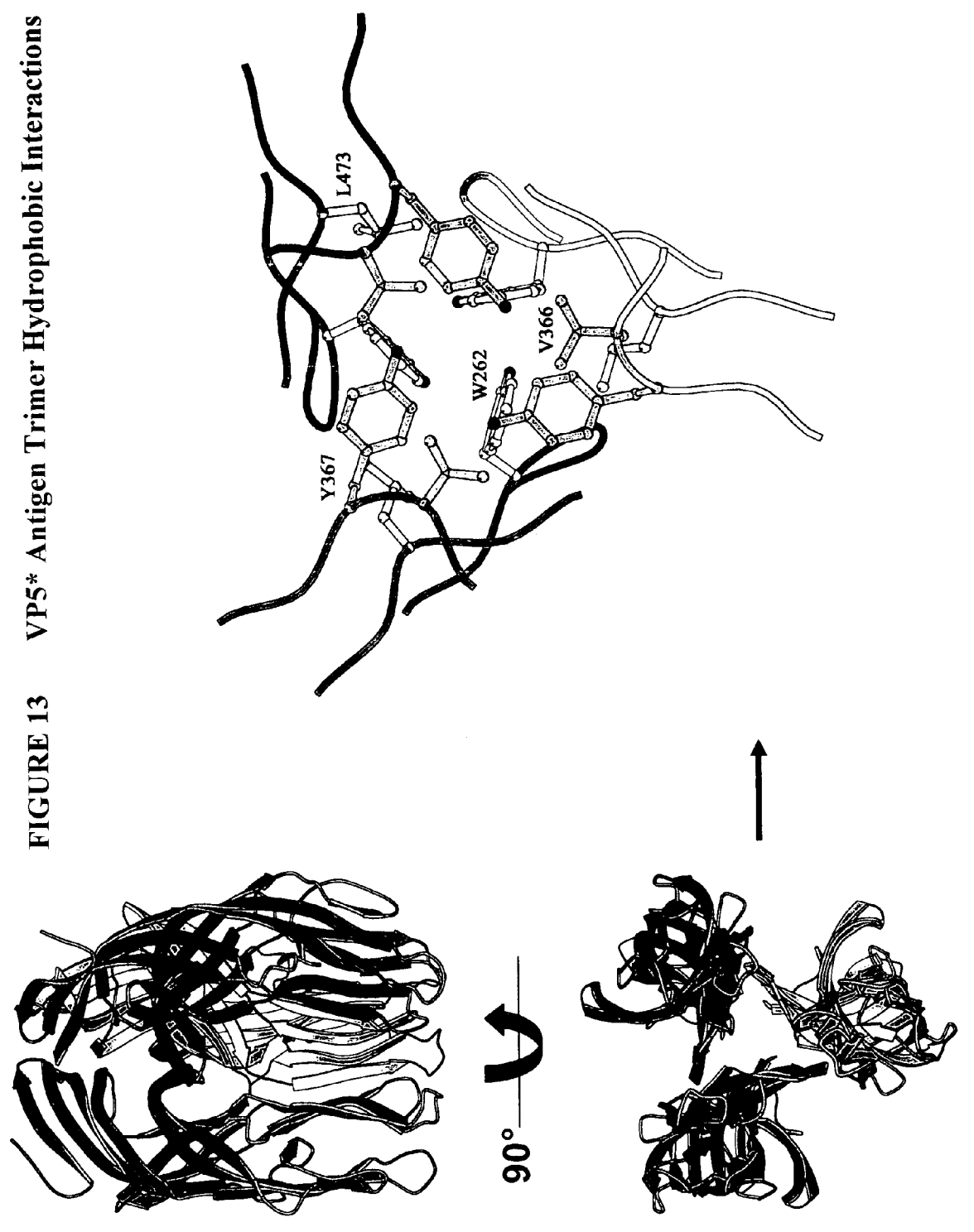

The structure reveals VP5* antigen domain trimers, which have the "umbrella" shape of VP5CT and are held together by a "cap" of buried hydrophobic residues (FIG. 12). The trimeric contacts in the cap include a wide topmost ring of interactions between each L261 side chain and aliphatic parts of the T259 and E264 side chains from adjacent subunits. Below this, a tight "propeller" of W262 aromatic groups packs around the three-fold axis, reinforced by interdigitating L473 side chains (FIG. 13). On the next level down, Y367 aromatic groups ring the trimer axis, reinforced by interdigitating V366 side chains (FIG. 13). A large solvent filled cavity that communicates with the molecule's exterior separates the ring of Y367 side chains from a lower ring of F415 aromatic side chains.

These trimeric contacts and the solvent filled cavity are also found in the cap of VP5CT trimers. In the complete spike, the communicating cavity could allow room for movements associated with trimerization and the folding back of the globular domain. Because the VP5 antigen domain trimer lacks a coiled-coil, the hydrophobic apex of the globular domain in each of its subunits can approach the three-fold axis more closely than in VP5CT trimers. Because interactions between the globular domains and the coiled-coil in VP5CT are polar, the lack of the central coiled-coil does not expose any hydrophobic patches. The hydrophilicity of the sides (but not the apex) of the globular domain allows for its free rotation through solvent during the fold-back translocation.

Figure 14:
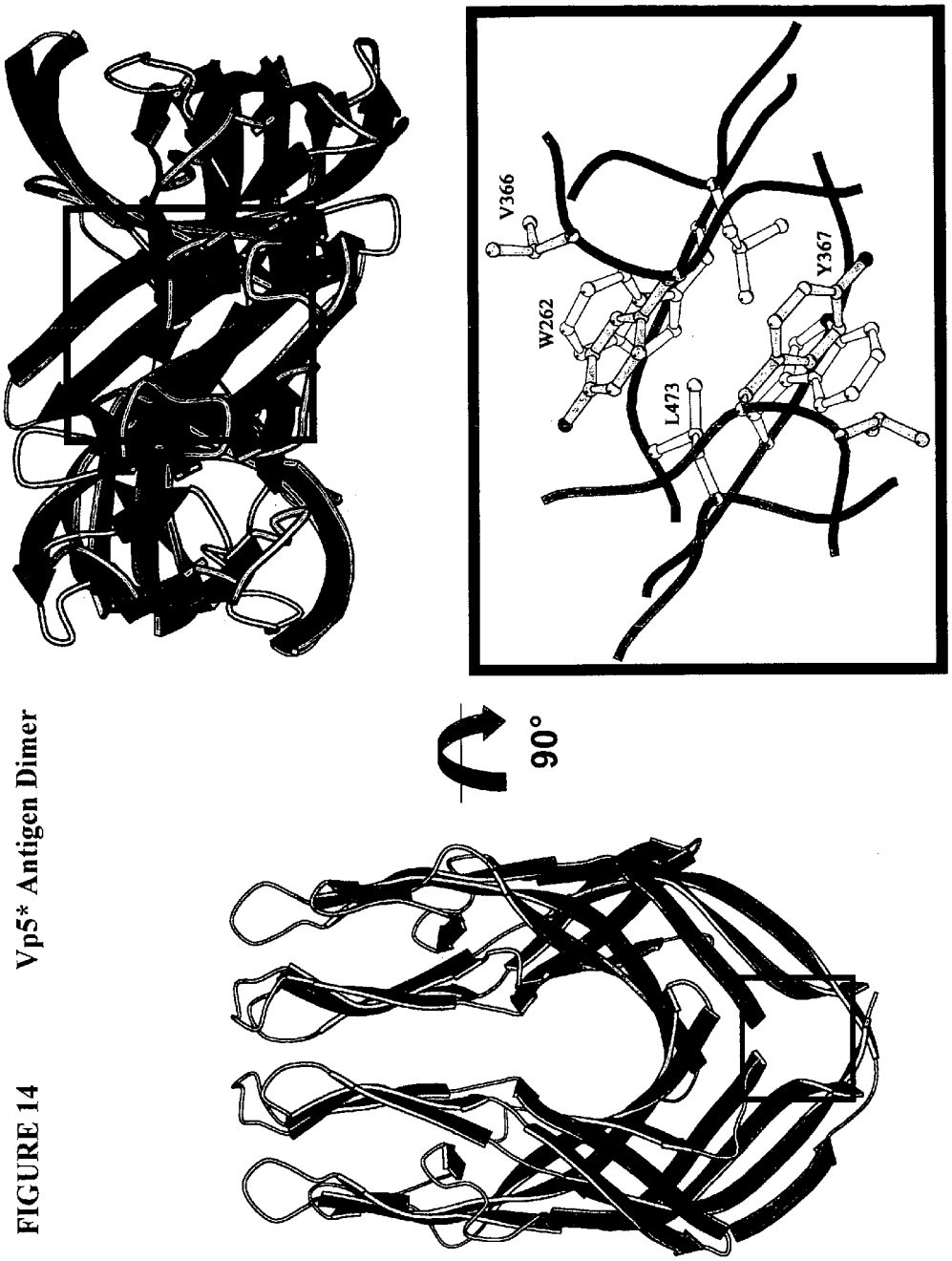
FIG. 14 depicts various views of the crystal structure of the VP5* antigen (R247-D479) dimer as well as its hydrophobic interactions and certain residues involved in the same.

The structure reveals slightly asymmetrical VP5* antigen domain dimers (FIG. 14). These dimers fit the molecular envelope of the body of the spike in electron cryomicroscopy image reconstructions of trypsin primed virions. The contact between the two subunits in the dimeric crystal structure fits the proximal dyad contact of the spike in the reconstructions. In the fit, the orientation of each subunit of the intact VP5* antigen domain dimer matches the orientation of the electronically extracted domains in a previously described fit of the globular portion VP5CT to the same molecular envelope. The C-terminus of the VP5* antigen domain extends into the stalk, so that it could connect to the buried foot domain in full length VP5*. The dimeric crystal structure fits the electron cryomicroscopy envelope imperfectly: the apex of each VP5* antigen domain protrudes beyond the "shoulders" of the spike, and virion-distal portions of the two subunits of the dimer are too close to the approximate dyad axis to fill the more lateral parts of the envelope. On virions, the N-terminus of VP8* probably forms the distal dyad contact, and tethers the heads to the body. The insertion of the VP8* tether into the distal dyad contact would force the apices of the two VP5* antigen domains apart, flexing the dimer about its main two fold contact. This could be expected to produce a better fit to the molecular envelope. In image reconstructions of the spikes, the dyad of the protruding part is slightly asymmetrical. The crystallized VP5* antigen domain dimer is also slightly asymmetrical. In particular, a highly ordered molecule of MPD inserts into the β-sandwich of one subunit (not shown). Asymmetry may be an inherent characteristic of the two-fold interaction of the VP5* antigen domain.

The dimeric crystal structure reveals details of the proximal two-fold contact of the spike on trypsin primed virions. A core of hydrophobic interactions and a new inter-subunit, four-stranded β-sheet hold the dimer together. The hydrophobic core is in a position equivalent to the cap of the umbrella-shaped trimer, and many of the same residues make inter-subunit contacts in both dimer and trimer. (The dimer structure is depicted "upside-down" relative to the trimer structure, to reflect the 180° domain rotation associated with the dimer-to-trimer transition.) At the bottom of the structure, the L261 side chain packs against its counterpart and against the aliphatic part of the T259 side chain in the other subunit. Above this, the W262 aromatic rings pack tangentially against each other, separated at the distal end by a sandwiched pair of L473 side chains (FIG. 14). In the next layer up, the aromatic rings of Y367 from each subunit stack together (FIG. 14). The F415 aromatic rings (which make three-fold contacts in the trimer) are widely separated from each other in the dimer (not shown).

The inter-subunit four-stranded β-sheet is formed by the GH loop (which includes residues 409-426) of each subunit. The central strands of the new β-sheet (strand G of each subunit) share eight backbone amide-to-backbone carbonyl hydrogen bonds and an additional hydrogen bond between the S412 side chain and its symmetry mate. The GH loop also has an essential role as a three-fold contact in the VP5CT trimer-incorporation of the GH loop into the β-annulus of the trimer locks the globular domain into the folded-back position. Superposition of a subunit from the VP5* antigen domain dimer on a subunit from the VP5CT trimer shows that during the two-fold to three-fold reorganization, most of the globular domain remains rigid, but the GH loop shifts position substantially, rotating relative to the rest of the domain, with a displacement of the residues at the tip of the loop. This loop appears to act as a molecular switch during the two-fold to three-fold rearrangment of VP4.

The N- and C-termini, which are close to each other, fold differently in the VP5* antigen domain dimer and in the VP5CT trimer. In the dimer, the N-terminus of one subunit crosses over to hydrogen bond to strand B of the other subunit, forming a new, inter-subunit β-strand A. In the other subunit of the dimer, the equivalent residues are either disordered or cleaved. In the VP5CT trimer, the N-terminus of each subunit folds back, forming strand A hydrogen bonded to strand B of its own subunit. Whether strand A is exchanged or retained, the same residues on strands A and B hydrogen bond to each other (252 to 268, 254 to 266, and 256 to 264). The crossed-over strand of the VP5* antigen dimer protrudes from the molecular envelope of the dimeric spike on the virion, making it doubtful that this cross-over occurs on the virion. The N-terminus of the ordered structure visible in the dimer electron density maps, residue A250, is close to the authentic VP5* N-terminus, residue A248. Cleavage to produce an N-terminus at A248, but not an alternative N-terminus at residue N242, primes particles for infectivity and cell-cell "fusion from without". The specificity of the priming cleavage suggests that the interactions of these N-terminal residues, in the unprimed, primed, or folded back states of the spike, are essential for the programmed rearrangements of VP4.

Comparison to Other Non-Enveloped Virus Spike Protein Domains.

As described above, the VP5* antigen domain has an eight-stranded β-sandwich at its core, with functional appendages mounted on that core. Three loops with hydrophobic tips that extend from one side of the β-sandwich are probably responsible for membrane interaction. A loop that projects from the other end of the domain is separated from the β-sandwich by the substitution of side chain-back bone hydrogen bonds for backbone-backbone hydrogen bonds, presents a highly exposed potential integrin binding motif, and may function in cell attachment. Here, we have shown that a dimer-to-trimer switch is added to the domain by the projecting GH loop and by sequences N-terminal and C-terminal to the β-sandwich.

The core framework on which these functions are mounted is unique—the DALI structural similarity search algorithm reveals no molecule in the Protein Data Bank that shares the fold of the VP5* antigen domain. Intriguingly, the closest match is the reovirus σ1 knob. Rotavirus and reovirus are both members of the family Reoviridae. VP4 and σ1 both form viral spikes that bind cell surface proteins and sialic acid. The σ1 eight-stranded anti-parallel β-barrel superimposes strikingly well on the VP5* antigen domain β-sandwich. However, the two proteins have different folds. The σ1 β-barrel has a double Greek key fold. Although the five C-terminal strands of the VP5CT β-sandwich share this connectivity, the three N-terminal strands are arranged in the opposite order. In addition, the structural elements that mediate host protein binding, sialic acid binding, and oligomerization by reovirus σ1 and rotavirus VP4 do not resemble each other. In contrast, structural and functional similarities (probably homologies) between reovirus σ1 and the adenovirus fiber are much more extensive. Neither the reovirus σ1 head nor the adenovirus fiber head appear to function in membrane penetration. Thus, a common ancestry for reovirus σ1 and the adenovirus fiber appears likely, but the relatedness of the VP5* antigen domain of rotavirus VP4 is less clear. A common ancestry for this VP5* domain and these other non-enveloped virus spike protein domains would necessitate a change in folding, with three-strand panel of β-structure flipping "inside out."

Conclusions.

The VP5* antigen domain folds autonomously, allowing its direct expression as a soluble protein. The domain can self-associate as well ordered dimers or well ordered trimers through alternative inter-subunit contacts between residues at the N- and C-termini and in an internal loop. Umbrella-shaped trimers of the domain form even without stabilization by a coiled-coil or an inter-subunit β-annulus, reinforcing the conclusion that VP5* has evolved to reorganize from a metastable primed spike to a trimeric final state. The structure of the dimeric form of the domain reveals the proximal two-fold contact of the spikes on trypsin primed virions. Using a newly developed recoating genetics system for rotavirus (manuscript in preparation) and this structural insight, it may be possible to introduce engineered, reversible disulfide cross-links that prevent spikes on recoated virions from reorganizing and folding back. This manipulation could reveal the function of VP4 rearrangement during cell entry. In addition, based on these high resolution structural data, it should be possible to engineer the VP5* antigen domain to optimize its characteristics for inclusion as a component of a subunit rotavirus vaccine.

Clearly, therefore, structural analysis can provide the basis for a technique to efficiently produce the VP5* neutralization targets. While VP5CT must be cleaved from a precursor to fold correctly, the VP5* antigen domain alone can be expressed directly and efficiently in insect cells. The current structures provide a strategy to increase the solubility of the VP5* antigen domain. In addition to its antigenic surfaces, the domain has antigenically "silent" surfaces, i.e. residues that are not essential for antigenicity. A fit to an image reconstruction of the spikes on triple-layered particles shows that the silent surfaces are inaccessible on the spike—they are buried in the dimer interface, located in an N-terminal region that rearranges, or masked by the VP8* heads. Both the N-terminal region and the masked region contribute to the surface of the directly expressed antigen domain and contain solvent-exposed hydrophobic side chains. Mutating these residues to present hydrophilic side chains could increase solubility while maintaining antigenicity. Another target for mutant residues includes residues not essential for structural stability. Both solubility and antigenicity will be assayed in the mutant molecules. Improving solubility will increase the efficiency of producing and purifying the VP5* antigen domain from insect cell culture by increasing the quantity of protein in lysed cell supernatants and eliminating the need to maintain modest protein concentrations during purification. Codon optimization should further increase yield.

As neutralization epitopes on the VP5* antigen domain are generally heterotypic, the need to include multiple P types is limited. However, as one serotype-specific (P[8]) epitope (5-5) has been described, a VP5CT antigen domain from a P[8] strain (Wa or KU) will be expressed and characterized. Immunization with this variant will allow homotypic challenge in the gnotobiotic pig model, which can be compared to heterotypic challenge after immunization with the RRV VP5* antigen domain.

A second generation of constructs is currently being developed in order to address heterogeneity and solubility issues observed in the current recombinant proteins. Conservative VP5* sequence boundary changes are also being incorporated in order to address solubility issues and attempt to produce a monomeric antigen. Cleavable GCN4 and disulfide bonds may be introduced into the second generation of constructs. Future construct design will no doubt include efforts to more aggressively alter the biochemical and antigenic properties of the antigen domain based on the structural information presented here and on antigenicity data that will be provided in ongoing studies.

Example 10

Comparison of Neutralizing Antibody Responses Against the Cleaved and Uncleaved Membrane Interaction Domain As described above, the membrane interaction region of VP4 has three distinct conformations. The uncleaved and post-membrane interaction states can both be isolated in solution, and both are potentially useful antigens. Immunization with these two forms of VP4 will be compared for efficacy at inducing neutralizing antibodies. Intact VP4 may be modified to remove its hemagglutination domain, which may elicit neutralizing antibodies that complicate the analysis, and to alter the trypsin activation sites, preventing cleavage by trace proteases.

Example 11

Efficacy Studies

The studies described above focus on the protein engineering of rotavirus antigens. Ultimately, the delivery of these antigens must be optimized to elicit and maintain a protective amount of antibody in the gut lumen of children. The design of a suitable delivery system is a long-term goal, beyond the scope of this proposal.

Protection afforded by individual optimized antigens, optimal mixes of antigens, breadth of included stereotypic variants, choice of adjuvants, and immunization protocols may be assessed using animal models. The many potential combinations of antigens, platforms, adjuvants, and protocols necessitates initial testing in an efficient small animal model. These protection studies will assess both active immunity and passively transferred colostral immunity; immunity against disease in pups and infection in adults; challenge with a virulent, antigenically distant virus and a less virulent, antigenically similar virus.

Murine Animal Models

At least two convenient mouse models may be used to assess immunization with recombinant rotavirus proteins. One model assesses passive protection of suckling pups from rotavirus diarrhea by colostral antibody. Newborn pups are suckled on immunized dams. To test for immunity passively transferred by breast milk, the pups are challenged with a simian rotavirus strain (RRV) or a tissue culture-adapted murine rotavirus stain (Eb). The presence or absence of diarrhea and/or viral shedding is assessed. Trans-placental serum neutralizing antibody in pups born to immunized dams does not protect. Colostral antibody in pups suckled on immunized dams does protect. The second, more recently developed model tests active protection of adult mice against rotavirus infection (but not diarrhea). Immunized mice are challenged with virulent murine rotavirus strains that are passaged from mouse to mouse. Rotavirus shed in stool is assayed quantitatively by ELISA. This model has allowed sophisticated assessment of correlates of immunity against rotavirus infection.

The suckling mouse model was used for challenge studies after recombinant outer capsid protein immunization. Pregnant dams were immunized intraperitoneally (i.p.) or intramuscularly (i.m.) with insect cell lysates containing recombinant VP4, VP8*, VP5* (residues 247-474), or VP7 in Freund's adjuvant. VP4 was the most successful immunogen (all pups protected from homotypic challenge, most protected from heterotypic challenge); VP7 was the least effective (23% of pups protected from homotypic challenge); VP8* and VP5* gave intermediate levels of protection. In these studies, the immunogens were not homogeneous or pure, let alone optimized, and i.p. inoculation in Freund's adjuvant does not model a potential human immunization protocol. These studies do, however, provide a proof of concept for protective immunization with recombinant rotavirus outer capsid proteins.

For experiments in the suckling mouse pup model, CD-1 female mice may be immunized and boosted starting at 4 weeks of age and may be bred with adult males at 15-16 weeks of age. At least three litters should be included in both the sample and control groups. Suckling pups, 4-5 days old, may be challenged with a dose of RRV that causes diarrhea in >90% of naïve mice. The presence of diarrhea in the pups may be determined by expression of liquid stool upon gentle palpation of the abdomen. The criterion for successful protection is a >90% reduction in the number of pups with diarrhea. Serum antibody response in the dams may be assayed by ELISA, neutralization of heterotypic and homotypic rotaviruses, and immunoprecipitation of $^{35}S$-labeled rotavirus proteins (to confirm that the immune response is directed against the immunizing antigen).

In other studies using a variation of the above-described suckling mouse pup model, female Balb/c mice that were 9 weeks of age were obtained, prebled and their seronegativity confirmed. Five groups each containing five of these female Balb/c mice were immunized subcutaneously at 10 weeks of age with 25 micrograms of (1) recombinant VP8*, (2) recombinant VP5* antigen domain (residues 247-479), (3) recombinant VP4, (4) a negative control and (5) purified RRV TLPs in Freund's complete adjuvant. A first booster injection in Freund's incomplete adjuvant was given to each group three weeks later, and a second booster injection in Freund's incomplete adjuvant was given to each group two weeks after the first boost. The total amount of protein administered to each mouse of each group was 0.375 mg. The female mice were bred with 25 Balb/c mice at 15 weeks of age (at the time of the second booster). The dams were bled and neutralization/immunoprecipitation assays (ELISA to assess seroconversion, neutralization assays of heterotypic and homotypic rotaviruses (RRV, Wa, NCDV), and immunoprecipitation assays of $^{35}S$-labeled rotavirus proteins to assess specificity) were performed approximately three weeks after breeding but several days prior to the challenge of the suckling pups. The suckling pups, 4-5 days old, were challenged with a dose of RRV that causes diarrhea in >90% of naïve mice.

Concurrently, the immunogens may also be tested in an adult mouse model of protection from infection. Immunization with the RRV VP8* core (P[3]) followed by EC challenge (P[16]) will allow assessment of heterotypic protection by this antigen. If heterotypic protection is not achieved with this immunization, a murine rotavirus VP8* core will be produced to test for homotypic protection.

Adult mouse studies to test active protection will use several modifications to this protocol. Each sample and control group will contain approximately 10 mice. Immunized mice will be challenged with $10^4$ $SD_{50}$ (50% shedding dose) of ECw, a virulent murine rotavirus (P[16]G3), passaged in mice and prepared as an intestinal homogenate. Stomach acidity will be neutralized with bicarbonate before oral challenge. Protection will be assessed by ELISA for rotavirus antigen shed in stool. In some experiments, ELISA to detect rotavirus-specific IgA in feces or ELISPOT of lamina propria B cells will be used to measure gut immunity. ELISPOT of spleen and bone marrow B cells will be used to detect systemic responses. B cell ELISPOT selectively detects antibody-secreting cells (ASC) that produce rotavirus-specific IgA, IgM, and IgG.

By testing individual optimized antigens in a suckling mouse model we can compare new results to baseline results using recombinant rotavirus outer capsid immunogens in this system. Antigens will be assessed for immunogenicity and antigenicity. For non-oral immunizations, the protease and acid resistance criteria will be relaxed. As in the baseline studies, mice will be immunized intra-peritoneally (IP) with antigens mixed in Ribi adjuvant. Immunizing antigens will be from strain RRV, matching the challenge strain.

Adult mice may be immunized to actively protect the immunized animals against infection with EC (a highly virulent, heterotypic, murine rotavirus) and to passively protect suckling pups against disease caused by EC and RRV (a homotypic simian rotavirus). Mouse models for passive (colostral) protection from heterologous (simian rotavirus) disease or active protection from homologous (murine rotavirus) infection allow numerous experimental questions to be answered efficiently, providing "proof of principle." While the specific immunization and challenge protocols will vary with the experimental questions, a consistent set of procedures and measurements will facilitate comparisons between experiments. All mice will be screened for preexisting anti-rotavirus antibodies, with an ELISA titer of <1:50 against purified rotavirus used as a criterion for inclusion.

Porcine Animal Models

Porcine animal models may also be used to assess the efficacy of individual optimized antigens, optimal mixes of antigens, breadth of included stereotypic variants, choice of adjuvants, and immunization protocols. The neonatal gnotobiotic pig provides an accurate available predictor of efficacy in human infants and children (months 13-60). Immunization schemes that have appeared effective in small animal testing have failed in the porcine model (but not vice versa). No immunization scheme that fails in the pig model would be considered for humans.

Neonatal gnotobiotic pigs are susceptible to diarrhea caused by the human rotavirus strain, Wa (G1P[8]), as well as a second human rotavirus strain, IM (G3P[8]), which will allow for a heterotypic G type challenge. A heterotypic P type challenge is also being prepared, based on strain HRV US1205 (G9P[6]). Like humans, pigs do not develop significant maturational resistance to rotavirus diarrhea, so that active immunity and protection against infection and disease can be tested. Protection from challenge in the neonatal gnotobiotic pig model correlates well with results of vaccine trials using Jennerian rotavirus vaccine candidates, so that efficacy in this model is currently the best predictor of successful immunization of children. The best correlates of immunity stimulated by rotavirus infection in gnotobiotic pigs are the presence of intestinal rotavirus-specific IgA primary antibody secreting cells (ASC), as measured by ELISPOT, and rotavirus-specific IgA levels in intestinal contents, as measured by ELISA.

Neonatal gnotobiotic pigs may be delivered aseptically by hysterectomy and housed under sterile conditions in isolator units. A typical experiment includes 12 test animals and 6 controls. Pigs may be immunized at 3-5 days of age with optimized antigens, adjuvants, and routes, selected based on the results of tests in mice and on the potential for use in humans. Three to six animals each from the test and control groups may be euthanized at the time of challenge to assess the induced B and T cell responses. Animals may be orally challenged with $10^6$ pig $ID_{50}$ of a virulent strain of the human rotavirus Wa (P[8]G1), prepared as a suspension of intestinal contents. This dose causes diarrhea in nearly 100% of naïve pigs. Similar preparations of virulent strain M (P[8]G3) or US1205 (P[6]G9) human rotaviruses may be used to assess heterotypic protection. Stomach acidity may be neutralized with sodium bicarbonate before challenge. Protection may be determined by visual assessment of diarrhea and by testing stool for shed antigen by ELISA or for infectious virus by fluorescent focus assay. B cell responses may be assessed by serum neutralization; by isotype-specific ELISA for serum antibody; and by ELISPOT of mononuclear cells from intestinal lamina propria, mesenteric lymph nodes, spleen, and peripheral blood. To assess T cell responses, ELISPOT may be used to detect precursor T cells that secrete IFN-γ, IL-12, IL-4 or IL-10, and serum levels of these cytokines will be measured by ELISA.

The criterion for moving to gnotobiotic pig immunizations with individual recombinant antigens will be 90% protection from infection in the adult mouse model. In the event that individual antigens do not achieve this level of protection, mixtures of antigens will be tested in mice. While baseline conditions for protective immunizations with inert antigens have been established in mice, intramuscular (i.m.) immunization of gnotobiotic pigs with inactivated Wa rotavirus particles in incomplete Freund's adjuvant fails to protect against virulent Wa challenge, and an effective non-replicating primary immunization strategy has yet to be identified in the pig model.

Example 12

Elicitation of Neutralizing Antibodies with VP5* Constructs

Stably multivalent presentation of VP5* epitopes appears significantly more effective at eliciting neutralizing antibodies. Sera produced by immunizing mice with the VP5CT trimer (P[3]) neutralize homotypically at 1:800 to 1:25,600 and neutralize heterotypically at 1:100 to 1:1600. VP5Ag and VP5CT share all known neutralization epitopes. Results are shown below in Table 3:

TABLE 3

|  | RRV | VP4 | VP5Ag | VP8core |
|---|---|---|---|---|
| ELISA vs. virions (GMT) | 128,000 | 32,000 | <66 | 605 |
| Neut. vs. RRV (GMT) | 117,490 | 135,520 | <50 | <50 |
| Diarrhea in suckling pups (%) | 0 | 0 | 30 | 62.5 |

Example 13

Use of VP8* Octamers as Immunogens

NSP2-VP8-gen1 and NSP2-VP8-gen2, depicted in FIG. 15, were analyzed by SDS-PAGE, gel filtration chromatography, and equilibrium analytical ultracentrifugation. Both are form octamers. NSP2-VP8* gen1 is unstable and susceptible to proteolysis, leading to dissociation of VP8*. The long linker between NSP2 and VP8* may have caused tangling during octamerization. However, NSP2-VP8-gen 2 forms stable octamers.

Figure 16:
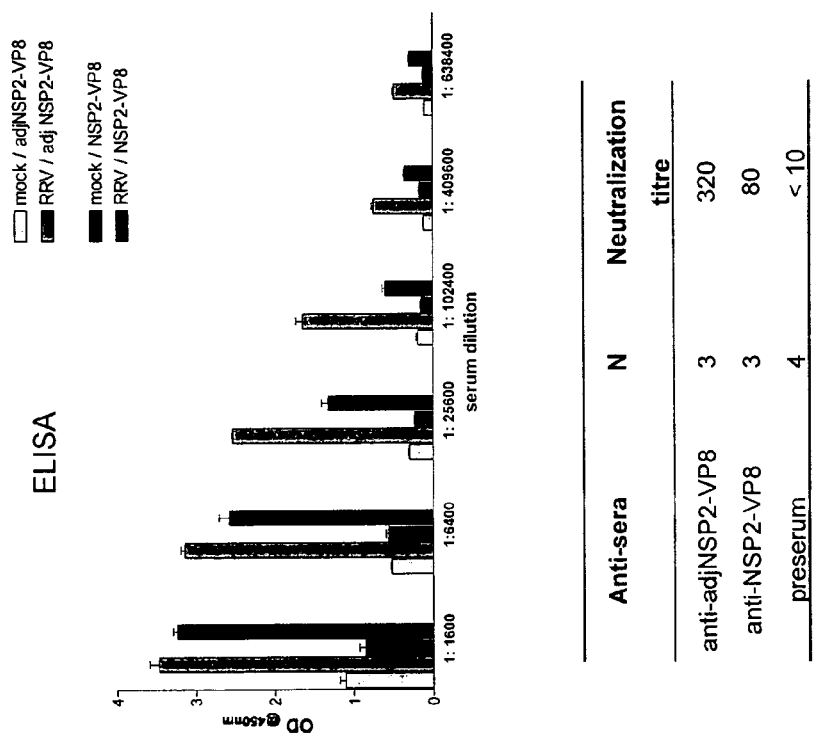
FIG. 16 depicts ELISA and neutralization titers from immunized guinea pig sera for an NSP2-VP8 octamer (Gen 2).

Fusion to NSP2 appears to increase the immunogenicity of the VP8* core. The VP8* core alone was not effective at eliciting neutralizing antibodies in mice, but the NSP2-VP8* core fusion (gen2) elicits a 1:640 neutralizing titer in guinea pigs (FIG. 16).

Example 14

Neutralizing Antibodies React with the VP5* and VP8* Domains

The VP5* antigen domain was shown to react with two neutralizing antibodies (2G4 and YO2C2) in an ELISA assay and the VP8* core was shown to react with a neutralizing antibody (7A12) via a Western blot.

EQUIVALENTS

The present invention provides in part novel recombinant polypeptide antigens that may serve as novel subunit vaccines against rotavirus infection. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications and patents mentioned herein, including those items listed below, are hereby incorporated by reference in their entireties as if each individual publication or patent was specifically and individually indicated to be incorporated by reference. In case of conflict, the present application, including any definitions herein, will control. Lawton, et al., *Nat Struct Biol* 4, 118-121 (1997); Parashar, et al., *Emerg Infect Dis* 9, 565-572 (2003); Ruggeri, et al., *J Viro* 65, 2211-2219 (1991); Offit, et al., *J Virol* 58, 700-703 (1986); Shaw, et al., *Cell* 74, 693-701 (1993); Yeager, et al., *Embo J* 13, 1011-1018 (1994); Dormitzer, et al., *Virology* 277, 420-428 (2000); Dormitzer, et al., *J Virol* 75, 7339-7350 (2001); Dormitzer, et al., *EMBO J* 21, 885-897 (2002); Crawford, et al., *J Viro* 75, 6052-6061 (2001); Graham, K. L. et al., *J Virol* 77, 9969-9978 (2003); Mackow, et al., *Proc Natl Acad Sci USA* 85, 645-649 (1988); Dowling, et al., *J Virol* 74, 6368-6376 (2000); Arias, et al., *J Virol* 70, 5832-5839 (1996); Gilbert, et al., *J Virol* 72, 5323-5327 (1998); Arnaout, et al. *Curr Opin Cell Biol* 14, 641-651 (2002); Rey, et al., *Nature* 375, 291-298 (1995); Lescar, et al., *Cell* 105, 137-148 (2001); Holm, et al., *J Mol Biol* 233, 123-138 (1993); Chappell, et al., *Embo J* 21, 1-11 (2002); Liemann, et al., *Cell* 108, 283-295 (2002); Tihova, et al., *J Mol Biol* 314, 985-992 (2001); Taniguchi, et al., *J Virol* 62, 2421-2426 (1988); Prasad, et al., *J Mol Biol* 199, 269-275 (1988); Yeager, et al., *J Cell Biol* 110, 2133-2144 (1990); Prasad, et al., *Nature* 343, 476-9 (1990); Ruigrok, et al., *J Gen Virol* 69, 2785-2795 (1988); Weissenhorn, et al., *Embo J* 15, 1507-1514 (1996); Modis, et al., *Nature* 427, 313-319 (2004); Gibbons, et al., *Nature* 427, 320-325 (2004); Padilla, et al., *Acta Crystallogr D Biol Crystallogr* 59, 1124-1130 (2003); Collaborative Computational Project, N., *Acta Crystallogr* D50, 760-763 (1994); Weeks, et al., *J Appl Cryst* 32, 120-124 (1999); Jones, et al., *Acta Crystallogr A* 47, 110-119 (1991); Brunger, et al., *Acta Crystallogr D Biol Crystallogr* 54, 905-921 (1998); Kleywegt, et al., *Acta Crystallogr D*52, 842-857 (1999); Kleywegt, G. J., *Acta Crystallogr* D52, 842-857 (1996); Laskowski, et al., *J Appl Cryst* 26, 283-291 (1993); Crowther, R. A., *Philos Trans R Soc Lond B Biol Sci* 261, 221-230 (1971); Lawton, et al., *J Struct Biol* 116, 209-215 (1996); Ludtke, et al., *J Struct Biol* 128, 82-97 (1999); Wriggers, et al., *J Struct Biol* 125, 185-195 (1999); Livingstone, et al., *Comput Appl Biosci* 9, 745-756 (1993); Kraulis, J., J *Appl Cryst* 24, 946-950 (1991); Nicholls, et al., *Proteins: Structure, Function, and Genetics* 11, 281-296 (1991); Kirkwood, et al., *Arch Virol* 141, 587-600 (1996); Padilla-Noriega, et al., *Virology* 206, 148-154 (1995); Kobayashi, et al., *J Gen Virol* 71, 2615-2623 (1990); Gorziglia, et al., *J Virol* 64, 4534-4539 (1990); Matsui, et al., *Adv Virus Res* 36, 181-214 (1989); Ludert, et al., *J Virol* 76, 6643-51 (2002); Chandran, et al., *J Virol* 75, 5335-42 (2001); Dormitzer, et al., *Virology* 189, 828-32 (1992); Dormitzer, et al., *Virology* 187, 18-32 (1992); Dormitzer, et al., *J Virol* 76, 10512-7 (2002); World Health Organization, *Wkly Epidemiol Rec* 74, 33-8 (1999); Centers for Disease Control, *MMWR Morb Mortal Wkly Rep* 48, 1007 (1999); Shaw, et al., *Virology* 155, 434-51 (1986); Andrew, et al., *Vaccine* 10, 185-91 (1992); Walz, et al., *J Struct Biol* 121, 142-61 (1998); Ciarlet, et al., *J Gen Virol* 80, 943-8 (1999); Ludert, et al., *J Gen Virol* 79, 725-9 (1998); Gentsch, et al., *J Infect Dis* 174 Suppl 1, S30-6 (1996); Burns, et al., *Virology* 207, 143-53 (1995); Esposito, et al., *Field's Virology* 2885-2921 (2001); Kapikian, et al., *Am J Epidemiol* 89, 405-21 (1969); Collins, et al., *Field's Virology* 1443-1485 (2001); Recommendations of the Immunization Practices Advisory Committee (ACIP), *MMWR Recomm Rep* 41, 1-10 (1992); Wiley, et al., *Nature* 289, 373-8 (1981); Wyatt, et al., *Nature* 393, 705-11 (1998); Zhang, et al., *Biochemistry* 38, 9405-16 (1999); Kapikian, et al., *J Infect Dis* 153, 815-22 (1986); Withdrawal of rotavirus vaccine recommendation, *MMWR Morb Mortal wkly Rep* 48, 1007 (1999); Svensson, et al., *J Gen Virol* 68 (Pt 7), 1993-9 (1987); Franco, et al., *Virology* 238, 169-79 (1997); Franco, et al., *J Virol* 69, 7800-6 (1995); Offit, et al., *J Virol* 54, 58-64 (1985); Matson, et al., *J Infect Dis* 167, 577-83 (1993); Coulson, et al., *J Clin Microbiol* 30, 1678-84 (1992); Prasad, et al., *Curr Top Microbiol Immunol* 185, 9-29 (1994); Estes, et al., *J Virol* 39, 879-88 (1981); Mackow, et al., *Virology* 165, 511-7 (1988); Hoshino, et al., *Arch Virol Suppl* 12, 99-111 (1996); Fiore, et al., *Virology* 181, 553-63 (1991); Burns, et al., *Science* 272, 104-7 (1996); Schwartz-Cornil, et al., *J Virol* 76, 8110-7 (2002); Ciarlet, et al., *J Virol* 72, 923346 (1998); Bertolotti-Ciarlet, et al., *Vaccine* 21, 3885-900 (2003); Yuan, et al., *J Virol* 74, 8843-53 (2000); Mackow, et al., *J Virol* 63, 1661-8 (1989); Fiore, et al., *J Gen Virol* 76, 1981-8 (1995); Gajardo, et al., *J Virol* 71, 2211-6 (1997); Andrew, et al., *J Virol* 64, 4776-83 (1990); Dormitzer, et al., *Virology* 204, 391402 (1994); Cohen, et al., *Arch Virol* 60, 177-86 (1979); Franco, et al., *Trends Microbiol* 8, 50-2 (2000); Mackow, et al., *J Virol* 64, 1698-703 (1990); Dunn, et al., *Arch Virol* 140, 1969-78 (1995); Yuan, et al., *Vet Immunol Immunopathol* 87, 147-60 (2002); Yuan, et al., *J Virol* 70, 3075-83 (1996); Crawford, et al., *J Virol* 73, 4813-22 (1999); Desselberger, et al., *Novartis Found Symp* 238, 125-47, discussion 147-52 (2001); Godley, et al., *Cell* 68, 635-45 (1992); Tessier, et al., *Gene* 98, 177-83 (1991); Bachmann, et al., *Science* 262, 1448-51 (1993); Mowat, et al., *Immunol Lett* 65, 133-40 (1999); Jayaram, et al., *Nature* 417, 311-5 (2002); Mathieu, et al., *Embo J* 20, 1485-97 (2001); Schuck, et al., *J Biol Chem* 276, 9679-87 (2001); Yuan, et al., *J Virol* 75, 9229-38 (2001); Lepault, et al., *Embo J* 20, 1498-507 (2001); Gilbert, et al., *Arch Virol* 146, 1155-71 (2001); Yuan, et al., *J Virol* 72, 330-8 (1998); Chong, et al., *Vaccine* 16, 73240 (1998); Douce, et al., *Infect Immun* 67, 4400-6 (1999); Halperin, et al., *Vaccine* 21, 2461-7 (2003); Roman, et al., *Nat Med* 3, 849-54 (1997); Lovgren, et al., *Mol Immunol* 28, 285-6 (1991); Choi, et al., *J Virol* 73, 7574-81 (1999); Mutsch, et al., *N Engl J Med* 350, 896-903 (2004); McCluskie, et al., *J Immunol* 161, 4463-6 (1998); Lycke, *Cell Microbiol* 6, 23-32 (2004); Gonzalez, et al., *Clin Exp Immunol* 135, 361-72 (2004); Carpio, et al., *J Biol Chem* 279, 10624-33 (1994).

The invention claimed is:

1. A soluble, isolated recombinant antigenic polypeptide having at least about 85% amino acid identity to the entire amino acid sequence of SEQ ID NO:1 or 2.

2. The soluble, isolated recombinant antigenic polypeptide of claim 1, comprising any one of the epitopes selected from the group consisting of: 8-1, 8-2, 8-3, and 8-4.

3. The soluble isolated recombinant antigenic polypeptide of claim 1, wherein the polypeptide is expressed as a fusion protein.

4. The soluble isolated recombinant antigenic polypeptide of claim 1, which is protease-resistant.

5. An immunogenic composition comprising SEQ ID NO:1.

6. An immunogenic composition comprising SEQ ID NO:2.

* * * * *

UNITED STATES PATENT AND TRADEMARK OFFICE
CERTIFICATE OF CORRECTION

PATENT NO. : 8,685,411 B2  
APPLICATION NO. : 11/649191  
DATED : April 1, 2014  
INVENTOR(S) : Philip R. Dormitzer et al.

Page 1 of 1

It is certified that error appears in the above-identified patent and that said Letters Patent is hereby corrected as shown below:

In the Specification

At Column 1, Line number 12, replace the information listed under "GOVERNMENT SUPPORT" as follows:

This invention was made with Government support under Grant Number R01 A1053174, R01 CA013202 and K08 A1001496 awarded by the National Institutes of Health. The Government has certain rights in the invention.

Signed and Sealed this  
Fourth Day of April, 2017

Michelle K. Lee  
*Director of the United States Patent and Trademark Office*